US009480744B2

(12) United States Patent
Hoey et al.

(10) Patent No.: US 9,480,744 B2
(45) Date of Patent: *Nov. 1, 2016

(54) METHODS FOR TREATING MELANOMA

(71) Applicant: OncoMed Pharmaceuticals, Inc., Redwood City, CA (US)

(72) Inventors: Timothy C. Hoey, Hillsborough, CA (US); Lucia Beviglia, Redwood City, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 14/020,567

(22) Filed: Sep. 6, 2013

(65) Prior Publication Data
US 2014/0065149 A1  Mar. 6, 2014

Related U.S. Application Data

(63) Continuation of application No. 13/229,006, filed on Sep. 9, 2011, now Pat. No. 8,551,479.

(60) Provisional application No. 61/381,628, filed on Sep. 10, 2010.

(51) Int. Cl.
*A61K 39/395* (2006.01)
*C07K 16/22* (2006.01)
*C07K 16/24* (2006.01)
*C07K 16/28* (2006.01)
*A61K 45/06* (2006.01)
*A61K 47/48* (2006.01)
*C12Q 1/68* (2006.01)
*C07K 16/30* (2006.01)
*A61K 39/00* (2006.01)

(52) U.S. Cl.
CPC ..... *A61K 39/3955* (2013.01); *A61K 39/39533* (2013.01); *A61K 45/06* (2013.01); *A61K 47/48284* (2013.01); *C07K 16/28* (2013.01); *C12Q 1/6886* (2013.01); *A61K 39/39558* (2013.01); *A61K 2039/505* (2013.01); *A61K 2039/507* (2013.01); *C07K 16/22* (2013.01); *C07K 16/24* (2013.01); *C07K 16/30* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,816,567 A | 3/1989 | Cabilly et al. |
| 5,013,556 A | 5/1991 | Woodle et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,730,977 A | 3/1998 | Ooka et al. |
| 5,731,168 A | 3/1998 | Carter et al. |
| 5,750,373 A | 5/1998 | Garrard et al. |
| 5,840,299 A | 11/1998 | Bendig et al. |
| 6,004,528 A | 12/1999 | Bergstein |
| 6,024,955 A | 2/2000 | Asano et al. |
| 6,121,045 A | 9/2000 | McCarthy et al. |
| 6,262,025 B1 | 7/2001 | Ish-Horowicz et al. |
| 6,342,219 B1 | 1/2002 | Thorpe et al. |
| 6,524,583 B1 | 2/2003 | Thorpe et al. |
| 6,582,959 B2 | 6/2003 | Kim et al. |
| 6,664,098 B1 | 12/2003 | Sakano |
| 6,676,941 B2 | 1/2004 | Thorpe et al. |
| 6,689,744 B2 | 2/2004 | Gao et al. |
| 6,887,468 B1 | 5/2005 | Thorpe et al. |
| 6,984,522 B2 | 1/2006 | Clarke et al. |
| 7,022,499 B2 | 4/2006 | Sakano |
| 7,056,509 B2 | 6/2006 | Thorpe et al. |
| 7,060,269 B1 | 6/2006 | Baca et al. |
| 7,118,890 B2 | 10/2006 | Ish-Horowicz et al. |

(Continued)

FOREIGN PATENT DOCUMENTS

CA    2789446 A1    8/2011
EP    0662827 A1    7/1995

(Continued)

OTHER PUBLICATIONS

Brummell et al. (Biochemistry 32:1180-1187 (1993)).*

(Continued)

*Primary Examiner* — Bridget E Bunner
(74) *Attorney, Agent, or Firm* — Sterne, Kessler, Goldstein & Fox PLLC

(57) ABSTRACT

Methods of inhibiting melanoma tumor growth, methods of treating melanoma and metastatic melanoma, and methods of reducing the frequency of tumor initiating cells (or cancer stem cells) in melanoma tumors are described. The methods described comprise administering a DLL4 antagonist (e.g., an antibody that specifically binds the extracellular domain of human DLL4) to a subject. Related polypeptides and polynucleotides, compositions comprising the DLL4 antagonists, and methods of making the DLL4 antagonists are also described.

20 Claims, 12 Drawing Sheets

(56) References Cited

U.S. PATENT DOCUMENTS

| | | |
|---|---|---|
| 7,183,076 B2 | 2/2007 | Arathoon et al. |
| 7,227,004 B2 | 6/2007 | Kim |
| 7,354,581 B2 | 4/2008 | Cedarbaum et al. |
| 7,449,182 B2 | 11/2008 | Cedarbaum et al. |
| 7,482,005 B2 | 1/2009 | Kim et al. |
| 7,488,806 B2 | 2/2009 | Papadopoulos et al. |
| 7,531,172 B2 | 5/2009 | Stahl et al. |
| 7,534,868 B1 | 5/2009 | Papadopoulos et al. |
| 7,750,124 B2 | 7/2010 | Gurney et al. |
| 7,754,206 B2 | 7/2010 | Clarke et al. |
| 7,758,859 B2 | 7/2010 | Fuh et al. |
| 7,951,917 B1 | 5/2011 | Arathoon et al. |
| 8,048,418 B2 | 11/2011 | Noguera-Troise et al. |
| 8,216,571 B2 | 7/2012 | Ramachandra et al. |
| 8,551,479 B2 | 10/2013 | Hoey et al. |
| 8,858,941 B2 | 10/2014 | Gurney et al. |
| 8,883,145 B2 | 11/2014 | Stagg et al. |
| 2002/0028488 A1 | 3/2002 | Singh et al. |
| 2002/0032315 A1 | 3/2002 | Baca et al. |
| 2003/0175877 A1 | 9/2003 | Baker et al. |
| 2003/0180784 A1 | 9/2003 | McCarthy et al. |
| 2004/0123343 A1 | 6/2004 | La Rosa et al. |
| 2004/0133357 A1 | 7/2004 | Zhong et al. |
| 2004/0265307 A1 | 12/2004 | Singh et al. |
| 2004/0265309 A1 | 12/2004 | Kandel et al. |
| 2005/0026831 A1 | 2/2005 | Bodmer et al. |
| 2005/0054036 A1 | 3/2005 | Bates et al. |
| 2005/0059093 A1 | 3/2005 | Bodmer et al. |
| 2005/0079184 A1 | 4/2005 | Hsing-Chang et al. |
| 2005/0089518 A1 | 4/2005 | Clarke et al. |
| 2005/0112121 A1 | 5/2005 | Artavanis-Tsakonas et al. |
| 2005/0137130 A1 | 6/2005 | Bodmer et al. |
| 2005/0261477 A1 | 11/2005 | Champion et al. |
| 2005/0276808 A1 | 12/2005 | Cedarbaum |
| 2005/0281822 A1 | 12/2005 | Cedarbaum et al. |
| 2006/0084588 A1 | 4/2006 | Briend et al. |
| 2006/0122373 A1 | 6/2006 | McCarthy et al. |
| 2006/0134080 A1 | 6/2006 | Lyden et al. |
| 2006/0134121 A1 | 6/2006 | Thurston et al. |
| 2006/0280747 A1 | 12/2006 | Fuh et al. |
| 2006/0293340 A1* | 12/2006 | Batt et al. ................ 514/255.05 |
| 2007/0004909 A1 | 1/2007 | Johnson et al. |
| 2007/0020267 A1 | 1/2007 | Fuh et al. |
| 2007/0036797 A1 | 2/2007 | Kim et al. |
| 2007/0082846 A1 | 4/2007 | Ish-Horowicz et al. |
| 2007/0098712 A1 | 5/2007 | Arathoon et al. |
| 2007/0141065 A1 | 6/2007 | Fuh et al. |
| 2007/0154391 A1 | 7/2007 | Kim et al. |
| 2007/0178552 A1 | 8/2007 | Arathoon et al. |
| 2007/0190647 A1 | 8/2007 | Clarke et al. |
| 2007/0196374 A1 | 8/2007 | Baca et al. |
| 2007/0202102 A1 | 8/2007 | Bizzini et al. |
| 2007/0212354 A1 | 9/2007 | Yung et al. |
| 2007/0213266 A1 | 9/2007 | Gill et al. |
| 2007/0231325 A1 | 10/2007 | Clarke et al. |
| 2007/0287170 A1 | 12/2007 | Davis et al. |
| 2008/0014196 A1 | 1/2008 | Yan |
| 2008/0063635 A1 | 3/2008 | Takahashi et al. |
| 2008/0069820 A1 | 3/2008 | Fuh et al. |
| 2008/0107648 A1 | 5/2008 | Noguera et al. |
| 2008/0175847 A1 | 7/2008 | Yan et al. |
| 2008/0181893 A1 | 7/2008 | Lobov et al. |
| 2008/0181899 A1 | 7/2008 | Papadopoulos et al. |
| 2008/0187532 A1* | 8/2008 | Gurney et al. ............. 424/133.1 |
| 2008/0220495 A1 | 9/2008 | McCarthy et al. |
| 2009/0004205 A1 | 1/2009 | Clarke et al. |
| 2009/0023591 A1 | 1/2009 | Spanuth |
| 2009/0035308 A1 | 2/2009 | Gill et al. |
| 2009/0221549 A1 | 9/2009 | Gerber et al. |
| 2009/0246199 A1 | 10/2009 | Noguera-Troise et al. |
| 2009/0286956 A1 | 11/2009 | McCarthy et al. |
| 2010/0015133 A1 | 1/2010 | Igawa et al. |
| 2010/0076178 A1 | 3/2010 | Ghayur et al. |
| 2010/0086518 A1* | 4/2010 | Heise et al. ................ 424/85.2 |
| 2010/0086544 A1 | 4/2010 | Mass et al. |
| 2010/0129356 A1 | 5/2010 | Yan |
| 2010/0150940 A1 | 6/2010 | Adam et al. |
| 2010/0215779 A1 | 8/2010 | Currie et al. |
| 2010/0221250 A1 | 9/2010 | Kim et al. |
| 2010/0260668 A1 | 10/2010 | Ghayur et al. |
| 2010/0266589 A1 | 10/2010 | Hedrick et al. |
| 2010/0272733 A1 | 10/2010 | Bates et al. |
| 2010/0286374 A1 | 11/2010 | Kannan et al. |
| 2010/0316637 A1 | 12/2010 | Gurney et al. |
| 2011/0052575 A1 | 3/2011 | Baca et al. |
| 2011/0052576 A1 | 3/2011 | Ferrara et al. |
| 2011/0076279 A1 | 3/2011 | Ramachandra et al. |
| 2011/0081342 A1 | 4/2011 | Baca et al. |
| 2011/0123532 A1 | 5/2011 | Gurney et al. |
| 2011/0165162 A1 | 7/2011 | Hoey et al. |
| 2011/0172398 A1 | 7/2011 | Borges et al. |
| 2011/0217237 A1 | 9/2011 | Chen et al. |
| 2012/0116057 A1 | 5/2012 | Kannan et al. |
| 2012/0263721 A1 | 10/2012 | Stagg et al. |
| 2013/0164295 A1 | 6/2013 | Gurney et al. |
| 2013/0253172 A1 | 9/2013 | Gurney et al. |
| 2013/0266569 A1 | 10/2013 | Gurney et al. |
| 2013/0323265 A1 | 12/2013 | Stagg et al. |
| 2014/0220001 A1 | 8/2014 | Benner et al. |
| 2014/0227252 A1 | 8/2014 | Benner et al. |
| 2015/0098949 A1 | 4/2015 | Gurney et al. |
| 2015/0118232 A1 | 4/2015 | Stagg et al. |

FOREIGN PATENT DOCUMENTS

| | | |
|---|---|---|
| EP | 0 861 894 A1 | 9/1998 |
| EP | 1004669 A1 | 5/2000 |
| EP | 0 662 827 B1 | 4/2002 |
| EP | 1179541 B1 | 6/2004 |
| EP | 0979281 B1 | 7/2005 |
| EP | 0 972 041 B1 | 10/2006 |
| EP | 1 004 669 B1 | 4/2007 |
| EP | 1810979 A1 | 7/2007 |
| EP | 1870459 A1 | 12/2007 |
| GB | 2 449 354 A | 11/2008 |
| JP | 2005511754 A | 4/2005 |
| WO | WO 92/19734 A1 | 11/1992 |
| WO | WO 94/07474 A1 | 4/1994 |
| WO | WO 97/01571 A1 | 1/1997 |
| WO | WO 98/45434 A1 | 10/1998 |
| WO | WO-9845331 A2 | 10/1998 |
| WO | WO 98/51799 A1 | 11/1998 |
| WO | WO-9849302 A1 | 11/1998 |
| WO | WO 98/57621 A1 | 12/1998 |
| WO | WO 00/06726 A2 | 2/2000 |
| WO | WO-0107611 A2 | 2/2001 |
| WO | WO 01/40466 A2 | 6/2001 |
| WO | WO-0177169 A2 | 10/2001 |
| WO | WO 02/12447 A2 | 2/2002 |
| WO | WO-03041735 A2 | 5/2003 |
| WO | WO-03050502 A2 | 6/2003 |
| WO | WO-2004110490 A2 | 12/2004 |
| WO | WO 2006/027693 A2 | 3/2006 |
| WO | WO-2006028936 A2 | 3/2006 |
| WO | WO-2006033386 A1 | 3/2006 |
| WO | WO 2006/052128 A1 | 5/2006 |
| WO | WO-2006106905 A1 | 10/2006 |
| WO | WO 2007/028110 A2 | 3/2007 |
| WO | WO 2007/070671 A2 | 6/2007 |
| WO | WO 2007/143689 A2 | 12/2007 |
| WO | WO 2007/145840 A2 | 12/2007 |
| WO | WO-2007147901 A1 | 12/2007 |
| WO | WO-2008042236 A2 | 4/2008 |
| WO | WO 2008/060705 A2 | 5/2008 |
| WO | WO 2008/070042 A2 | 6/2008 |
| WO | WO 2008/076379 A2 | 6/2008 |
| WO | WO 2008/079326 A2 | 7/2008 |
| WO | WO 2008/091222 A1 | 7/2008 |
| WO | WO 2008/139202 A1 | 11/2008 |
| WO | WO 2009/075565 A1 | 6/2009 |
| WO | WO 2009/085209 A2 | 7/2009 |
| WO | WO-2009080251 A1 | 7/2009 |
| WO | WO-2009089004 A1 | 7/2009 |
| WO | WO-2010054010 A1 | 5/2010 |

(56) References Cited

FOREIGN PATENT DOCUMENTS

| WO | WO-2010124009 A2 | 10/2010 |
|---|---|---|
| WO | WO-2010129304 A2 | 11/2010 |
| WO | WO-2011039370 A1 | 4/2011 |
| WO | WO-2011047383 A1 | 4/2011 |
| WO | WO-2011047442 A1 | 4/2011 |
| WO | WO-2011109298 A2 | 9/2011 |
| WO | WO-2012068098 A1 | 5/2012 |
| WO | WO-2013012747 A1 | 1/2013 |
| WO | WO-2013044215 A1 | 3/2013 |
| WO | WO-2014012007 A2 | 1/2014 |

OTHER PUBLICATIONS

Brorson et al. (J. Immunol. 163:6694-6701 (1999)).*
Burks et al. (PNAS 94:412-417 (1997)).*
Chen et al (1999. J Mol Biol. 293: 865-881).*
Holm et al (2007. Mol Immunology. 44: 1075-1084).*
Jang et al. (Molec. Immunol. 35:1207-1217 (1998)).*
Kobayashi et al. (Protein Engineering 12:879-844 (1999)).*
MacCallum et al (1996. J Mol Biol. 262: 732-745).*
Wu et al (1999. J Mol Biol. 294: 151-162).*
Beviglia et al. Anti-DLL4 treatment inhibits melanoma tumor growth, recurrence, metastases, and reduces frequency of cancer stem cells in a clinically relevant tumor model in NOD/SCID mice. Cancer Res 71(8 Suppl): Abstract 2834, 2011.*
Gray-Schopfer et al. The role of B-RAF in melanoma. Cancer Metast Rev 24: 165-183, 2005.*
Shields et al. Lack of extracellular signal-related kinase mitogen-activated protein kinase signaling shows a new type of melanoma. Cancer Res 67(4): 1502-1512, 2007.*
Beachy, P.A., et al., "Tissue repair and stem cell renewal in carcinogenesis," *Nature* 432:324-331, Nature Publishing Group, England (2004).
Bellavia, D., et al., "Constitutive activation of NF-κB and T-cell leukemia/lymphoma in Notch3 transgenic mice," *EMBO J.* 19:3337-3348, European Molecular Biology Organization, England (2000).
Bonnet, D. and Dick, J.E., "Human acute myeloid leukemia is organized as a hierarchy that originates from a primitive hematopoietic cell," *Nat. Med.* 3:730-737, Nature Publishing Company, United States (1997).
Brennan, K. and Brown, A.M.C., "Is there a role for Notch signalling in human breast cancer?," *Breast Cancer Res.* 5:69-75, BioMed Central Ltd, England (2003).
Ellisen, L.W., et al., "TAN-1, the Human Homolog of the *Drosophila* Notch Gene, Is Broken by Chromosomal Translocations in T Lymphoblastic Neoplasms," *Cell* 66:649-661, Cell Press, United States (1991).
Hope, K.J., et al., "Acute myeloid leukemia originates from a hierarchy of leukemic stem cell classes that differ in self-renewal capacity," *Nat. Immunol.* 5:738-743, Nature America Inc., United States (2004).
Iso, T., et al., "Notch Signaling in Vascular Development," *Arterioscler. Thromb. Vasc. Biol.* 23:543-553, Lippincott Williams & Wilkins, United States (2003).
Jhappan, C., et al., "Expression of an activated Notch-related int-3 transgene interferes with cell differentiation and induces neoplastic transformation in mammary and salivary glands," *Genes Dev.* 6:345-355, Cold Spring Harbor Laboratory Press, United States (1992).
Kopper, L. and Hajdú, M., "Tumor Stem Cells," *Pathol. Oncol. Res.* 10:69-73, Arányi Lajos Foundation, Netherlands (2004).
Krebs, L.T., et al., "Notch signaling is essential for vascular morphogenesis in mice," *Genes Dev.* 14:1343-1352, Cold Spring Harbor Laboratory Press, United States (2000).
Lapidot, T., et al., "A cell initiating human acute myeloid leukaemia after transplantation into SCID mice," *Nature* 367:645-648, Nature Publishing Group, England (1994).

Leethanakul, C., et al., "Distinct pattern of expression of differentiation and growth-related genes in squamous cell carcinomas of the head and neck revealed by the use of laser capture microdissection and cDNA arrays," *Oncogene* 19:3220-3224, Macmillan Publishers Ltd., England (2000).
Morrison, S.J., et al., "Regulatory Mechanisms in Stem Cell Biology," *Cell* 88:287-298, Cell Press, United States (1997).
Noguera-Troise, I., et al., "Blockade of Dll4 inhibits tumour growth by promoting non-productive angiogenesis," *Nature* 444:1032-1037, Nature Publishing Group, England (2006).
Parr, C., et al., "The possible correlation of Notch-1 and Notch-2 with clinical outcome and tumour clinicopathological parameters in human breast cancer," *Int. J. Mol. Med.* 14:779-786, D.A. Spandidos, Greece (2004).
Pear, W.S., et al., "Exclusive Development of T cell Neoplasms in Mice Transplanted with Bone Marrow Expressing Activated Notch Alleles," *J. Exp. Med.* 183:2283-2291, Rockefeller University Press, United States (1996).
Pear, W.S. and Aster, J.C., "T cell acute lymphoblastic leukemia/lymphoma: a human cancer commonly associated with aberrant NOTCH1 signaling," *Curr. Opin. Hematol.* 11:426-433, Lippincott Williams & Wilkins, United States (2004).
Politi, K., et al., "Notch in mammary gland development and breast cancer," *Semin. Cancer Biol.* 14:341-347, Elsevier Ltd., England (2004).
Purow, B.W., et al., "Expression of Notch-1 and Its Ligands, Delta-Like-1 and Jagged-1, Is Critical for Glioma Cell Survival and Proliferation," *Cancer Res.* 65:2353-2363, American Association for cancer Research, United States (2005).
Rae, F.K., et al., "Novel Association of a Diverse Range of Genes with Renal Cell Carcinoma as Identified by Differential Display," *Int. J. Cancer* 88:726-732, Wiley-Liss, Inc., United States (2000).
Ridgway., J., et al., "Inhibition of Dll4 signaling inhibits tumour growth by deregulating angiogenesis," *Nature* 444:1083-1087, Nature Publishing Group, England (2006).
Robey, E., et al., "An Activated Form of Notch Influences the Choice between CD4 and CD8 T Cell Lineages," *Cell* 87:483-492, Cell Press, United States (1996).
Shutter, J.R., et al., "Dll4, a novel Notch ligand expressed in arterial endothelium," *Genes Dev.* 14:1313-1318, Cold Spring Harbor Laboratory Press, United States (2000).
Smith, G.H., et al., "Constitutive Expression of a Truncated INT3 Gene in Mouse Mammary Epithelium Impairs Differentiation and Functional Development," *Cell Growth Differ.* 6:563-577, The American Association for Cancer Research, United States (1995).
Soriano, J.V., et al., "Expression of an Activated Notch4(int-3) Oncoprotein Disrupts Morphogenesis and Induces an Invasive Phenotype in Mammary Epithelial Cells In Vitro," *Int. J. Cancer* 86:652-659, Wiley-Liss, Inc., United States (2000).
Suzuki, T., et al., "Imbalanced expression of TAN-1 and human Notch4 in endometrial cancers," *Int. J. Oncol.* 17:1131-1139, D.A. Spandidos, Greece (2000).
Thurston, G., et al., "The Delta paradox: DLL4 blockade leads to more tumour vessels but less tumour growth," *Nat. Rev. Can.* 7:327-331, Nature Publishing Group, England (2007).
Uyttendaele, H., et al., "Notch4 and Wnt-1 Proteins Function to Regulate Branching Morphogenesis of Mammary Epithelial Cells in an Opposing Fashion," *Dev. Biol.* 196:204-217, Academic Press, United States (1998).
Van Es, J.H., and Clevers, H., "Notch and Wnt inhibitors as potential new drugs for intestinal neoplastic disease," *Trends Mol. Med.* 11:496-502, Elsevier Ltd., England (2005).
Van Limpt, V., et al., "SAGE Analysis of Neuroblastoma Reveals a High Expression of the Human Homologue of the *Drosophila* Delta Gene," *Med. Pediatr. Oncol.* 35:554-558, Wiley-Liss, Inc., United States (2000).
Weijzen, S., et al., "Activation of Notch-1 signaling maintains the neoplastic phenotype in human Ras-transformed cells," *Nat. Med.* 8:979-986, Nature Publishing Company, United States (2002).
Yan, X.-Q., et al., "A novel Notch ligand, Dll4, induces T-cell leukemia/lymphoma when overexpressed in mice by retroviral-mediated gene transfer," *Blood* 98:3793-3799, the American Society of Hematology, United States (2001).

(56) References Cited

OTHER PUBLICATIONS

Zagouras, P., et al., "Alterations in Notch signaling in neoplastic lesions of the human cervix," *PNAS* 92:6414-6418, National Academy of Sciences, United States (1995).

Fleming, R.J. et al., "The NOTCH receptor and its ligands," *Trends Cell Biol.* 7:437-441, Elsevier Science Ltd., England (1997).

Dorsch, M., et al., "Ectopic expression of Delta4 impairs hematopoietic development and leads to lymphoproliferative disease," *Blood* 100:2046-2055, The American Society of Hematology, United States (2002).

Dando, J., et al., "Notch/Delta4 Interaction in Human Embryonic Liver CD34$^+$ CD38$^-$ Cells: Positive influence on BFU-E Production in LTC-IC Potential Maintenance," *Stem Cells* 23:550-560, AlphaMed Press, United States (2005).

Williams, C.K., et al., "Up-regulation of the Notch ligand Delta-like 4 inhibits VEGF-induced endothelial cell function," *Blood* 107:931-939, American Society of Hematology, United States (2006).

Lauret, E. et al., "Membrane-bound Delta-4 Notch ligand reduces the proliferative activity of primitive human hematopoietic CD34$'$ CD38$^{low}$ cells while maintaining their LTC-IC potential," *Leukemia* 18:788-797, Nature Publishing Group, England (2004).

Sugimoto, A. et al., "Delta-4 Notch ligand promotes erythroid differentiation of human umbilical cord blood CD34$^+$ cells," *Exp. Hematol.* 34:424-432, Elsevier Inc., Netherlands (2006).

Liu, Z-J., et al., "Inhibition of endothelial cell proliferation by Notch1 signaling is mediated by repressing MAPK and P13K/Akt pathways and requires MAML1," *FASEB J.* 20:1009-1011, Federation of American Societies for Experimental Biology, United States (2006).

Hainaud, P., et al., "The Role of the Vascular Endothelial Growth Factor-Delta-like 4 Ligand/Notch4-Ephrin B2 Cascade in Tumor Vessel Remodeling and Endothelial Cell Functions," *Cancer Res.* 66:8501-8510, American Association for Cancer Research, United States (2006).

Duarte, A., et al., "Dosage-sensitive requirement for mouse Dll4 in artery development," *Genes Dev.* 18:2474-2478, Cold Spring Harbor Laboratory Press, United States (2004).

Fung, E., et al., "Delta-Like 4 Induces Notch Signaling in Macrophages: Implications for Inflammation," *Circulation* 115:2948-2956, American Heart Association, Inc., United States (2007).

Gale, N.W., et al., "Haploinsufficiency of delta-like 4 ligand results in embryonic lethality due to major defects in arterial and vascular development," *Proc. Natl. Acad. Sci.* 101:15949-15954, National Academy of Sciences, United States (2004).

Garber, K., "Notch Emerges as New Cancer Drug Target," *J. Natl. Cancer Inst.* 99:1284-1285, Oxford University Press, United States (2007).

Gridley, T., "Notch signaling in vascular development and physiology," *Development* 134:2709-2718, Company of Biologists Ltd., England (2007).

Harrington, L.S., et al., "Regulation of multiple angiogenic pathways by Dll4 and Notch in human umbilical vein endothelial cells," *Microvasc. Res.* 75:144-154, Elsevier Inc., United States (2008).

Hellström, M., et al., "Dll4 signalling through Notch1 regulates formation of tip cells during angiogenesis," *Nature* 445:776-780, Nature Publishing Group, England (2007).

Henning, K., et al., "mNotch1 signaling and erythropoietin cooperate in erythroid differentiation of multipotent progenitor cells and upregulate β-globin," *Exp. Hematol.* 35:1321-1332, Elsevier Inc., Netherlands (2007).

Ishiko, E., et al., "Notch Signals Inhibit the Development of Erythroid/Megakaryocytic Cells by Suppressing GATA-1 Activity through the Induction of HES1," *J. Biol. Chem.* 280:4929-4939, The American Society for Biochemistry and Molecular Biology, Inc., United States (2005).

Jarriault, S., et al., "Signalling downstream of activated mammalian Notch," *Nature* 377:355-358, Nature Publishing Group, England (1995).

Krebs, L.T., et al., "Haploinsufficient lethality and formation of arteriovenous malformations in Notch pathway mutants," *Genes Dev.* 18:2469-2473, Cold Spring Harbor Laboratory Press, United States (2004).

Mailhos, C., et al., "Delta4, an endothelial specific Notch ligand expressed at sites of physiological and tumor angiogenesis," *Differentiation* 69:135-144, Blackwell Wissenschafts-Verlag, England (2001).

Mazella, J., et al., "Expression of Delta-Like Protein 4 in the Human Endometrium," *Endocrinology* 149:15-19, The Endocrine Society, United States (2008).

Parks, A.L., et al., "Structure-Function Analysis of Delta Trafficking, Receptor Binding and Signaling in Drosophila," *Genetics* 174:1947-1961, the Genetics Society of America, United States (2006).

Patel, N.S., et al., "Up-regulation of Delta-like 4 Ligand in Human Tumor Vasculature and the Role of Basal Expression in Endothelial Cell Function," *Cancer Res.* 65:8690-8697, American Association for Cancer Research, United States (2005).

Rao, P.K., et al., "Isolation and Characterization of the Notch Ligand Delta4," *Exp. Cell Res.* 260:379-386, Academic Press, United States (2000).

Scehnet, J.S., et al., "Inhibition of Dll4-mediated signaling induces proliferation of immature vessels and results in poor tissue perfusion," *Blood* 109:4753-4760, The American Society of Hematology, United States (2007).

Wilson, A. and Radtke, F., "Multiple functions of Notch signaling in self-renewing organs and cancer," *FEBS Lett.* 580:2860-2868, Elsevier B.V., Netherlands (2006).

Besseyrias, V., et al., "Hierarchy of Notch-Delta interactions promoting T cell lineage commitment and maturation," *J. Exp. Med.* 204:331-343, The Rockefeller University Press, United States (2007).

Engin, F., et al., "Dimorphic effects of Notch signaling in bone homeostasis," *Nat. Med.* 14:299-305, Nature Publishing Company, United States (2007).

Siekmann, A.F. and Lawson, N.D., "Notch signalling limits angiogenic cell behaviour in developing zebrafish arteries," *Nature* 445:781-784, Nature Publishing Group, England (2007).

Phng, L.-K., et al., "Nrarp Coordinates Endothelial Notch and Wnt Signaling to Control Vessel Density in Angiogenesis," *Dev. Cell* 16:70-82, Elsevier Inc., United States (2009).

Sainson, R.C.A. and Harris, A.L., "Anti-Dll4 therapy: can we block tumour growth by increasing angiogenesis?," *Trends Mol. Med.* 13:389-395, Elsevier Ltd., England (2007).

Hoey, T., et al., "DLL4 Blockade Inhibits Tumor Growth and Reduces Tumor-Initiating Cell Frequency," *Cell Stem Cell* 5:168-177, Elsevier Inc., United States (2009).

Li, J.-L. and Harris, A.L., "Notch signaling from tumor cells: A new mechanism of angiogenesis," *Cancer Cell* 8:1-3, Cell Press, United States (2005).

Shawber, C.J., et al., "Notch Signaling in Primary Endothelial Cells," *Ann. N.Y. Acad. Sci.* 995:162-170, New York Academy of Sciences, United States (2003).

Bray, S.J., "Notch signalling: a simple pathway becomes complex," *Nat. Rev. Mol. Cell Biol.* 7:678-689, Nature Publishing Group, England (2006).

Farnie, G., et al., "Novel Cell Culture Technique for Primary Ductal Carcinoma In Situ: Role of Notch and Epidermal Growth Factor Receptor Signaling Pathways," *J. Natl. Cancer Inst.* 99:616-627, Oxford University Press, United States (2007).

Liu, Z.-J., et al., "Regulation of Notch1 and Dll4 by Vascular Endothelial Growth Factor in Arterial Endothelial Cells: Implications for Modulating Arteriogenesis and Angiogenesis," *Mol. Cell Biol.* 23:14-25, American Society for Microbiology, United States (2003).

Liu, S., et al., "Mammary stem cells, self-renewal pathways, and carcinogenesis," *Breast Cancer Res.* 7:86-95, BioMed Central Ltd., England (2005).

Dontu, G., et al., "Role of Notch signaling in cell-fate determination of human mammary stem/progenitor cells," *Breast Cancer Res.* 6:R605-R615, BioMed Central Ltd., England (2004).

(56) References Cited

OTHER PUBLICATIONS

Farnie, G. and Clarke, R.B., "Mammary Stem Cells and Breast Cancer—Role of Notch Signalling," *Stem Cell Rev.* 3:169-175, Humana Press Inc., United States (2007).
Miele, L. and Osborne, B., "Arbiter of Differentiation and Death: Notch Signaling Meets Apoptosis," *J. Cell Physiol.* 181:393-409, Wiley-Liss, Inc., United States (1999).
Miele, L., "Notch Signaling," *Clin. Cancer Res.* 12:1074-1077, American Association for Cancer Research, United States (2006).
Hofmann, J.J. and Iruela-Arispe, M.L., "Notch Signaling in Blood Vessels: Who Is Talking to Whom About What?," *Circ. Res.* 100:1556-1568 American Heart Association, Inc., United States (2007).
Limbourg, A., et al., Notch Ligand Delta-Like 1 Is Essential for Postnatal Arteriogenesis, *Circ. Res.* 100:363-371, American Heart Association, Inc., United States (2007).
Lobov, I.B., et al., Delta-like ligand 4 (Dll4) is induced by VEGF as a negative regulator of angiogenic sprouting, *Proc. Natl. Acad. Sci.* 104:3219-3224, National Academy of Sciences, United States (2007).
Clarke, M.F., et al., "Cancer Stem Cells—Perspectives on Current Status and Future Directions: AACR Workshop on Cancer Stem Cells," *Cancer Res.* 66:9339-9344, American Association for Cancer Research, United States (2006).
Milano, J., at al., Modulation of Notch Processing by γ-Secretase Inhibitors Causes Intestinal Goblet Cell Metaplasia and Induction of Genes Known to Specify Gut Secretory Lineage Differentiation, *Toxicol. Sci* 82:341-358, Society of Toxicology, United States (2004).
Reya, T., et al., "Stem cells, cancer, and cancer stem cells," *Nature* 414:105-111, Nature Publishing Company, England (2001).
Tax, F.E., et al., "Sequence of *C. elegans* lag-2 reveals a cell-signalling domain shared with Delta and Serrate of *Drosophila*," *Nature* 368:150-154, Nature Publishing Group, England (1994).
Wang, J.C.Y., et al., "Primitive Human Hematopoeitic Cells Are Enriched in Cord Blood Compared with Adult Bone Marrow or Mobilized Peripheral Blood as Measured by the Quantitative In Vivo SCID-Repopulating Cell Assay," *Blood* 89:3919-3924, American Society of Hematology, United States (1997).
Weng, A.P., et al., "Activating Mutations of NOTCH1 in Human T Cell Acute Lymphoblastic Leukemia," *Science* 306:269-271, American Association for the Advancement of Science, United States (2004).
Yen, W.-C., et al., "Targeting Cancer Stem Cells and Vasculature by a Novel Anti-Dll4 Antibody Inhibits Pancreatic Tumor Growth and Delays Tumor Recurrence," presented at the 100th Annual Meeting of the American Association for Cancer Research in Denver, Colorado, on Apr. 18-22, 2009, 1 page.
Office Action mailed Dec. 26, 2008 in U.S. Appl. No. 11/607,780, Clarke, M.F. et al., filed Dec. 1, 2006.
Office Action mailed Jan. 2, 2009 in U.S. Appl. No. 11/607,780, Clarke, M.F. et al., filed Dec. 1, 2006.
Response to Office Action mailed Jan. 2, 2009, sent electronically on Jul. 2, 2009, in U.S. Appl. No. 11/607,780, Clarke, M.F. et al., filed Dec. 1, 2006.
Allenspach, E.J. et al., "Notch Signaling in Cancer," *Cancer Biol. Ther.* 1:466-476, Landes Bioscience, United States (2002).
Artavanis-Tsakonas, S., et al., "Notch Signaling: Cell Fate Control and Signal Integration in Development," *Science* 284:770-776. American Association for the Advancement of Science, United States (1999).
Axelson, H., "Notch signaling and cancer: emerging complexity," *Semin. Cancer Biol.* 14:317-319, Elsevier Ltd., England (2004).
Callahan, R. and Raafat, A., "Notch Signaling in Mammary Gland Tumorigenesis," *J. Mammary Gland Biol Neoplasia* 6:23-36, Plenum Publishing Corporation, United States (2001).
Fre, S. et al., "Notch signals control the fate of immature progenitor cells in the intestine," *Nature* 435:964-968, Nature Publishing Group, England (2005).

Han, W. et al., "A soluble form of human Delta-like-1 inhibits differentiation of hematopoietic progenitor cells," *Blood* 95:1616-1625, The American Society of Hematology, United States (2000).
Harper, J.A. et al., "Notch signaling in development and disease," *Clin. Genet.* 64:461-472, Munksgaard, Denmark (2003).
Hopfer, O. et al., "The Notch pathway in ovarian carcinomas and adenomas," *Br. J. Cancer* 93:709-718, Cancer Research UK, England (2005).
Janeway, C. et al., "Immunobiology: The Immune System in Health and Disease," Appendix L, pp. 579-581, Current Biology Publications, 4th Edition (1999).
Jeffries, S. and Capobianco, A.J., "Neoplastic Transformation by Notch Requires Nuclear Localization," *Mol. Cell Biol.* 20:3928-3941, American Society for Microbiology, United States (2000).
Morrison, S.J. et al., "Transient Notch Activation Initiates an Irreversible Switch from Neurogenesis to Gliogenesis by Neural Crest Stem Cells," *Cell* 101:499-510, Cell Press, United States (2000).
Nam, Y. et al., "Notch signaling as a therapeutic target," Curr. Opin. Chem. Biol. 6:501-509, Elsevier Science Ltd., England (2002).
Tannock, I. and Hill, R., "The Basic Science of Oncology," pp. 357-358, New York: McGraw-Hill (1998).
Thélu, J. et al., "Notch signalling is linked to epidermal cell differentiation level in basal cell carcinoma, psoriasis and wound healing," *BMC Dermatol.* 2:7, BioMed Central, England (2002).
Weng, A.P., et al., "Growth Suppression of Pre-T Acute Lymphoblastic Leukemia Cells by Inhibition of Notch Signaling," *Mol. Cell Biol.* 23:655-664, American Society for Microbiology, United States (2003).
Carter, P., "Improving the Efficacy of Antibody-Based Cancer Therapies," *Nat. Rev. Cancer* 1:118-129, Nature Publishing Group, England (2001).
Noguera, I., et al., "Expression of Delta-like 4 (Dll4) ligand in mouse tumor models," *Proceedings of the Annual Meeting of the American Association for Cancer Research* 46(Suppl. S):1104, American Association for Cancer Research, United States (2005).
Noguera, I., et al., "Delta-like ligand 4 (Dll4) is critical for tumor growth and angiogenesis," *Proceedings of the Annual Meeting of the American Association for Cancer Research* 47:1342, American Association for Cancer Research, United States (2006).
Xu, A., et al., "Regions of *Drosophila* Notch That Contribute to Ligand Binding and the Modulatory Influence of Fringe," *J. Biol. Chem.* 280:30158-30165, The American Society for Biochemistry and Molecular Biology, Inc., United States (2005).
Supplementary European Search Report issued in European Patent Application No. 07 83 8966, European Patent Office, Munich, Germany, mailed on Apr. 6, 2010.
Paul, William E., *Fundamental Immunology*, 3rd Edition, Chapter 8, p. 242, Raven Press, New York, United States (1993).
Gurney, A. and Hoey, T., "Anti-DLL4, a cancer therapeutic with multiple mechanisms of action," *Vasc. Cell* 3:18, BioMed Central, England (2011), 4 pages.
Smith et al., "A First-in-Human, Phase I Trial of the Anti-DLL4 Antibody (OMP-21M18) Targeting Cancer Stem Cells (CSCs) in Patients with Advanced Solid Tumors," http://www.oncomed.com/news/pr/study/posterfinalNov10.pdf, accessed Feb. 2, 2012, 1 page.
Yan, M., et al., "Chronic DLL4 blockade induces vascular neoplasms," *Nature* 463:E6-E7, Macmillan Publishers Limited, England (2010).
NCT00744562, "A Phase 1 Dose Escalation Study of OMP-21M18 in Subjects With Solid Tumors," ClinicalTrials.gov archive, accessed at http://clinicaltrials.gov/archive/NCT01189968/2010_10_28, accessed on Feb. 2, 2012, 4 pages.
NCT01189968, "A Phase 1b Study of Carboplatin and Permetrexed Plus OMP-21M18 as 1st-line Treatment in Subject With Non-Squamous Non-Small Cell Lung Cancer," ClinicalTrials.gov archive, accessed at http://clinicaltrials.gov/archive/NCT01189968/2010_10_28, accessed on Feb. 7, 2012, 4 pages.
International Search Report for International Patent Application No. PCT/US11/60773, International Searching Authority, Alexandria, Virginia, United States, mailed on Mar. 26, 2012.

(56) References Cited

OTHER PUBLICATIONS

Written Opinion of the International Searching Authority for International Patent Application No. PCT/US11/60773, International Searching Authority, Alexandria, Virginia, United States, mailed Mar. 26, 2012.
Co-pending U.S. Appl. No. 13/826,103, filed Mar. 14, 2013, inventors Gurney et al.
Co-pending U.S. Appl. No. 13/885,249, filed Nov. 15, 2011, inventors Stagg et al.
Brown et al. "Tolerance of single, but not multiple, amino acid replacements in antibody VH CDR 2: a means of minimizing B cell wastage from somatic hyper-mutation?" *J Immunol.* 156(9): 3285-3291 Williams & Wilkins, United States (1996).
Vajdos, F.F. et al., "Comprehensive functional maps of the antigen-binding site of an anti-ErbB2 antibody with shotgun scanning mutagenesis," *J Mol Biol* 320(2): 415-428 Academic Press, London (2002).
Paul, William E., *Fundamental Immunology*, 3$^{rd}$ Edition, Chapter 8, pp. 292-295, Raven Press, New York, United States (1993).
Rudikoff, S., et al., "Single amino acid substitution altering antigen-binding specificity," Proc. Natl. Acad. Sci. USA 79:1979-1983, National Academy of Sciences, United States (1982).
De-Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," *J. Immunol.* 169:3076-3084, The American Association of Immunologists, Inc., United States (2002).
Casset, F., et al., "A peptide mimetic of an anti-CD4 monoclonal antibody by rational design," *BBRC* 307:198-205, Elsevier Science, United States (2003).
Al-Hajj, M., et al., "Prospective Identification of Tumorigenic Breast Cancer Cells," Proceedings of the National Academy of Sciences 100(7):3983-3988, The National Academy of Sciences, United States (2003).
Barbas, C.F. 3RD., et al., "In vitro evolution of a neutralizing human antibody to human immunodeficiency virus type 1 to enhance affinity and broaden strain cross-reactivity," Proceedings of the National Academy of Sciences 91(9):3809-3813, National Academy of Sciences, United States (1994).
Benvenuti, S., et al., "Oncogenic activation of the RAS/RAF signaling pathway impairs the response of metastatic colorectal cancers to anti-epidermal growth factor receptor antibody therapies," Cancer Research 67(6):2643-2648, American Association for Cancer Research, United States (2007).
Beviglia, L., et al., "Anti-DLL4 reduces tumor growth and tumorigenicity in B-RAF V600E melanomas including those with acquired resistance to B-RAF inhibitors," AACR 103rd Annual Meeting Mar. 31-Apr. 4, 2012, Abstract LB-196, 1 page (2012).
Beviglia, L., et al., "In vivo evaluation of anti-tumor activity by an anti-VEGF and anti-DLL4 bispecific antibody in a humanized model of skin graft," AACR 104th Annual Meeting 2013, Abstract 4330, Apr. 6-10, 1 page (2013).
Bloom, J.W., et al., "Intrachain disulfide bond in the core hinge region of human IgG4," Protein Science 6(2):407-415, John Wiley & Sons, Inc., United States (1997).
Boerner, P., et al., "Production of antigen-specific human monoclonal antibodies from in vitro-primed human splenocytes," The Journal of Immunology 147(1):86-95, The American Association of Immunologists, Inc., United States (1991).
Brennan, M., et al., "Preparation of Bispecific Antibodies by Chemical Recombination of Monoclonal Immunoglobulin G.sub.1 Fragments," Science 229(4708):81-83, American Association for the Advancement of Science, United States (1985).
Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology 111(5Pt1):2129-2138, The Rockefeller University Press, United States (1990).

Chau, I. and Cunningham, D., "Treatment in advanced colorectal cancer: what, when and how?," British Journal of Cancer 100(11):1704-1719, Nature Publishing Group, United States (2009).
Chi, A.S., et al., "Angiogenesis as a Therapeutic Target in Malignant Gliomas," Oncologist 14(6):621-636, AlphaMed Press, United States (2009).
Chothia, C. and Lesk, A.M., "Canonical structures for the hypervariable regions of immunoglobulins," Journal of Molecular Biology 196(4):901-917, Elsevier Science, United States (1987).
Chothia, C., et al., "Domain association in immunoglobulin molecules. The packing of variable domains," Journal of Molecular Biology 186(3):651-663, Elsevier Science, England (1985).
Chowdhury, P.S. and Pastan, I., "Improving antibody affinity by mimicking somatic hypermutation in vitro," Nature Biotechnology 17(6):568-572, Nature Publishing Group, United States (1999).
Claxton, S. and Fruttiger, M., "Periodic Delta-like 4 expression in developing retinal arteries," Gene Expression Pattern 5:123-127, Elsevier B.V., Netherlands (2004).
Cole, S., et al., "The EBV-Hybridoma Technique and Its Application to Human Lung Cancer," Monoclonal Antibodies and Cancer Therapy, 77-96, Proceedings of the Roche-UCLA Symposium,United States (1985).
Colman, P.M., et al., "Effects of Amino Acid Sequence Changes on Antibody-Antigen Interactions," Research in Immunology 145(1):33-36, Elsevier, France (1994).
Co-pending U.S. Appl. No. 12/497,405 inventors Yan., et al., filed Jul. 2, 2009 (Not Published and Now Abandoned).
Co-Pending U.S. Appl. No. 14/498,602 inventors Stagg, R.J., et al., filed Sep. 26, 2014 (Not Published).
Cubillo, A., et al., "A Phase Ib study of demcizumab (DEM, anti-DLL4) with gemcitabine (GEM) in patients with first line locally advanced or metastatic pancreatic cancer," Proceedings of the AACR-NCI-EORTC International Conference on Molecular Targets and Cancer Therapeutics, Oct. 19-23, 2013, Abstract B78, 2 pages (2013).
Dalerba, P., et al., "Phenotypic characterization of human colorectal cancer stem cells," Proceedings of the National Academy of Sciences of the United States of America 104(24):10158-10294, National Academy of Sciences, United States (2007).
Deisenhofer, J., "Crystallographic refinement and atomic models of a human Fc fragment and its complex with fragment B of protein A from *Staphylococcus aureus* at 2.9- and 2.8-A resolution," Biochemistry 20(9):2361-2370, American Chemical Society, United States (1981).
Dixit, R., "Cardiovascular Safety of Biologics: Challenges and Opportunities," Medimmune, Safety Pharmacology Society, Annular Meeting Speakers Presentations (Oct. 3, 2012).
Dreher, M.L., et al., "Colony assays for antibody fragments expressed in bacteria," Journal of Immunological Methods 139(2):197-205, Elsevier Science, United States (1991).
Dupont, J. "Anti-Angiogenic Agents and Cardiovascular Effects: Implications for Clinical Development in Cancer," presentation given in Barcelona, Spain on Nov. 4, 2011, 16 pages.
English language translation of Oishi, H., et al., "Novel therapeutic strategy for pancreatic cancer targeting Notch signaling pathway," Proceedings of the Japanese Cancer Association 65:311-312, Japan (2006).
English language translation of "Tumor-angiogenesis suppression therapy targeting the Notch signaling pathway," Suizo (Pancreas) 21(3):249, Japan (2006).
Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).
European Search Report for EP Application No. EP10824244.7, Munich, Germany, mailed on Feb. 18, 2013, 6 pages.
Fischer, M., et al., "Anti-DLL4 Inhibits Growth and Reduces Tumor-Initiating Cell Frequency in Colorectal Tumors with Oncogenic KRAS Mutations," Cancer Research 71(5):1520-1525, American Association for Cancer Research, United States (2011).

(56) References Cited

OTHER PUBLICATIONS

Gagnon, M.L., et al., "Identification of a natural soluble neuropilin-1 that binds vascular endothelial growth factor: In vivo expression and antitumor activity," Proceedings of the National Academy of Sciences 97(6):2573-2578, National Academy of Sciences, United States (2000).

Gallahan, D., et al., "A new common integration region (int-3) for mouse mammary tumor virus on mouse chromosome 17," Journal of Virology 61(1):218-220, American Society for Microbiology, United States (1987).

Gallahan, D., et al., "Expression of a Truncated Int3 Gene in Developing Secretory Mammary Epithelium Specifically Retards Lobular Differentiation Resulting in Tumorigenesis," Cancer Research 56:1775-1785, American Association for Cancer Research, United States (1996).

Gracian, A.C., et al., "A phase 1b study of the anticancer stem cell agent demcizumab (DEM) and gemcitabine (GEM) with or without paclitaxel protein bound particles (nab-paclitaxel) in patients with pancreatic cancer," 2014 Gastrointestinal Cancers Symposium, Abstract 279, 2 pages (2014).

Gridley, T., "Notch Signaling During Vascular Development," Proceedings of the National Academy of Sciences 98(10):5377-5378, National Academy of Sciences, United States (2001).

Gronberg, B.H., et al., "Phase III Study by the Norwegian Lung Cancer Study Group: Pemetrexed Plus Carboplatin Compared with Gemcitabine Plus Carboplatin as First-line Chemotherapy in Advanced Non-small-cell Lung Cancer," Journal of Clinical Oncology 27(19):3217-3224, American Society of Clinical Oncology, United States (2009).

Gruber, M., et al., "Efficient Tumor Cell Lysis Mediated by a Bispecific Single Chain Antibody Expressed in *Escherichia coli*," The Journal of Immunology 152(11):5368-5374, The American Association of Immunologists, Inc., United States (1994).

Hallahan, A.R., et al., "The SmoA1 Mouse Model Reveals that Notch Signaling is Critical for the Growth and Survival of Sonic Hedgehog-Induced Medulloblastomas," Cancer Research 64(21):7794-7800, American Association for Cancer Research, United States (2004).

Harlow, E. and Lane, D., eds., "Immunoassays," in Antibodies: A Laboratory Manual, 14:553-612, Cold Spring Harbor Laboratory, United States (1988).

Harris, W.J., "Production of Humanized Monoclonal Antibodies for in vivo Imaging and Therapy," Biochemical Society Transactions 23(4):1035-1038, Portland Press on the Behalf of the Biochemical Society, England (1995).

Hawkins, R.E., et al., "Selection of phage antibodies by binding affinity. Mimicking affinity maturation," Journal of Molecular Biology 226(3):889-896, Elsevier Science, United States (1992).

Hermentin, P. and Seiler, F.R., "Investigations with Monoclonal Antibody Drug (Anthracycline) Conjugates," Behring Institute Research Communications 82:197-215, Behringwerke Ag, Germany (1988).

Hidalgo, M., et al., "A Phase 1b Study of the Anti-Cancer Stem Cell Agent Demcizumab (DEM, anti-DLL4) and Gemcitabine (GEM) with or without Nab-Paclitaxvel in Patients with Pancreatic Cancer," European Society for Medical Oncology 2014 Congress, Sep. 17 and Sep. 28, Poster 616PD, 1 page (2014).

Holash, J., et al., "Inhibitors of growth factor receptors, signaling pathways and angiogenesis as therapeutic molecular agents," Cancer Metastasis Rev 25:243-252, Dordrecht, Netherlands (2006).

Holash, J., et al., "VEGF-Trap: A VEGF Blocker with Potent Antitumor Effects," Proceedings of the National Academy of Sciences USA 99(17):11393-11398, National Academy of Sciences, United States (2002).

Hoogenboom, H.R. and Winter, G., "By-Passing Immunisation. Human Antibodies from Synthetic Repertoires of Germline VH Gene Segments Rearranged in Vitro," Journal of Molecular Biology 227(2):381-388, Elsevier Science, United States (1992).

Humphreys, D.P., et al., "Formation of dimeric Fabs in *Escherichia coli*: effect of hinge size and isotype, presence of interchain disulphide bond, Fab' expression levels, tail piece sequences and growth conditions," Journal of Immunological Methods 209(2):193-202, Elsevier Science, Netherlands (1997).

Hurle, M.R. and Gross, M., "Protein engineering techniques for antibody humanization," Current Opinion in Biotechnology 5(4):428-433, (1994).

Hwang, K.J., et al., "Hepatic uptake and degradation of unilamellar sphingomyelin/cholesterol liposomes: a kinetic study," Proceedings of the National Academy of Sciences 77(7):4030-4034, National Academy of Sciences, United States (1980).

International Preliminary Report on Patentability and Written Opinion for International Application No. PCT/US2010/53064, International Searching Authority, mailed on Feb. 14, 2011, 7 pages.

International Preliminary Report on Patentability for International Application No. PCT/US2013/065015, The International Bureau of WIPO, Switzerland, mailed on Apr. 22, 2014, 17 pages.

International Search Report for International Application No. PCT/US2010/53064, mailed on Feb. 14, 2011, 3 Pages.

International Search Report for International Patent Application No. PCT/US2007/020889, United States Patent and Trademark Office, United States, mailed on Apr. 9, 2008, 5 pages.

International Search Report with the Written Opinion of the International Searching Authority for International application No. PCT/US10/32625, United States Patent and Trademark Office, United States, mailed on Dec. 17, 2010, 11 pages.

International Search Report with the Written Opinion of the International Searching Authority for International application No. PCT/US12/56886, United States Patent and Trademark Office, United States, mailed on Feb. 28, 2013, 8 pages.

International Search Report with Written Opinion for International Application No. PCT/US2010/58511, International Searching Authority, United States, mailed on Mar. 3, 2011, 9 pages.

Izzedine, H., et al., "Management of Hypertension in Angiogenesis Inhibitor-Treated Patients," Annals of Oncology 20(5):807-815, Oxford University Press, England (2009).

Jackson, J.R., et al., "In vitro antibody maturation. Improvement of a high affinity, neutralizing antibody against IL-1 beta," The Journal of Immunology 154(7):3310-3319, The American Association of Immunologists, Inc., United States (1995).

Jimeno, A., et al., "Phase 1 study of REGN421 (R)/SAR153192, a fully-human delta-like ligand 4 (Dll4) monoclonal antibody (mAb), in patients with advanced solid tumors," ASCO University 2013 ASCO Annual Meeting accessed at http://meetinglibrary.asco.org/content/113836-132, 2 pages.

Jones, P.T., et al., "Replacing the Complementarity-Determining Regions in a Human Antibody with those from a Mouse," Nature 321(6069):522-525, Nature Publishing Group, England (1986).

Kim, E.S., et al., "Potent VEGF blockade causes regression of coopted vessels in a model of neuroblastoma," Proceedings of the National Academy of Sciences 99(17):11399-11404, National Academy of Sciences, United States (2002).

Kingsman, A.J., et al., "Replication in *Saccharomyces cerevisiae* of Plasmid pBR313 Carrying DNA from the Yeast Trpl Region," Gene 7(2):141-152, Elsevier/North-Holland Biomedical Press, Netherlands (1979).

Kostelny, S.A., et al., "Formation of a Bispecific Antibody by the Use of Leucine Zippers," The Journal of Immunology 148(5):1547-1553, American Association of Immunologists, United States (1992).

Kuo, C.J., et al., "Comparative evaluation of the antitumor activity of antiangiogenic proteins delivered by gene transfer," Proceedings of the National Academy of Sciences 98(8):4605-4610, National Academy of Sciences, United States (2001).

Lazar, E., et al., "Transforming Growth Factor α: Mutation of Aspartic Acid 47 and Leucine 48 Results in Different Biological Activities," Molecular and Cellular Biology 8(3):1247-1252, American Society for Microbiology, United States (1988).

Lee, H.S., et al., "Generation and characterization of a novel single-gene-encoded single-chain immunoglobulin molecule with antigen binding activity and effector functions," Molecular Immunology 36(1):61-71, Elsevier Science Ltd., Netherlands (1999).

(56) References Cited

OTHER PUBLICATIONS

Leong, K.G. and Karsan, A., "Recent Insights into the Role of Notch Signaling in Tumorigenesis," Blood 107(6):2223-2233, The American Society of Hematology, United States (2006).

Li, X., et al., "Notch3 Signaling is Required for the Development of Pulmonary Arterial Hypertension," Nature Medicine 15(11):1289-1297, Nature Publishing Company, United States (2009).

Liu, Z.J., et al., "Inhibition of endothelial cell proliferation by Notch 1 signaling is mediated by repressing MAPK and PI4K/Akt pathways and requires MAML1" Federation of American Societies for Experimental Biology 20:E201-E210, American Society for Experimental Biology, United States (2006).

Lu, K.V., and Bergers, G., "Mechanisms of evasive resistance to anti-Vegf therapy in glioblastoma," CNS Oncology 2(1):49-65, Future Medicine, Inc., United States (2013).

Luca, V.C., et al., "Structural basis for Notch1 engagement of Delta-like 4," Science, 347(6224):847-853, American Association for the Advancement of Science, United States (2015).

Maeda, H., et al., "Construction of Reshaped Human Antibodies with HIV-Neutralizing Activity," Human Antibodies and Hybridomas 2(3):124-134, Butterworth-Heinemann, United Kingdom (1991).

Marks, J.D., et al., "By-Passing Immunization: Building High Affinity Human Antibodies by Chain Shuffling," Biotechnology 10(7):779-783, Nature Publishing Company, United States (1992).

Marks, J.D., et al., "By-passing immunization Human Antibodies from V-Gene Libraries Displayed on Phage," Journal of Molecular Biology 222(3)1581-597, Academic Press Limited, United States (1991).

McKeage, M., et al., "A Phase Ib study of demcizumab (DEM, anti-DLL4) plus pemetrexed and carboplatin in patients with first line stage IIIb/IV non-squamous non-small cell lung cancer," Proceedings of the AACR-NCI-EORTC International Conference on Molecular Targets and Cancer Therapeutics, Oct. 19-23, 2013, Abstract A71, 2 pages (2013).

McKeage, M.J., et al., "A phase Ib study of the anticancer stem cell agent demcizumab (DEM), pemetrexed (PEM), and carboplatin (CARBO) in pts with first-line nonsquamous NSCLC," 2014 ASCO Annual Meeting, Abstract 2544, 2 pages (2014).

Merchant, A.M., et al., "An efficient route to human bispecific IgG," Nature Biotechnology 16(7):677-681, Nature Publishing Group, United States (1998).

Milstein, C., et al., "Hybrid hybridomas and their use in immunohistochemistry," Nature 305(5934): 537-540, Macmillan Magazines Ltd, London (1983).

Morimoto, K., et al., "Single-step purification of F(ab)2 fragments of mouse monoclonal antibodies (immunoglobulins G1) by hydrophobic interaction high performance liquid chromatography using TSKgel Phenyl-5PW," Journal of Biochemical and Biophysical Methods 24:107-117, Elsevier Science Publishers B.V., Netherlands (1993).

Morrison, S.J., et al., "Hematopoietic Stem Cells: Challenges to Expectations," Current Opinion in Immunology 9(2):216-221, Elsevier Science, United States (1997).

Morrison, S.J.,et al., "The Biology of Hematopoietic Stem Cells," Annual Review of Cell and Developmental Biology 11:35-71, Annual Reviews, United States (1995).

Morrison, S.L., et al., "Chimeric Human Antibody Molecules: Mouse Antigen-Binding Domains with Human Constant Region Domains," Proceedings of the National Academy of Sciences USA 81(21):6851-6855, National Academy of Sciences, United States (1984).

Nickoloff, B.J., et al., "Notch Signaling as a Therapeutic Target in Cancer: a New Approach to the Development of Cell Fate Modifying Agents," Oncogene 22(42):6598-6608, Nature Publishing Group, England (2003).

Nohaile, M.J., et al., "Altering dimerization specificity by changes in surface electrostatics," Proceedings of the National Academy of Sciences 98(6):3109-3114, National Academy of Sciences, United States (2001).

Novotný, J. and Haber, E., "Structural invariants of antigen binding: comparison of immunoglobin VL-VH and VL-VL domain dimers," Proceedings of the National Academy of Sciences 82(14):4592-4596, National Academy of Sciences, United States (1985).

Yen, W-C., et al., "The combination of gemcitabine/nab-paclitaxel and anti-DLL4 (demcizumab) produces synergistic growth inhibition, delays tumor recurrence and reduces tumor initiating cells in pancreatic cancer," American Association for Cancer Research Annual Meeting 2014, Abstract 1898, 1 page (2014).

Office Action mailed Apr. 16, 2013, in U.S. Appl. No. 13/229,006, Hoey, T.C. et al., filed Sep. 9, 2011.

Oishi, H., et al., "Novel therapeutic strategy for pancreatic cancer targeting Notch signaling pathway," Proceedings of the Japanese Cancer Association 65:311-312, (2006).

OncoMed Pharmaceuticals, Press Release, "Clinical Cancer Research Publishes OncoMed Data Demonstrating Anti-Cancer Activity for Anti-DLL4 (Demcizumab) in Pancreatic Cancer," Sep. 6, 2012, 2 pages.

OncoMed Pharmaceuticals, Press Release, "OncoMed Announces Abstracts Accepted at the 2014 ASCO Annual Meeting," Apr. 23, 2014, 2 pages.

OncoMed Pharmaceuticals, Press Release, "OncoMed Anti-Cancer Stem Cell Antibody OMP-21M18 Demonstrates Potent Activity in Preclinical Studies Against Human Colon Cancer Tumors Regardless of KRAS Mutation Status," Mar. 1, 2011, 3 pages.

OncoMed Pharmaceuticals, Press Release, "OncoMed's Demcizumab Phase 1b Clinical Trials Show Encouraging Safety and Anti-Tumor Activity at ESMO," Sep. 28, 2014, 3 pages.

OncoMed Pharmaceuticals, Press Release, "OncoMed Pharmaceuticals Announces Presentations of Anti-Notch2/3 and Demcizumab Clinical Data at EORTC-NCI-AACR Meeting," Nov. 9, 2012, 3 pages.

OncoMed Pharmaceuticals, Press Release, "OncoMed Pharmaceuticals Initiates Phase 1b/2 Clinical Trial of Demcizuman (Anti-DLL4) in Combination with Paclitaxel in Ovarian Cancer," Sep. 19, 2013, 3 pages.

OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.

OncoMed Pharmaceuticals, Press Release, "OncoMed Pharmaceuticals Presents Data From Demcizumab Phase 1b Clinical Study in Pancreatic Cancer at the 2014 Gastrointestinal Cancers Symposium," Jan. 17, 2014, 3 pages.

OncoMed Pharmaceuticals Press Release, "OncoMed Pharmaceuticals Recaps New Data Presented at AACR," Apr. 3, 2012, 2 pages.

OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.

OncoMed Pharmaceuticals Press Release, "OncoMed Pharmaceuticals to Present Data from Two Clinical Programs in Advanced Pancreatic Cancer at the 2014 Gastrointestinal Cancers Symposium," Jan. 9, 2014, 2 pages.

OncoMed Pharmaceuticals, Press Release, "OncoMed Pharmaceuticals Updates Phase 1b Data for Demcizumab With Pemetrexed and Carboplatin in Patients With First-Line Stage IIIb/IV Non-Small Cell Lung Cancer at the AACR-NCO-EORTC International Conference on Molecular Targets and Cancer Therapeutics in Boston, Oct. 19-23, 2013," Oct. 20, 2013, 3 pages.

OncoMed Pharmaceuticals, Press Release, "OncoMed Presents Data on Multiple Anti-Cancer Stem Cell Programs at American Association for Cancer Research Annual Meeting," Apr. 8, 2014, 4 pages.

OncoMed Pharmaceuticals Press Release, "OncoMed Presents New Clinical and Biomarker Data From Its Tarextumab and Demcizumab Clinical Trials at the EORTC-NCI-AACR Symposium," Nov. 21, 2014, 3 pages.

(56) References Cited

OTHER PUBLICATIONS

OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed to Present Clinical and Preclinical Data at the 26th EORTC-NCI-AACR Symposium on Molecular Targets and Cancer Therapeutics Meeting," Oct. 30, 2014, 2 pages.
OncoMed Pharmaceuticals Press Release, "OncoMed to Present Data From Three Clinical Studies at the 2014 ASCO Annual Meeting," May 14, 2014, 4 pages.
OncoMed Pharmaceuticals Press Release, "OncoMed to Present New and Emerging Data from Demcizumab (anti-DLL4, OMP-21M18) and Tarextumab (anti-Notch2/3, OMP-59R5) Clinical Studies at the European Society for Medical Oncology 2014 Congress," Sep. 17, 2014, 2 pages.
OncoMed Pharmaceuticals Press Release, "OncoMed To Present New Data in Six Anti-Cancer Stem Cell Programs at AACR," Apr. 2, 2013, 2 pages.
Pisano, C., et al., "Undersulfated, low-molecular-weight glycol-split heparin as an antiangiogenic VEGF antagonist," Glycobiology 15(2):1C-6C, Oxford University Press, England (2005).
Portolano, S., et al., "Lack of Promiscuity in Autoantigen-Specific H and L Chain Combinations as Revealed by Human H and L Chain 'roulette'," The Journal of Immunology 150(3):880-887, The American Association of Immunologists, Inc., United States (1993).
Presta, L.G., et al., "Humanization of an antibody directed against IgE," The Journal of Immunology 151(5):2623-2632, The American Association of Immunologists, Inc., United States (1993).
Rehman, A.O and Wang, C-U, "Notch signaling in the regulation of tumor angiogenesis," Trends in Cell Biology 16(6):293-300, Elsevier Ltd., England (2006).
Riechmann, L., et al., "Reshaping Human Antibodies for Therapy," Nature 332(6162):323-329, Nature Publishing Group, United States (1988).
Sal-Man, N. and Shai, Y., "Arginine mutations within a transmembrane domain of Tar, an *Escherichia coli* aspartate receptor, can drive homodimer dissociation and heterodimer association in vivo," Biochem. J. 385(Pt1):29-36, Portland Press, United Kingdom (2005).
Schier, R., et al., "Identification of function and structural amino-acid residues by parsimonious mutagenesis," Gene 169(2):147-155, Elsevier Science B.V., Netherlands (1996).
Shalaby, M.R., et al., "Development of Humanized Bispecific Antibodies Reactive with Cytotoxic Lymphocytes and Tumor Cells Overexpressing the HER2 Protooncogene," The Journal of Experimental Medicine 175(1): 217-225, The Rockefeller University Press, United States (1992).
Sheets, M.D., et al., "Efficient Construction of a Large Nonimmune Phage Antibody Library: The Production of High-affinity Human Single-chain Antibodies to Protein Antigens," Proceedings of the National Academy of Sciences 95(11)6157-6162, The National Academy of Sciences, Unites States (1998).
Sica, D.A., "Angiogenesis Inhibitors and Hypertension," US Cardiovascular Disease 79-80, Touch Briefings, United States (2007).
Siena, S., et al., "Biomarkers predicting clinical outcome of epidermal growth factor receptor-targeted therapy in metastatic colorectal cancer," Journal of the National Cancer Institute 101(19):1308-1324, Oxford University Press, England (2009).
Sims, M.J., et al., "A humanized CD18 antibody can block function without cell destruction," The Journal of Immunology 151(4):2296-2308, The American Association of Immunologists, United States (1993).
Skolnick, "From Genes to Protein Stucture and Function: Novel Applications of Computational Approaches in the Genomic Era," Trends in Biotechnology 18:34-39, Elsevier Science Publishers, London (2000).
Stinchcomb, D.T., et al., "Isolation and Characterisation of a Yeast Chromosomal Replicator," Nature 282(5734):39-43, Nature Publishing Group, England (1979).
Sullivan, D.C. and Bicknell, R., "New molecular pathways in angiogenesis," British Journal of Cancer 89:228-231, Cancer Research UK, United Kingdom (2003).
Suresh, M.R., et al., "Bispecific Monoclonal Antibodies from Hybrid Hybridomas," Methods in Enzymology 121:210-228, Academic Press Inc., United States (1986).
Tavares, M.J., et al., "Inhibition of Vascular Endothelium by the Notch-Ligand Delta-4 Unveils a Novel Therapeutic Target," Abstract#1944, Poster Board Session: 115-11, Blood 102(11):3 pages, American Society of Hematology, United States (2003).
Thurston, G., and Gale, N.W., "Vascular Endothelial Growth Factor and Other Signaling Pathways in Developmental and Pathologic Angiogenesis," International Journal of Hematology 80:7-20, The Japanese Society of Hematology, Japan (2004).
Ton, N.C. and Jayson, G.C., "Resistance to Anti-VEGF Agents," Current Pharmaceutical Design 10:51-64, Bentham Science Publishers Ltd., Netherlands (2004).
Traunecker, A., et al., "Bispecific single chain molecules (Janusins) target cytotoxic lymphocytes on HIV infected cells," The EMBO Journal 10(12):3655-3659, Oxford University Press, United Kingdom (1991).
Tutt, A., et al., "Trispecific F(ab')3 Derivatives that use Cooperative Signaling Via the TCR/CD3 Complex and CD2 to Activate and Redirect Resting Cytotoxic T Cells," The Journal of Immunology 147: 60-69, The American Association of Immunologists, United States (1991).
Unknown Author, "Tumor angiogenesis suppression therapy targeting the Notch signaling pathway," Suizo (Pancreas) 21(3):249, (2006).
Urlaub, G. and Chasin, L.A., "Isolation of Chinese hamster cell mutants deficient in dihydrofolate reductase activity," Proceedings of the National Academy of Sciences 77(7):4216-4220, National Academy of Sciences, United States (1980).
Vaswani, S.K. and Hamilton, R.G., "Humanized antibodies as potential therapeutic drugs," Annals of Allergy, Asthma & Immunology 81(2):105-115, American College of Allergy, Asthma, & Immunology, United States (1998).
Vaughan, T.J., et al., "Human Antibodies with Sub-nanomolar Affinities Isolated from a Large non-Immunized Phage Display Library," Nature Biotechnology 14(3):309-314, Nature Publishing Co., United States (1996).
Verhoeyen, M., et al., "Reshaping human antibodies: grafting an antilysozyme activity," Science 239(4847):1534-1536, American Association for the Advancement of Science, United States (1988).
Ward, E.S., "Antibody engineering using *Escherichia coli* as host," Advances in Pharmacology 24:1-20, Academic Press, United States (1993).
Wong, O.K., et al., "Voreloxin (formerly SNS-595) is a potent DNA intercalator and topoisomerase II poison that induces cell cycle dependent DNA damage and rapid apoptosis in cancer cell lines," 24th EORTC-NCI-AACR Symposium, Nov. 9, Poster 169, 1 page (2012).
Written Opinion of the International Searching Authority for International application No. PCT/US2007/020889, United States Patent and Trademark Office, United States, mailed on Apr. 9, 2008, 4 pages.
Wu, C., et al., "Simultaneous targeting of multiple disease mediators by a dual-variable-domain immunoglobulin," Nature Biotechnology 25(11):1290-1297, Nature Publishing Co., United States (2007).
Yelton, D.E., "Affinity maturation of the BR96 anti-carcinoma antibody by codon-based mutagenesis," The Journal of Immunology 155(4):1994-2004, The American Association of Immunologists, United States (1995).
Yen, W-C., et al., "Anti-DLL4 (demcizumab) inhibits tumor growth and reduces cancer stem cell frequency in patient-derived ovarian cancer xenografts," AACR 104th Annual Meeting 2013, Abstract 3725, Apr. 6-10, 1 page (2013).
Yen, W.C., et al., "Anti-DLL4 has broad spectrum activity in pancreatic cancer dependent on targeting DLL4-Notch signaling in both tumor and vasculature cells," Clinical Cancer Research 18(19):5374-5386, American Association for Cancer Research, United States (2012).

(56) References Cited

OTHER PUBLICATIONS

Yen, W-C., et al., "Dual targeting of DLL4 and VEGF signaling by a novel bispecific antibody inhibits tumor growth and reduces cancer stem cell frequency," AACR Annual Meeting 2014, Apr. 5-9, 2014, Abstract 207, 1 page (2014).
Yen, W-C., et al., "Targeting cancer stem cells by an anti-DLL4 antibody inhibits epithelial-to-mesenchymal transition, delays tumor recurrence and overcomes drug resistance in breast and pancreatic cancer," AACR 103rd Annual Meeting 2012, Mar. 31-Apr. 4, Abstract 3357, 1 page (2013).
European Opposition Brief for European Patent No. 2157192 filed May 8, 2014, 46 pages.
Reply to European Opposition Brief for European Patent No. 2157192 filed Jan. 8, 2015, 42 pages.
Response to European Opposition Brief Reply for European Patent No. 2157192, filed May 14, 2015, 14 pages.
Chen, J-Z., et al., "Cloning and identification of a cDNA that encodes a novel human protein with thrombospondin type I repeat domain, hPWTSR," Mol. Biol. Rep. 29:287-292, Kluwer Academic Publishers, Netherlands (2002).
Perantoni, A.O., "Renal Development: Perspectives on a Wnt-Dependent Process," Seminars in Cells and Development Biology Abstract, 1 page, Academic Press, United Kingdom (2003).
Stump, R.J., et al., "A Role for Wnt/Beta-Catenin Signaling in Lens Epithelial Differentiation," Developmental Biology Abstract, 1 page, Elsevier Inc., United States (2003).
Polakis, P., "Wnt signaling and cancer," Genes & Development 14:1837-1851, Cold Spring Harbor Laboratory Press, United States (2000).
Horesh, Y., et al., "A Rapid Method for Detection of Putative RNAi Target Genes in Genomic Data," Bioinformatics 19(Suppl 2):ii73-ii80, Oxford University Press, England (2003).
Jackson, A.L. and Linsley, P.S., "Noise Amidst the Silence: Off-Target siRNAs?," Trends in Genetics 20( 11 ):521-524, Elsevier Science Publishers B.V., Netherlands (2004).
Goldblum, S.E., et al., "Thrombospondin-1 Induces Tyrosine Phosphorylation of Adherens Junction Proteins and Regulates an Endothelial Paracellular Pathway," Molecular Biology of the Cell 10(5):1537-1551, The American Society for Cell Biology, United States (1999).
Lonberg, N., "Human Antibodies from Transgenic Animals," Nature Biotechnology 23(9): 1117-1125, Nature Publishing Group, United Kingdom (2005).
Easwaran, V., et al., "Beta-Catenin Regulates Vascular Endothelial Growth Factor Expression in Colon Cancer," Cancer Research 63(12):3145-3153, American Association for Cancer Research, United States (2003).
Wu, W., et al., "Mutual Antagonism between Dickkopf1 and Dickkopf2 Regulates Wnt/Beta-Catenin Signalling," Current Biology 10(24):1611-1614, Elsevier Science Ltd., England (2000).
Polesskaya, A., et al., "Wnt Signaling Induces the Myogenic Specification of Resident CD45+ Adult Stem Cells during Muscle Regeneration," Cell Abstract, 1 page, MIT Press, United States (2003).
Meniel, V. and Clarke, A.R., "Wnt-Cadherin Connections in Normal and Neoplastic Mammary Epithelium," Journal of Mammary Gland Biology and Neoplasia 8(4):435-447, Kluwer Academic/Plenum Publishers, United States (2003).
Hartmann, C., "Wnt-Signaling and Skeletogenesis," Journal of Musculoskeletal & Neuronal Interactions 2(3):274-276, International Society of Musculoskeletal and Neuronal Interactions, Greece (2002).
Smalley, M.J. and Dale, T.C., "Wnt Signalling in Mammalian Development and Cancer," Cancer and Metastasis Reviews 18(2):215-230, Kluwer Academic Publishers, Netherlands (1999).
Bienz, M. and Clevers, H., "Linking Colorectal Cancer to Wnt Signaling," Cell 103(2):311-320, Cell Press, United States (2000).
Korinek, V., et al., "Constitutive Transcriptional Activation by a Beta-Catenin-Tcf Complex in APC -/- Colon Carcinoma," Science 275(5307):1784-1787, American Association for the Advancement of Science, United States (1997).

Fischer, L., et al., "Wnt-3A Enhances Bone Morphogenetic Protein-2-Mediated Chondrogenesis of Murine C3H10T1/2 Mesenchymal Cells," The Journal of Biological Chemistry 277(34):30870-30878, JBC Papers in Press, American Society for Biochemistry and Molecular Biology, United States (2002).
Boyden, L.M., et al., "High Bone Density Due to a Mutation in LDL-Receptor-Related Protein 5," The New England Journal of Medicine 346(20):1513-1521, Massachusetts Medical Society, United States (2002).
Gong, Y., et al., "LDL Receptor-Related Protein 5 (LRP5) Affects Bone Accrual and Eye Development," Cell 107(4):513-523, Cell Press, United States (2001).
Surendran, K., et al, "A Role for Wnt-4 in Renal Fibrosis," American Journal of Physiology. Renal Physiology 282(3):F431-F441, American Physiological Society, United Sates (2002).
Saadi-Kheddouci, S., et al., "Early Development of Polycystic Kidney Disease in Transgenic Mice Expressing an Activated Mutant of the Beta-Catenin Gene," Oncogene 20(42):5972-5981, Nature Publishing Group, England (2001).
Fujino, T., et al., "Low-Density Lipoprotein Receptor-Related Protein 5 (LRP5) is Essential for Normal Cholesterol Metabolism and Glucose-Induced Insulin Secretion," Proceedings of the National Academy of Sciences 100(1):229-234, National Academy of Sciences, United States (2003).
UniProt "Thrombospondin-1," identifying No. P07996-TSP1_HUMAN, accessed at http://www.uniprot.org/uniprot/P07996, accessed on Sep. 25, 2014, 14 pages.
Kazanskaya, O., et al., "R-Spondin2 is a Secreted activator of Wnt/β-Catenin Signaling and is required for Xenopus Myogenesis," Devel. Cell 7:525-534, Cell Press, United States (2004).
Amado, R.G., et al., "Wild-Type KRAS is Required for Panitumumab Efficacy in Patients with Metastatic Colorectal Cancer," Journal of Clinical Oncology 26(10):1626-1634, American Society of Clinical Oncology, United States (2008).
Chartier, C., et al., "The Hippo Signaling Pathway Mediates BMP Inhibition of Cancer Stem Cells," 2015 AACR Annual meeting, Apr. 18-22, Abstract 2322, 1 page (2015).
Cubillo, A., et al., "A Ph1b Study of Demcizumab (DEM, anti-DLL4) with Gemcitabine (GEM) in Patients with 1st Line Locally Advanced or Metastatic Pancreatic Cancer," AACR-NCI-EORTC International Conference on Molecular Targets and Cancer Therapeutics, Oct. 19-23, 2013, Poster (2013), 8 pages.
Deonarain, M.P., et al., "Antibodies Targeting Cancer Stem Cells: A New Paradigm in Immunotherapy?," mAbs 1(1):12-25,Taylor & Francis, United States (2009).
Dupont, J., et al., "A Phase 1 b Study of Anti-DLL4 (Delta-Like Ligand 4) Antibody Demcizumab (DEM) with Pemetrexed (PEM) and Carboplatin (CARBO) in Patients with 1st-Line Non-Squamous NSCLC," 2015 European Lung Cancer Conference (ELCC), Geneva, Switzerland, Apr. 15-18, Abstract 114, 2 pages (2015).
Hidalgo, M., et al., "A Phase 1 b Study of the Anti-Cancer Stem Cell Agent Demcizumab (DEM, Anti-DLL4) and Gemcitabine (GEM) with or without Paclitaxel Protein Bound Particles (Nab-Paclitaxel) in pts with Pancreatic Cancer," 2015 ASCO Annual Meeting, Abstract 4118, 3 pages (2015).
Hidalgo, M., et al., "Pre-Clinical and Clinical Activity of Anti-DLL4 (Demcizumab) in Combination with Gemcitabine Plus nab-Paclitaxel in Pancreatic Cancer," 26th EORTC-NCI-AACR Symposium on Molecular Targets and Cancer Therapeutics Preclinical Models Poster Session, Abstract 166, 2 pages (Nov. 2014).
Hurwitz, H.I., et al., "Phase I Trial of Pazopanib in Patients with Advanced Cancer," Clinical Cancer Research 15(12):4220-4227, American Association for Cancer Research, United States (2009).
Lenihan, D.J., "How is cardiac toxicity defined and what impact does this have on cancer outcome or drug development," PowerPoint Presentation from the DIA Meeting, 42 slides (2011).
Lievre, A., et al., "KRAS Mutation Status Is Predictive of Response to Cetuximab Therapy in Colorectal Cancer," Cancer Research 66(8):3992-3995, American Association for Cancer Research, United States (2006).
McKeage, M., et al., "A Phase 1b Study of Demcizumab plus Pemetrexed and Carboplatin in Patients with 1st line Non-Squamous Non-Small Cell Lung Cancer (NSCLC)," 24th EORTC-

(56) References Cited

OTHER PUBLICATIONS

NCI-AACR Symposium on Molecular Targets and Cancer Therapeutics, Nov. 6-9, 2012, Poster (2012), 9 pages.
McKeage, M., et al., "Phase 1b Study of Demcizumab plus Pemetrexed and Carboplatin in Patients with 1st line Non-Small Cell Lung Cancer (NSCLC)," AACR-NCI-EORTC International Conference on Molecular Targets and Cancer Therapeutics, Oct. 19-23, 2013, Poster (2013), 8 pages.
McKeage, M.J., et al., "A Phase 1b Study of the Anti-Cancer Stem Cell Agent Demcizumab (DEM), Pemetrexed (PEM) and Carboplatin (CARBO) inPatients with 1st Line Non-Squamous Non-Small Cell Lung Cancer (NSCLC)," 2015 ASCO Annual Meeting, Abstract 8045, 2 pages (2015).
NCT01189929, "A Phase 1b Study of Gemcitabine Plus OMP-21M18 as 1st-line Treatment in Subjects With Locally Advanced or Metastatic Pancreatic Cancer" as updated on Aug. 26, 2010, ClinicalTrials.gov archive, accessed at https://clinicaltrials.gov/archives/NCT01189929/2010_08_26, accessed on Apr. 20, 2015, 5 pages.
NCT01189929, "A Phase 1b Study of Gemcitabine Plus OMP-21M18 as 1st-line Treatment in Subjects With Locally Advanced or Metastatic Pancreatic Cancer" as updated on Dec. 15, 2011, ClinicalTrials.gov archive, accessed at https://clinicaltrials.gov/archives/NCT01189929/2011_12_15, accessed on Apr. 20, 2015, 5 pages.
NCT01189968, "A Phase 1b Study of Carboplatin and Pemetrexed Plus OMP-21M18 as 1st-line Treatment in Subjects with Non-Squamous Non-Small Cell Lung Cancer" as updated on Aug. 26, 2010, ClinicalTrials.gov archive, accessed at https://clinicaltrials.gov/archive/NCT01189968/2010_08_26, accessed on Apr. 20, 2015, 5 pages.
NCT01189968, "A Phase 1b Study of Carboplatin and Pemetrexed Plus OMP-21M18 as 1st-line Treatment in Subjects with Non-Squamous Non-Small Cell Lung Cancer" as updated on Dec. 15, 2011, ClinicalTrials.gov archive, accessed at https://clinicaltrials.gov/archive/NCT01189968/2011_12_15, accessed on Apr. 20, 2015, 5 pages.
OncoMed Pharmaceuticals Press Release, "OncoMed and Lilly Enter Clinical Supply Agreement to Evaluate the Combination of Demcizumab and Alimta(R) (pemetrexed for injection) in Lung Cancer," Apr. 2, 2015, 4 pages.
OncoMed Pharmaceuticals Press Release, "OncoMed Announces Abstracts Accepted for Presentation at the 2015 ASCO Annual Meeting," Apr. 21, 2015, 2 pages.
OncoMed Pharmaceuticals Press Release, "OncoMed Doses First Patient in Phase 1 Clinical Trial of Novel Anti-DLL4/VEGF Bispecific Antibody," Jan. 5, 2015, 2 pages.
OncoMed Pharmaceuticals Press Release, "OncoMed Highlights Immuno-Oncology Discoveries During 2015 Research & Development Day," Apr. 29, 2015, 3 pages.
OncoMed Pharmaceuticals Press Release, "OncoMed Initiates Dosing in Phase 2 Clinical Trial of Demcizumab for the Treatment of Non-Small Cell Lung Cancer," Feb. 4, 2015, 3 pages.
OncoMed Pharmaceuticals Press Release, "OncoMed Initiates Dosing in Randomized Phase 2 Clinical Trial of Demcizumab in Pancreatic Cancer Patients," Apr. 22, 2015, 3 pages.
OncoMed Pharmaceuticals Press Release, "OncoMed Pharmaceuticals to Review Key ASCO Data for Demcizumab and Tarextumab During Conference Call on Tuesday, Jun. 2, 2015," May 28, 2015, 2 pages.
OncoMed Pharmaceuticals Press Release, "OncoMed Presents Data From Phase 1b Trial of Demcizumab in Pancreatic Cancer at the 2015 ASCO Annual Meeting," Jun. 1, 2015, 3 pages.
OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.
OncoMed Pharmaceuticals Press Release, "OncoMed Presents Demcizumab Data From Phase 1b Clinical Trial in Non-Small Cell Lung Cancer Patients at the European Lung Cancer Conference," Apr. 16, 2015, 3 pages.
OncoMed Pharmaceuticals Press Release, "OncoMed Presents Updated Demcizumab Data in Non-Small Cell Lung Cancer at the 2015 ASCO Annual Meeting," Jun. 1, 2015, 3 pages.
OncoMed Pharmaceuticals Press Release, "OncoMed to Present Clinical Data for Demcizumab at the European Lung Cancer Conference," Apr. 9, 2015, 2 pages.
Schmidt, C., "Drug Makers Chase Cancer Stem Cells," Nature Biotechnology 26(4):366-367, Nature Publishing Group, United States (2008).
Smith, D.C., et al., "A Phase I Dose Escalation and Expansion Study of the Anticancer Stem Cell Agent Demcizumab (Anti-DLL4) in Patients with Previously Treated Solid Tumors," Clinical Cancer Research 20(24):6295-6303, American Association for Cancer Research, United States (2014).
Srivastava, M., et al., "Dual Targeting of Delta-Like Ligand 4 (DLL4) and Programmed Death 1 (PD1) Inhibits Tumor Growth and Generates Enhanced Long-Term Immunological Memory," 2015 AACR Annual Meeting, Apr. 19, Abstract 255, 1 page (2015).
Takeda, T. and Kohno, M., "Brain Natriuretic Peptide in Hypertension," Hypertension Research 18(4):259-266, Nature Publishing Group, England (1995).
Yan, Wei., "Design and Engineering of Fc Heterodimers for the Production of Bispecific Antibodies," Symposium Abstract, Keystone Symposia on Molecular and Cellular Biology, Accelerating Life Science Discovery, Mar. 27-Apr. 1, 2009, Whistler, British Columbia.
Yan, Wei, "The Design and Engineering of Fc Heterodimers for the Production of Bispecific Antibodies and Other Heterodimer Fusion Proteins," Symposium Abstract, 20th Annual International Conference, Antibody Engineering, Antibody Engineering and Immunotherapeutics for the 21st Century, Dec. 6-10, 2009, San Diego, California.
Yan, Wei, "The Design and Engineering of Fc Heterodimers for the Production of Bispecific Antibodies," Symposium Abstract, Eleventh Annual Phage Display of Antibodies and Peptides, Approaches for 2nd Generation Biologics, Apr. 6-Apr. 7, 2009, Boston, Massachusetts.
Yen, W., et al., "Targeting Cancer Stem Cells and Vasculature by a Novel Anti-Delta-Like 4 Ligand (DLL4) Antibody for Treatment of Triple Negative Breast Cancer," Cancer Research 69(Suppl. )(24):788s-789s, Abstract 5071, American Association for Cancer Research, United Sates (2009).
Yoneya, T., et al., "Molecular Cloning of Delta-4, a New Mouse and Human Notch Ligand," Journal of Biochemistry 129(1):27-34, Japanese Biochemical Society, Japan (2001).

* cited by examiner

Brain

Lung

Intestine

Liver

* $p<0.0001$, vs. Control

METHODS FOR TREATING MELANOMA

CROSS-REFERENCE TO RELATED APPLICATIONS

This application is a continuation of U.S. patent application Ser. No. 13/229,006, filed Sep. 9, 2011, now U.S. Pat. No. 8,551,479, which claims the priority benefit of U.S. Provisional Application No. 61/381,628, filed Sep. 10, 2010, both of which are hereby incorporated by referenced herein in their entirety.

FIELD OF THE INVENTION

The field of this invention generally relates to antibodies and other agents that bind to DLL4 proteins, as well as methods of using the antibodies or other agents for the treatment of diseases, such as cancer, particularly melanoma.

BACKGROUND OF THE INVENTION

Skin cancer is the most common of all cancers and melanoma is the most serious and aggressive type of skin cancer. Melanoma accounts for less than 5% of skin cancer cases, yet it is responsible for a large majority of the deaths associated with skin cancer. Almost 70,000 people in the United States will be diagnosed with melanoma during 2010 and approximately 9,000 people are expected to die from the disease (American Cancer Society; www.cancer.org). Across the world the incidence of melanoma has been increasing at an alarming rate, with a lifetime risk of developing melanoma as high as 1/58 for males in the U.S. to 1/25 for males in Australia (Jemal et al., 2008, *CA: Cancer J. Clin.* 58:71-96). The survival rate is fairly high for individuals who are diagnosed with early stage melanoma and receive appropriate treatment. However, metastatic melanoma remains one of the most difficult cancers to treat and individuals with this advanced form have an average survival time of only nine to eleven months.

Signaling pathways normally connect extracellular signals to the nucleus leading to expression of genes that directly or indirectly control cell growth, differentiation, survival and death. In melanoma as well as a wide variety of cancers, signaling pathways are dysregulated and may be linked to tumor initiation and/or progression. Signaling pathways implicated in human oncogenesis include, but are not limited to, the Notch pathway, the Ras-Raf-MEK-ERK or MAPK pathway, the PI3K-AKT pathway, the CDKN2A/CDK4 pathway, the Bcl-2/TP53 pathway, and the Wnt pathway.

The Notch signaling pathway is a universally conserved signal transduction system. It is involved in cell fate determination during development including embryonic pattern formation and post-embryonic tissue maintenance. In addition, Notch signaling has been identified as a critical factor in the maintenance of hematopoietic stem cells (HSCs).

The Notch pathway has been linked to the pathogenesis of both hematologic and solid tumors and cancers. Numerous cellular functions and microenvironmental cues associated with tumorigenesis have been shown to be modulated by Notch pathway signaling, including cell proliferation, apoptosis, adhesion, and angiogenesis. (Leong et al., 2006, *Blood*, 107:2223-2233). In addition, Notch receptors and/or Notch ligands have been shown to play potential oncogenic roles in a number of human cancers, including acute myelogenous leukemia, B cell chronic lymphocytic leukemia, Hodgkin lymphoma, multiple myeloma, T cell acute lymphoblastic leukemia, brain cancer, breast cancer, cervical cancer, colon cancer, lung cancer, pancreatic cancer, prostate cancer, skin cancer and melanoma. (Leong et al., 2006, *Blood*, 107:2223-2233; Nickoloff et al., 2003, *Oncogene*, 22:6598-6608). Thus, the Notch pathway has been identified as a potential target for cancer therapy.

Previous studies demonstrated that antibodies to the human Notch ligand Delta-like ligand 4 (DLL4) can decrease the percentage of cancer stem cells or tumor initiating cells in some xenograft tumors. In addition, antibodies to mouse DLL4 were shown to result in hyperproliferation of tumor vasculature. (Hoeg et al., 2009, *Cell Stem Cell*, 5:168-177). These findings suggest that targeting the Notch pathway, for example with DLL4 antagonists, could help eliminate not only the majority of non-tumorigenic cancer cells, but the tumorigenic cancer stem cells responsible for the formation and recurrence of solid tumors.

The MAPK (mitogen-activated protein kinase) pathway has been shown to play key roles in various normal physiological processes such as cellular metabolism, cell cycle progression, cell death and neurological function. Mutations in the MAPK pathway have been shown to be very important in melanoma development in that up to 90% of melanomas and benign melanocytic neoplasms carry activating mutations in either B-raf or N-ras. In addition, it has been reported that 30-70% of malignant melanomas contain B-raf mutations and that a valine to glutamate change at position 600 accounts for approximately 80% of the mutations. (Davies et al., 2002, *Nature*, 417:949-954). These findings suggested that the MAPK pathway could be a potential target for new therapies for treatment of melanoma.

Numerous efforts to develop therapeutic agents that specifically target the mutated B-raf kinase are currently underway. However, these agents will have little or no effect in patients with a wild-type B-raf. In fact, patients without the V600E B-raf mutation have been excluded from on-going clinical trials. Thus, there is a need for new agents that could provide therapeutic benefit for this segment of melanoma patients.

As of 2010, there are only two FDA-approved drugs for metastatic melanoma, dacarbazine and interferon-alpha. However, only 10-20% of patients with advanced melanoma respond to either of these drugs. Furthermore, no new drug for treatment of melanoma has been approved in over fifteen years. Clearly, there is a need for new and/or more effective therapeutic agents for the treatment of melanoma and particularly metastatic melanoma.

SUMMARY OF THE INVENTION

The present invention provides methods of inhibiting growth of a melanoma tumor comprising administering a therapeutically effective amount of a DLL4 antagonist to a human subject. In some embodiments, the DLL4 antagonist is an antibody that specifically binds the extracellular domain of human DLL4. In some embodiments, the DLL4 antagonist is an antibody that specifically binds an epitope within amino acids 27-217 of the extracellular domain of human DLL4. In certain embodiments, the antibody binds an epitope comprising amino acids 66-73 of human DLL4. In certain embodiments, the antibody binds an epitope comprising amino acids 139-146 of human DLL4. In certain embodiments, the antibody binds an epitope comprising amino acids 66-73 and 139-146 of human DLL4.

In another aspect, the invention provides methods of treating melanoma comprising administering a therapeutically effective amount of a DLL4 antagonist to a human subject. In some embodiments, the DLL4 antagonist is an antibody that specifically binds the extracellular domain of human DLL4. In some embodiments, the DLL4 antagonist is an antibody that specifically binds an epitope within amino acids 27-217 of the extracellular domain of human DLL4. In certain embodiments, the antibody binds an epitope comprising amino acids 66-73 of human DLL4. In certain embodiments, the antibody binds an epitope comprising amino acids 139-146 of human DLL4. In certain embodiments, the antibody binds an epitope comprising amino acids 66-73 and 139-146 of human DLL4.

In another aspect, the invention provides methods of treating melanoma and/or inhibiting growth of a melanoma tumor in a human subject, comprising (a) determining if the subject has a melanoma comprising a mutation in the MAPK pathway, and (b) administering to the subject a therapeutically effective amount of a DLL4 antagonist. In some embodiments, the MAPK pathway comprises a wild-type B-raf. In some embodiments, the MAPK pathway comprises a B-raf mutation. In some embodiments, the MAPK pathway comprises a Ras mutation. In some embodiments, the MAPK pathway comprises a wild-type Ras.

In another aspect, the invention provides methods of treating a human subject, comprising (a) determining if the subject has a melanoma that comprises a wild-type B-raf or a B-raf mutation, and (b) administering to the subject a therapeutically effective amount of a DLL4 antagonist. In some embodiments, the melanoma comprises a wild-type B-raf. In some embodiments, the melanoma comprises a B-raf mutation.

In another aspect, the invention provides methods of treating melanoma and/or inhibiting growth of a melanoma tumor in a human subject, comprising (a) selecting a subject for treatment based on, at least in part, if the subject has a melanoma that comprises a mutation in the MAPK pathway, and (b) administering to the subject a therapeutically effective amount of a DLL4 antagonist. In some embodiments, the MAPK pathway comprises a wild-type B-raf. In some embodiments, the MAPK pathway comprises a B-raf mutation. In some embodiments, the MAPK pathway comprises a Ras mutation. In some embodiments, the MAPK pathway comprises a wild-type Ras.

In another aspect, the invention provides methods of treating a human subject, comprising (a) selecting a subject for treatment based on, at least in part, on the subject having a melanoma that comprises a wild-type B-raf or a B-raf mutation, and (b) administering to the subject a therapeutically effective amount of a DLL4 antagonist. In some embodiments, the melanoma comprises a wild-type B-raf. In some embodiments, the melanoma comprises a B-raf mutation.

In another aspect, the invention provides methods of treating melanoma in a human subject, comprising (a) identifying if a subject has a melanoma comprising a mutation in the MAPK pathway, and (b) administering to the subject a therapeutically effective amount of a DLL4 antagonist. In some embodiments, the MAPK pathway comprises a wild-type B-raf. In some embodiments, the MAPK pathway comprises a B-raf mutation. In some embodiments, the MAPK pathway comprises a Ras mutation. In some embodiments, the MAPK pathway comprises a wild-type Ras.

In another aspect, the invention provides methods of treating a human subject, comprising (a) identifying if the subject has a melanoma that comprises a wild-type B-raf or a B-raf mutation, and (b) administering to the subject a therapeutically effective amount of a DLL4 antagonist. In some embodiments, the melanoma comprises a wild-type B-raf. In some embodiments, the melanoma comprises a B-raf mutation.

In another aspect, the invention provides methods of treating melanoma in a human subject, comprising (a) determining that the subject's melanoma is substantially non-responsive to at least one B-raf inhibitor, and (b) administering to the subject a therapeutically effective amount of a DLL4 antagonist. In some embodiments, the melanoma that is substantially non-responsive to at least one B-raf inhibitor comprises a wild-type B-raf.

In another aspect, the invention provides methods of selecting a human subject for treatment with a DLL4 antagonist, comprising determining if the subject has (a) a melanoma comprising a wild-type B-raf, or (b) a melanoma that is substantially non-responsive to at least one B-raf inhibitor, wherein if the subject has (a) and/or (b), the subject is selected for treatment with a DLL4 antagonist.

In certain embodiments of each of the aforementioned aspects, as well as other aspects and embodiments described elsewhere herein, a mutation (or lack thereof) in the MAPK pathway is detected in a sample by methods known to those skilled in the art, such as PCR-based assays or direct nucleotide sequencing. In some embodiments, the mutation is a B-raf mutation. In some embodiments, the mutation is a Ras mutation. In some embodiments, the sample is a fresh sample, a frozen sample, or a formalin-fixed paraffin-embedded sample.

In certain embodiments of each of the aforementioned aspects, as well as other aspects and embodiments described elsewhere herein, the mutation in the MAPK pathway is a B-raf mutation. In some embodiments, the B-raf mutation is an activating mutation. In some embodiments, the melanoma comprises more than one B-raf mutation. In some embodiments, the melanoma comprises mutations in other protein kinases. In some embodiments, the B-raf mutation is a mutation in amino acid 600. In some embodiments, the B-raf mutation is a valine to glutamate mutation at amino acid 600 (B-raf$^{V600E}$). In some embodiments, the B-raf mutation is a valine to lysine mutation at amino acid 600 (B-raf$^{V600K}$).

In certain embodiments of each of the aforementioned aspects, as well as other aspects and embodiments described elsewhere herein, the melanoma is a primary tumor. In some embodiments, the melanoma is metastatic melanoma. In some embodiments, the melanoma is a cutaneous tumor. In some embodiments, the melanoma is an extracutaneous tumor.

In certain embodiments of each of the aforementioned aspects, as well as other aspects and embodiments described elsewhere herein, the DLL4 antagonist is an antibody that specifically binds human DLL4. In some embodiments, the antibody specifically binds an epitope within amino acids 27-217 of the extracellular domain of human DLL4 (SEQ ID NO:14).

In some embodiments, the DLL4 antagonist is an antibody comprising: (a) a heavy chain CDR1 comprising TAYYIH (SEQ ID NO:1), a heavy chain CDR2 comprising YISCYNGATNYNQKFKG (SEQ ID NO:2), YISSYNGATNYNQKFKG (SEQ ID NO:3), or YISVYNGATNYNQKFKG (SEQ ID NO:4), and a heavy chain CDR3 comprising RDYDYDVGMDY (SEQ ID NO:5); and/or (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVG-MDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11).

In certain embodiments of each of the aforementioned aspects, as well as other aspects and embodiments described elsewhere herein, the DLL4 antagonist is an antibody comprising (a) a heavy chain variable region having at least about 90%, at least about 95% or 100% sequence identity to SEQ ID NO:6, SEQ ID NO:7 or SEQ ID NO:8; and/or (b) a light chain variable region having at least about 90%, at least about 95% or 100% sequence identity to SEQ ID NO:12. In some embodiments, the DLL4 antagonist is antibody 21M18, 21M18 H7L2 or 21M18 H9L2. In some embodiments, the DLL4 antagonist is the antibody encoded by the plasmid having ATCC deposit no. PTA-8425 which was deposited with the American Type Culture Collection (ATCC), at 10801 University Boulevard, Manassas, Va., 20110, under the conditions of the Budapest Treaty on May 10, 2007. In some embodiments, the DLL4 antagonist is the antibody encoded by the plasmid having ATCC deposit no. PTA-8427 which was deposited with the ATCC under the conditions of the Budapest Treaty on May 10, 2007. In some embodiments, the DLL4 antagonist is the antibody produced by the hybridoma having ATCC deposit no. PTA-8670 which was deposited with the ATCC under the conditions of the Budapest Treaty on Sep. 28, 2007.

In certain embodiments of each of the aforementioned aspects, as well as other aspects and embodiments described elsewhere herein, the DLL4 antagonist is a recombinant antibody. In some embodiments, the antibody is a monoclonal antibody, a chimeric antibody, a humanized antibody, or a human antibody. In some embodiments, the antibody is an antibody fragment. In certain embodiments, the antibody or antibody fragment is monovalent, monospecific, bivalent, bispecific, or multispecific. In certain embodiments, the antibody is isolated. In other embodiments, the antibody is substantially pure.

In certain embodiments of each of the aforementioned aspects, as well as other aspects and embodiments described elsewhere herein, the DLL4 antagonist is an antibody that competes for specific binding to the extracellular domain of human DLL4 with an antibody encoded by the plasmid deposited with ATCC having deposit no. PTA-8425. In some embodiments, the DLL4 antagonist is an antibody that competes for specific binding to human DLL4 with an antibody encoded by the plasmid deposited with ATCC having deposit no. PTA-8427. In some embodiments, the DLL4 antagonist is an antibody that competes for specific binding to human DLL4 with an antibody produced by the hybridoma deposited with ATCC having deposit no. PTA-8670. In some embodiments, the DLL4 antagonist is an antibody that competes for specific binding to the extracellular domain of human DLL4 with antibody 21M18, 21M18 H7L2 or 21M18 H9L2.

In certain embodiments of each of the aforementioned aspects, as well as other aspects and embodiments described elsewhere herein, the methods further comprise administering at least one additional therapeutic agent appropriate for effecting combination therapy. In some embodiments, the additional therapeutic agent is a chemotherapeutic agent. In some embodiments, the additional therapeutic agent is an antibody. In some embodiments, the additional therapeutic agent is an alkylating agent, a nitrosourea, a taxane, a vinca alkaloid, a topoisomerase inhibitor, an antibiotic, a platinum-based agent, a protein kinase inhibitor, or an angiogenesis inhibitor. In certain embodiments, the additional therapeutic agent is dacarbazine, temozolomide, carmustine, lomustine, fotemustine, paclitaxel, docetaxel, vinblastine, irinotecan, thalidomide, streptozocin, dactinomycin, mechlorethamine, cisplatin, carboplatin, imatanib mesylate, sorafenib, sutent, erlotinib, GDC-0879, PLX4032, or PLX4720. In some embodiments, the additional therapeutic agent is a protein kinase inhibitor. In some embodiments, the additional therapeutic agent is carboplatin. In some embodiments, the additional therapeutic agents are carboplatin and paclitaxel. In some embodiments, the additional therapeutic agent is PLX4032 or PLX4720. In some embodiments, the additional therapeutic agent is dacarbazine.

Pharmaceutical compositions comprising a DLL4 antagonist as described herein and a pharmaceutically acceptable vehicle (or carrier) are further provided, as are cell lines that produce the DLL4 antagonists. Also provided are methods of inhibiting melanoma growth and/or metastasis in a human subject comprising administering to the subject an effective amount of a composition comprising DLL4 antagonists. Methods of treating melanoma and/or metastatic melanoma in a subject comprising administering to the subject an effective amount of a composition comprising DLL4 antagonists are also provided.

Where aspects or embodiments of the invention are described in terms of a Markush group or other grouping alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claims invention.

BRIEF DESCRIPTION OF THE DRAWINGS

In FIG. 1 and all subsequent figures unless otherwise noted, anti-DLL4 antibody is a 1:1 mixture of 21M18 H7L2 antibody (anti-human DLL4) and 21R30 antibody (anti-mouse DLL4). Antibodies were administered at 15 mg/kg once a week, wherein the 15 mg/kg reflects the amount of the antibody mixture.

DETAILED DESCRIPTION OF THE INVENTION

Figure 1A:
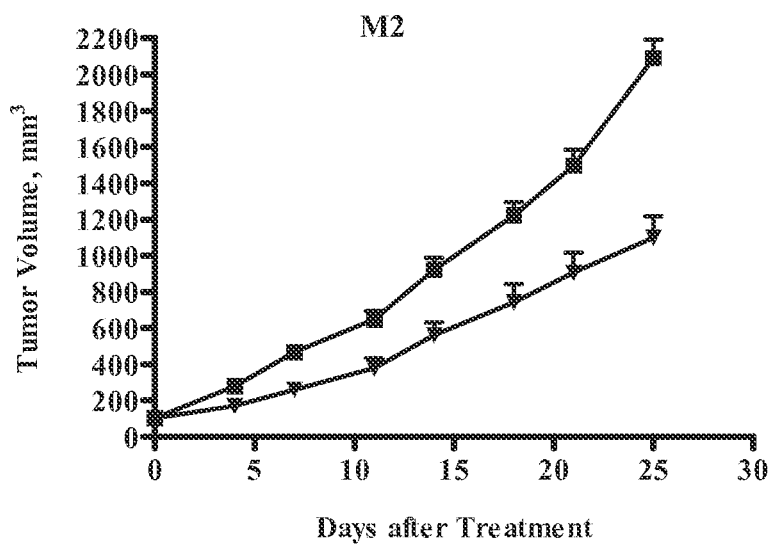
FIG. 1. Inhibition of melanoma tumor growth in vivo by anti-DLL4 antibodies. M2 (A), M3 (B), M4 (C), and M5 (D) melanoma tumor cells were injected subcutaneously into NOD/SCID mice. Mice were treated with control antibody (■) or anti-DLL4 antibody (▼). Data is shown as tumor volume (mm$^3$) over days post-treatment.
Figure 1B:
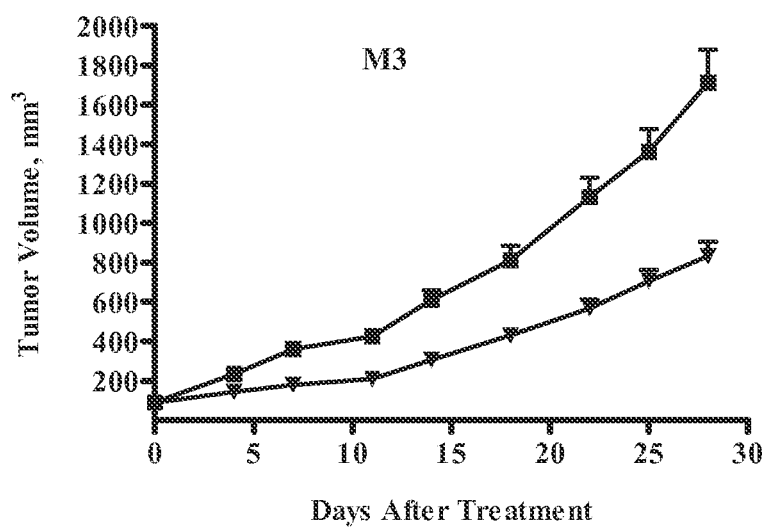
Figure 1C:
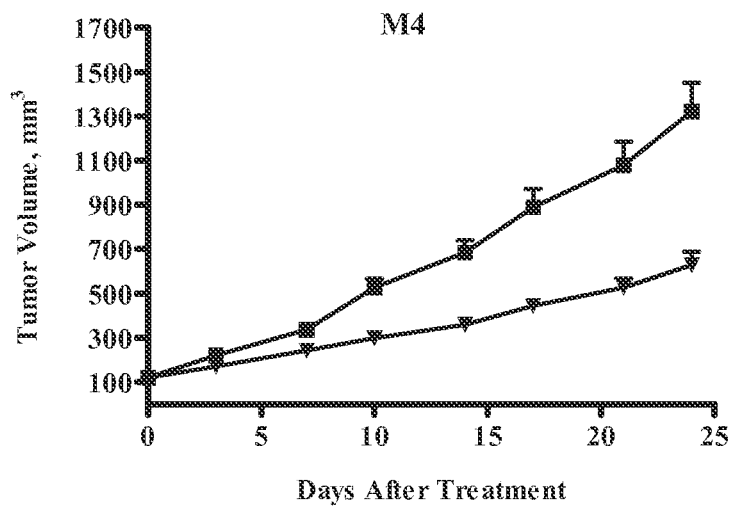

The present invention provides methods of inhibiting growth of a melanoma tumor, methods of treating melanoma, methods of inhibiting melanoma metastases and methods of reducing the frequency of cancer stem cells or tumor initiating cells in a melanoma tumor. The methods provided herein comprise administering a DLL4 antagonist to a subject. In some embodiments, the DLL4 antagonist is an antibody that specifically binds the extracellular domain of human DLL4. In some embodiments, the DLL4 antagonist is an antibody that specifically binds an epitope within amino acids 27-217 of the extracellular domain of human DLL4. Related polypeptides and polynucleotides, compositions comprising the DLL4 antagonists, and methods of making the DLL4 antagonists are also provided.

A number of melanoma tumors were established in a xenograft model and were evaluated for B-raf mutations (Example 1). Treatment with anti-DLL4 antibodies was shown to reduce the growth of both wild-type B-raf and mutant B-raf melanoma tumors (Example 2 and FIG. 1). Treatment with anti-DLL4 antibodies, either alone or in combination with a chemotherapeutic agent, was shown to reduce the growth of melanoma tumors and to increase the percentage of apoptotic cells. Furthermore, the treatment was shown to reduce the frequency of cancer stem cells/tumor initiating cells in a melanoma tumor (Examples 3-4, 6 and FIGS. 2-4 and 6). Treatment with anti-DLL4 antibodies in combination with a B-raf inhibitor was shown to inhibit growth of a melanoma tumor to a greater extent than the B-raf inhibitor alone (Example 5 and FIG. 5). In addition, anti-DLL4 antibodies were shown to inhibit growth of metastases after initial treatment and also after excision of the primary melanoma tumor (Examples 7-8 and FIGS. 7 and 8).

I. Definitions

To facilitate an understanding of the present invention, a number of terms and phrases are defined below.

The term "antagonist" as used herein includes any molecule that partially or fully blocks, inhibits, or neutralizes the expression of or the biological activity of a target molecule disclosed herein. Such biological activity includes, but is not limited to, inhibition of tumor growth and/or inhibition of tumor metastasis. The term "antagonist" includes any molecule that partially or fully blocks, inhibits, or neutralizes a biological activity of the Notch pathway. Suitable antagonist molecules include, but are not limited to, antibodies or fragments thereof which bind Notch receptors or Notch ligands (e.g., DLL4).

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site or antigen-binding site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen recognition site of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy chain constant domains referred to as alpha, delta, epsilon, gamma, and mu, respectively. The different classes of immunoglobulins have different and well known subunit structures and three-dimensional configurations. Antibodies can be naked or conjugated to other molecules including, but not limited to, toxins and radioisotopes.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

The term "variable region" of an antibody refers to the variable region of the antibody light chain or the variable region of the antibody heavy chain, either alone or in combination. The variable regions of the heavy and light chain each consist of four framework regions connected by three complementarity determining regions (CDRs) also known as hypervariable regions. The CDRs in each chain are held together in close proximity by the framework regions and, with the CDRs from the other chain, contribute to the formation of the antigen-binding site of the antibody. There are at least two techniques for determining CDRs: (1) an approach based on cross-species sequence variability (i.e., Kabat et al., 1991, *Sequences of Proteins of Immunological Interest, 5th Edition*, National Institutes of Health, Bethesda Md.); and (2) an approach based on crystallographic studies of antigen-antibody complexes (Al-Lazikani et al., 1997, *J. Molec. Biol.* 273:927-948). In addition, combinations of these two approaches are sometimes used in the art to determine CDRs.

The term "monoclonal antibody" refers to a homogeneous antibody population involved in the highly specific recognition and binding of a single antigenic determinant, or epitope. This is in contrast to polyclonal antibodies that typically include a mixture of different antibodies directed against different antigenic determinants. The term "monoclonal antibody" encompasses both intact and full-length monoclonal antibodies as well as antibody fragments (such as Fab, Fab', F(ab')2, Fv fragments), single chain Fv (scFv) mutants, fusion proteins comprising an antibody portion, and any other modified immunoglobulin molecule comprising an antigen recognition site. Furthermore, "monoclonal antibody" refers to such antibodies made in any number of manners including, but not limited to, hybridoma production, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences.

The term "human antibody" means an antibody produced by a human or an antibody having an amino acid sequence corresponding to an antibody produced by a human made using any technique known in the art. This definition of a human antibody includes intact or full-length antibodies, and fragments thereof.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammal (e.g., mouse, rat, rabbit, etc.) with the desired specificity, affinity, and/or capability while the constant regions are homologous to the sequences in antibodies derived from another species (usually human) to avoid eliciting an immune response in that species.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids (often referred to as "linear epitopes") and noncontiguous amino acids juxtaposed by tertiary folding of a protein (often referred to as "conformation epitopes"). Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

The terms "specifically binds" or "specific binding" mean that a binding agent or an antibody reacts or associates more frequently, more rapidly, with greater duration, with greater affinity, or with some combination of the above to an epitope or protein than with alternative substances, including unrelated proteins. In certain embodiments, "specifically binds" means, for instance, that an antibody binds to a protein with a $K_D$ of about 0.1 mM or less, but more usually less than about 1 µM. In certain embodiments, "specifically binds" means that an antibody binds to a protein at times with a $K_D$ of at least about 0.1 µM or less, and at other times at least about 0.01 µM or less. Because of the sequence identity between homologous proteins in different species, specific binding can include an antibody that recognizes a particular protein such as DLL4 in more than one species (e.g., mouse DLL4 and human DLL4). It is understood that an antibody or binding moiety that specifically binds to a first target may or may not specifically bind to a second target. As such, "specific binding" does not necessarily require (although it can include) exclusive binding, i.e. binding to a single target. Thus, an antibody may, in certain embodiments, specifically bind to more than one target. In certain embodiments, the multiple targets may be bound by the same antigen-binding site on the antibody. For example, an antibody may, in certain instances, comprise two identical antigen-binding sites, each of which specifically binds the same epitope on two or more proteins. In certain alternative embodiments, an antibody may be bispecific and comprise at least two antigen-binding sites with differing specificities. By way of non-limiting example, a bispecific antibody may comprise one antigen-binding site that recognizes an epitope on a DLL4 protein, and further comprises a second, different antigen-binding site that recognizes a different epitope on a second protein, such as Notch. Generally, but not necessarily, reference to binding means specific binding.

The terms "polypeptide" or "peptide" or "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "polynucleotide" or "nucleic acid," are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps"; substitution of one or more of the naturally occurring nucleotides with an analog; internucleotide modifications such as uncharged linkages (e.g., methyl phosphonates, phosphotriesters, phosphoamidates, cabamates, etc.) and charged linkages (e.g., phosphorothioates, phosphorodithioates, etc.); pendant moieties, such as proteins (e.g., nucleases, toxins, antibodies, signal peptides, poly-L-lysine, etc.); intercalators (e.g., acridine, psoralen, etc.); chelators (e.g., metals, radioactive metals, boron, oxidative metals, etc.); alkylators; modified linkages (e.g., alpha anomeric nucleic acids, etc.); as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azidoribose, carbocyclic sugar analogs, alpha-anomeric sugars, epimeric sugars such as arabinose, xyloses or lyxoses, pyranose sugars, furanose sugars, heptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical.

"Conditions of high stringency" may be identified by those that: (1) employ low ionic strength and high temperature for washing, for example 0.015M sodium chloride/0.0015M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software are known in the art that may be used to obtain alignments of amino acid or nucleotide sequences. These include, but are not limited to, BLAST, ALIGN, Megalign, and BestFit. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues in length or any integral value therebetween. In some embodiments, identity exists over a longer region than 60-80 residues, such as at least about 90-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the DLL4 protein to which the polypeptide or antibody binds. Methods of identifying nucleotide and amino acid conservative substitutions which do not eliminate antigen binding are well-known in the art.

The term "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure.

As used herein, "substantially pure" refers to material which is at least 50% pure (i.e., free from contaminants), more preferably at least 90% pure, more preferably at least 95% pure, more preferably at least 98% pure, more preferably at least 99% pure.

The term "melanoma" as used herein refers to all types of melanoma, including, cutaneous melanoma, extracutaneous melanoma, superficial spreading melanoma, malignant melanoma, nodular melanoma, nodular malignant melanoma, polypoid melanoma, acral lentiginous melanoma, lentiginous malignant melanoma, lentigo maligna melanoma, mucosal lentignous melanoma, mucosal melanoma, soft-tissue melanoma, ocular melanoma, and desmoplastic melanoma. The term "melanoma" includes primary melanoma and metastatic melanoma.

The terms "tumor" and "neoplasm" refer to any mass of tissue that results from excessive cell growth or proliferation, either benign (noncancerous) or malignant (cancerous) including pre-cancerous lesions.

The term "mutant" refers to a protein comprising at least one amino acid mutation as compared to the wild-type protein (or to a nucleotide sequence encoding such a protein). Mutants may include, but are not limited to, allelic variants, splice variants, substitution variants, deletion variants, and insertion variants. The term "mutation" refers to at least one amino acid mutation in the sequence of a protein as compared to the wild-type sequence (or to a nucleotide sequence encoding such a protein). The terms "mutant tumor" or "tumor comprising (or comprises) a mutation" are used interchangeably herein and refer to a population of tumor cells wherein a mutation can be detected, at either the protein or nucleotide level. The term "cancer comprising (or comprises) a mutation" as used herein refer to a population of cancer cells wherein a mutation can be detected, at either the protein or nucleotide level. Mutations can be detected by techniques and methods known to one of skill in the art including, but not limited to, PCR-based assays (e.g., polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays), direct sequencing, "Nex-Gen" sequencing, 454 sequencing, primer extension reactions, electrophoresis, oligonucleotide ligation assays, hybridization assays, TaqMan assays, SNP genotyping assays, high resolution melting assays and microarray analyses.

The term "activating mutation" refers to a mutation that results in constitutive activation of a protein, for example, B-raf, and constitutive activation of a signaling pathway (e.g. MAPK pathway). In some embodiments, a B-raf protein comprising an activating mutation initiates constitutive activity of several pathways including, but not limited to, the MAP kinase cascade and the PI3 kinase cascade. In some embodiments, constitutive activity by the B-raf mutant and signaling pathways contributes significantly to several aspects of the malignant phenotype, including deregulation of cellular proliferation, impaired differentiation, reduced apoptosis and prolonged cell survival.

The terms "cancer stem cell" or "CSC" or "tumor stem cell" or "tumor initiating cell" or "solid tumor stem cell" or "tumorigenic stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties confer on the "cancer stem cells" or "tumor initiating cells" the ability to form palpable tumors upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" or "tumor cell" and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on cancer stem cells the ability to form palpable tumors upon serial transplantation into an immunocompromised host (e.g., a mouse) compared to non-tumorigenic tumor cells, which are unable to form tumors upon serial transplantation. It has been observed that non-tumorigenic tumor cells may form a tumor upon primary transplantation into an immunocompromised host after obtaining the tumor cells from a solid tumor, but those non-tumorigenic tumor cells do not give rise to a tumor upon serial transplantation.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The phrase "pharmaceutically acceptable salt" refers to a salt of a compound that is pharmaceutically acceptable and that possesses the desired pharmacological activity of the parent compound.

The phrase "pharmaceutically acceptable excipient, carrier or adjuvant" refers to an excipient, carrier or adjuvant that can be administered to a subject, together with at least one antagonist or antibody of the present disclosure, and which does not destroy the pharmacological and/or biological activity thereof and is nontoxic when administered in doses sufficient to deliver a therapeutic amount of the antagonist.

The phrase "pharmaceutically acceptable vehicle" refers to a diluent, adjuvant, excipient, or carrier with which at least one antagonist or antibody of the present disclosure is administered.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug (e.g., an antibody) can reduce the number of cancer cells; reduce the tumor size; inhibit and/or stop cancer cell infiltration into peripheral organs including, for example, the spread of cancer into soft tissue and bone; inhibit and/or stop tumor metastasis; inhibit and/or stop tumor growth; relieve to some extent one or more of the symptoms associated with the cancer; reduce morbidity and mortality; improve quality of life; decrease tumorigenicity, tumorgenic frequency, or tumorgenic capacity of a tumor; reduce the number or frequency of cancer stem cells in a tumor; differentiate tumorigenic cells to a non-tumorigenic state; or a combination of such effects. To the extent the drug prevents growth and/or kills existing cancer cells, it can be referred to as cytostatic and/or cytotoxic.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer (e.g., melanoma) according to the methods of the present invention if the patient shows one or more of the following: a reduction in the number of, or complete absence of, cancer or tumor cells; a reduction in the tumor size; inhibition of, or an absence of, cancer or tumor cell infiltration into peripheral organs including, for example, the spread of tumor into soft tissue and bone; inhibition of, or an absence of, tumor metastasis; inhibition of, or an absence of, tumor growth; relief of one or more symptoms associated with the specific cancer; reduced morbidity and mortality; improvement in quality of life; reduction in tumorigenicity, tumorgenic frequency, or tumorgenic capacity of a tumor; reduction in the number or frequency of cancer stem cells in a tumor; reduction in the number or frequency of tumor initiating cells in a tumor; differentiation of tumorigenic cells to a non-tumorigenic state; or some combination of effects.

The phrase "substantially non-responsive" as used herein refers to a tumor or a cancer (e.g., melanoma) that shows stable growth or increased growth after administration of a therapeutic agent. The phrase may refer to a patient that shows stable disease or progressive disease after administration of a therapeutic agent. The phrase may be used when referring to tumors or cancers that are resistant to treatment with a therapeutic agent. The phrase "substantially non-responsive to at least one B-raf inhibitor" as used herein refers to a tumor or a cancer (e.g., melanoma) that shows stable growth or increased growth after administration of a B-raf inhibitor. In some embodiments, a B-raf inhibitor is administered to a patient in need of treatment, and "substantially non-responsive" to the B-raf inhibitor includes: no reduction in the number of, or continued growth of, tumor cells; no reduction in the tumor size; an increase in tumor size; no inhibition of, or a continuation of, tumor cell infiltration into peripheral organs including, for example, the spread of tumor cells into soft tissue and bone; no inhibition of, or a continuation of, tumor metastasis; no inhibition of, or a continuation of, tumor growth; no or little relief of one or more symptoms associated with the specific cancer; no or little reduction in tumorigenicity, tumorgenic frequency, or tumorgenic capacity of a tumor; no or little reduction in the number or frequency of cancer stem cells in a tumor; or some combination of effects.

As used in the present disclosure and claims, the singular forms "a" "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided.

The term "and/or" as used in a phrase such as "A and/or B" herein is intended to include: A and B, A or B, A (alone) and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. DLL4 Antagonists

The present invention provides DLL4 antagonists for use in methods of inhibiting growth of a melanoma tumor. The invention further provides DLL4 antagonists for use in methods of treating melanoma.

In certain embodiments, the DLL4 antagonist specifically binds the extracellular domain of human DLL4. In some embodiments, the DLL4 antagonist is an antibody. In some embodiments, the DLL4 antagonist or antibody specifically binds an epitope within amino acids 27-217 of the extracellular domain of human DLL4 (SEQ ID NO:14). In some embodiments, the DLL4 antagonist or antibody specifically binds an epitope formed by a combination of the N-terminal region of human DLL4 (SEQ ID NO:15) and the DSL region of human DLL4 DSL region (SEQ ID NO:16). In some embodiments, the DLL4 antagonist or antibody binds an epitope comprising amino acids 66-73 (QAVVSPGP; SEQ ID NO:17) of human DLL4. In some embodiments, the DLL4 antagonist or antibody binds an epitope comprising amino acids 139-146 (LISKIAIQ; SEQ ID NO:18) of human DLL4. In some embodiments, the DLL4 antagonist or antibody binds an epitope comprising amino acids 66-73 (QAVVSPGP; SEQ ID NO:17) and (LISKIAIQ; SEQ ID NO:18) of human DLL4.

In certain embodiments, the DLL4 antagonist (e.g., an antibody) binds to DLL4 with a dissociation constant ($K_D$) of about 1 µM or less, about 100 nM or less, about 40 nM or less, about 20 nM or less, about 10 nM or less, or about 1 nM or less. In certain embodiments, the DLL4 antagonist or antibody binds to human DLL4 with a $K_D$ of about 40 nM or less, about 20 nM or less, about 10 nM or less, or about 1 nM or less. In some embodiments, the dissociation constant of the antagonist or antibody to DLL4 is the dissociation constant determined using a DLL4 fusion protein comprising a DLL4 extracellular domain (e.g., a DLL4 ECD-Fc fusion protein) immobilized on a Biacore chip.

In certain embodiments, the DLL4 antagonist (e.g., an antibody) binds to DLL4 with a half maximal effective concentration ($EC_{50}$) of about 1 µM or less, about 100 nM or less, about 40 nM or less, about 20 nM or less, about 10 nM or less, or about 1 nM or less. In certain embodiments, the DLL4 antagonist or antibody binds to human DLL4 with an $EC_{50}$ of about 40 nM or less, about 20 nM or less, about 10 nM or less, or about 1 nM or less.

In certain embodiments, the DLL4 antagonist is a polypeptide. In certain embodiments, the DLL4 antagonist or polypeptide is an antibody. In some embodiments, the antibody is an IgA, IgD, IgE, IgG, or IgM antibody. In certain embodiments, the antibody is an IgG antibody. In some embodiments, the antibody is an IgG1 antibody. In some embodiments, the antibody is an IgG2 antibody. In certain embodiments, the antibody is a recombinant antibody. In certain embodiments, the antibody is a chimeric antibody. In certain embodiments, the antibody is a monoclonal antibody. In certain embodiments, the antibody is a humanized antibody. In certain embodiments, the antibody is a human antibody. In certain embodiments, the antibody is an antibody fragment comprising an antigen-binding site.

In some embodiments, the antibody is a monospecific or a multispecific (e.g., a bispecific) antibody. In some embodiments, the antibody is a monovalent antibody.

The DLL4 antagonists (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see, e.g., Ausubel et al., Editors, 1994-present, *Current Protocols in Molecular Biology*, John Wiley & Sons, Inc., New York, N.Y.).

In some embodiments, the specific binding of a DLL4 antagonist (e.g., an antibody) to human DLL4 may be determined using ELISA. An ELISA assay comprises preparing DLL4 antigen, coating wells of a 96 well microtiter plate with antigen, adding to the wells the DLL4 antagonist or antibody conjugated to a detectable compound such as an enzymatic substrate (e.g., horseradish peroxidase or alkaline phosphatase), incubating for a period of time and detecting the presence of the binding agent or antibody. In some embodiments, the DLL4 antagonist or antibody is not conjugated to a detectable compound, but instead a second conjugated antibody that recognizes the DLL4 antagonist or antibody is added to the well. In some embodiments, instead of coating the well with DLL4 antigen, the DLL4 antagonist or antibody can be coated to the well, antigen is added to the coated well and then a second antibody conjugated to a detectable compound is added. One of skill in the art would be knowledgeable as to the parameters that can be modified and/or optimized to increase the signal detected, as well as other variations of ELISAs that can be used (see e.g., Ausubel et al., Eds, 1994, Current Protocols in Molecular Biology, Vol. 1, John Wiley & Sons, Inc., New York at 11.2.1).

The binding affinity of an antagonist or antibody to DLL4 and the on-off rate of an antibody-antigen interaction can be determined by competitive binding assays. In some embodiments, a competitive binding assay is a radioimmunoassay comprising the incubation of labeled antigen (e.g., $^{3}H$ or $^{125}I$), or fragment or variant thereof, with the antibody of interest in the presence of increasing amounts of unlabeled antigen followed by the detection of the antibody bound to the labeled antigen. The affinity of the antibody for the antigen and the on-off rates can be determined from the data by Scatchard plot analysis. In some embodiments, Biacore kinetic analysis is used to determine the binding affinities and on-off rates of antagonists or antibodies that bind DLL4. Biacore kinetic analysis comprises analyzing the binding and dissociation of antibodies from antigens (e.g., DLL4 proteins) that have been immobilized on the surface of a Biacore chip. In some embodiments, Biacore kinetic analyses can be used to study binding of different antibodies in qualitative epitope competition binding assays.

In some embodiments, the DLL4 antagonists are polyclonal antibodies. Polyclonal antibodies can be prepared by any known method. Polyclonal antibodies are prepared by immunizing an animal (e.g., a rabbit, rat, mouse, goat, donkey, etc.) by multiple subcutaneous or intraperitoneal injections of an antigen of interest (e.g., a purified peptide fragment, full-length recombinant protein, fusion protein, etc.). The antigen can be optionally conjugated to a carrier protein such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal (usually from blood or ascites). The polyclonal antibodies can be purified from serum or ascites according to standard methods in the art including, but not limited to, affinity chromatography, ion-exchange chromatography, gel electrophoresis, and dialysis.

In some embodiments, the DLL4 antagonists are monoclonal antibodies. Monoclonal antibodies can be prepared using hybridoma methods known to one of skill in the art (see e.g., Kohler and Milstein, 1975, *Nature* 256:495). Using the hybridoma method, a mouse, hamster, or other appropriate host animal, is immunized as described above to elicit from lymphocytes the production of antibodies that specifically bind the immunizing antigen. In some embodiments, lymphocytes can be immunized in vitro. In some embodiments, the immunizing antigen (e.g., DLL4) is a human protein or a portion thereof. In some embodiments, the immunizing antigen (e.g., DLL4) is a mouse protein or a portion thereof. In some embodiments, the immunizing antigen is an extracellular domain of human DLL4. In some embodiments, the immunizing antigen is an extracellular domain of mouse DLL4. In some embodiments, a mouse is immunized with a human antigen. In some embodiments, a mouse is immunized with a mouse antigen.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed against a chosen antigen may be identified by a variety of techniques including, but not limited to, immunoprecipitation, immunoblotting, and in vitro binding assays (e.g., flow cytometry, FACS, enzyme-linked immunosorbent assay (ELISA), or radioimmunoassay (RIA)). The hybridomas can be propagated either in in vitro culture using standard methods (J. W. Goding, 1996, *Monoclonal Antibodies: Principles and Practice* $3^{rd}$ *Edition*, Academic Press, San Diego Calif.) or in vivo as ascites in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art (see e.g., U.S. Pat. No. 4,816,567). The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional techniques. The isolated polynucleotides encoding the heavy and light chains are cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin protein.

In some embodiments, recombinant monoclonal antibodies, or fragments thereof, can also be isolated from phage display libraries expressing variable domains or CDRs of a desired species (see e.g., McCafferty et al., 1990, *Nature,* 348:552-554; Clackson et al., 1991, *Nature,* 352:624-628; and Marks et al., 1991, *J. Mol. Biol.,* 222:581-597).

The polynucleotide(s) encoding a monoclonal antibody can be further modified using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region(s) can be used to optimize specificity, affinity, and/or other biological characteristics of a monoclonal antibody. In some embodiments, site-directed mutagenesis of the CDRs can be used to optimize specificity, affinity, and/or other biological characteristics of a monoclonal antibody.

In some embodiments, the DLL4 antagonist is a humanized antibody. Typically, humanized antibodies are human immunoglobulins in which residues from the complementary determining regions (CDRs) are replaced by residues from CDRs of a non-human species (e.g., mouse, rat, rabbit, hamster) that have the desired specificity, affinity, and/or capability by methods known to one skilled in the art. In some embodiments, the Fv framework region residues of a human immunoglobulin are replaced with the corresponding framework region residues from a non-human immunoglobulin that has the desired specificity, affinity, and/or capability. In some embodiments, the humanized antibody is further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all, or substantially all, of the CDRs that correspond to the non-human immunoglobulin whereas all, or substantially all, of the framework regions are those of a human immunoglobulin consensus sequence. In some embodiments, the humanized antibody can also comprise at least a portion of an immunoglobulin constant region or domain (Fc), typically that of a human immunoglobulin. In certain embodiments, such humanized antibodies are used therapeutically because they should be less antigenic and may reduce HAMA (human anti-mouse antibody) responses when administered to a human subject. One skilled in the art would be able to obtain a functional humanized antibody with reduced immunogenicity following known techniques (see, for example, U.S. Pat. Nos. 5,225,539; 5,585,089; 5,693,761; and 5,693, 762).

In some embodiments, the invention provides an antibody that specifically binds the extracellular domain of human DLL4, wherein the antibody comprises one, two, three, four, five and/or six of the CDRs of antibodies 21M18, 21M18 H9L2, and/or 21M18 H7L2. These antibodies have been described in U.S. Pat. No. 7,750,124. Antibodies 21M18 H7L2 and 21M18 H9L2 are humanized forms of the murine 21M18 antibody.

In certain embodiments, the invention provides a DLL4 antagonist, wherein the antagonist is a DLL4 antibody that specifically binds an epitope within amino acids 27-217 of the extracellular domain of human DLL4, and wherein the antibody comprises: a heavy chain CDR1 comprising TAYYIH (SEQ ID NO:1), a heavy chain CDR2 comprising YISCYNGATNYNQKFKG (SEQ ID NO:2), YISSYNGATNYNQKFKG (SEQ ID NO:3), or YISVYNGATNYNQKFKG (SEQ ID NO:4), and a heavy chain CDR3 comprising RDYDYDVGMDY (SEQ ID NO:5). In some embodiments, the antibody further comprises a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the antibody comprises a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the antibody comprises a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11).

In certain embodiments, the invention provides an antibody that specifically binds an epitope within amino acids 27-217 of the extracellular domain of human DLL4, wherein the antibody comprises a heavy chain variable region having at least about 80% sequence identity to SEQ ID NO:6, SEQ ID NO:7, or SEQ ID NO:8, and/or a light chain variable region having at least 80% sequence identity to SEQ ID NO:12. In certain embodiments, the antibody comprises a heavy chain variable region having at least about 85%, at least about 90%, at least about 95%, at least about 97%, or at least about 99% sequence identity to SEQ ID NO:6, SEQ ID NO:7 or SEQ ID NO:8. In certain embodiments, the antibody comprises a light chain variable region having at least about 85%, at least about 90%, at least about 95%, at least about 97%, or at least about 99% sequence identity to SEQ ID NO:12. In certain embodiments, the antibody comprises a heavy chain variable region having at least about 95% sequence identity to SEQ ID NO:6, SEQ ID NO:7 or SEQ ID NO:8, and/or a light chain variable region having at least about 95% sequence identity to SEQ ID NO:12. In certain embodiments, the antibody comprises a heavy chain variable region comprising SEQ ID NO:6, SEQ ID NO:7, or SEQ ID NO:8, and/or a light chain variable region comprising SEQ ID NO:12. In certain embodiments, the antibody comprises a heavy chain variable region comprising SEQ ID NO:6 and a light chain variable region comprising SEQ ID NO:12. In certain embodiments, the antibody comprises a heavy chain variable region comprising SEQ ID NO:7 and a light chain variable region comprising SEQ ID NO:12. In certain embodiments, the antibody comprises a heavy chain variable region comprising SEQ ID NO:8 and a light chain variable region comprising SEQ ID NO:12.

In certain embodiments, the DLL4 antagonist (e.g., an antibody) binds to the same epitope that an antibody comprising the heavy chain variable region comprising SEQ ID NO:6, and/or a light chain variable region comprising SEQ ID NO:12 binds. In certain embodiments, the DLL4 antagonist (e.g., an antibody) binds to the same epitope that an antibody comprising the heavy chain variable region comprising SEQ ID NO:7, and/or a light chain variable region comprising SEQ ID NO:12 binds. In certain embodiments, the DLL4 antagonist (e.g., an antibody) binds to the same epitope that an antibody comprising the heavy chain variable region comprising SEQ ID NO:8, and/or a light chain variable region comprising SEQ ID NO:12 binds. In some embodiments, the DLL4 antagonist or antibody binds to the same epitope as antibody 21M18. In some embodiments, the DLL4 antagonist or antibody binds to the same epitope as antibody 21M18 H7L2. In some embodiments, the DLL4 antagonist or antibody binds to the same epitope as antibody 21M18 H9L2.

In certain embodiments, the DLL4 antagonist (e.g., an antibody) competes for specific binding to an extracellular domain of human DLL4 with an antibody, wherein the antibody comprises a heavy chain variable region comprising SEQ ID NO:6, and/or a light chain variable region comprising SEQ ID NO:12. In certain embodiments, the DLL4 antagonist competes for specific binding to an extracellular domain of human DLL4 with an antibody, wherein the antibody comprises a heavy chain variable region comprising SEQ ID NO:7, and/or a light chain variable region comprising SEQ ID NO:12. In certain embodiments, the DLL4 antagonist competes for specific binding to an extracellular domain of human DLL4 with an antibody, wherein the antibody comprises a heavy chain variable region comprising SEQ ID NO:8, and/or a light chain variable region comprising SEQ ID NO:12. In some embodiments, the DLL4 antagonist competes for specific binding to an extracellular domain of human DLL4 with an antibody encoded by the plasmid deposited with ATCC having deposit no. PTA-8425. In some embodiments, the DLL4 antagonist or antibody competes for specific binding to an extracellular domain of human DLL4 with an antibody encoded by the plasmid deposited with ATCC having deposit no. PTA-8427. In some embodiments, the DLL4 antagonist or antibody competes for specific binding to an extracellular domain of human DLL4 with an antibody produced by the hybridoma deposited with ATCC having deposit no. PTA-8670. In some embodiments, the DLL4 antagonist or antibody competes for specific binding to an epitope within amino acids 27-217 of the extracellular domain of human DLL4 in a competitive binding assay.

In certain embodiments, the DLL4 antagonist is a human antibody. Human antibodies can be directly prepared using various techniques known in the art. In some embodiments, human antibodies may be generated from immortalized human B lymphocytes immunized in vitro or from lymphocytes isolated from an immunized individual. In either case, cells that produce an antibody directed against a target antigen can be generated and isolated. In some embodiments, a human antibody can be selected from a phage library, where that phage library expresses human antibodies (see e.g., Vaughan et al., 1996, *Nat. Biotech.*, 14:309-314; Sheets et al., 1998, *Proc. Nat'l. Acad. Sci.*, 95:6157-6162; Hoogenboom and Winter, 1991, *J. Mol. Biol.*, 227:381; and Marks et al., 1991, *J. Mol. Biol.*, 222:581). Alternatively, phage display technology can be used to produce human antibodies and antibody fragments in vitro, from immunoglobulin variable domain gene repertoires from unimmunized donors. Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.*, 376:1182-1200. Once antibodies are identified, affinity maturation strategies known in the art, including but not limited to, chain shuffling (Marks et al., 1992, *Bio/Technology*, 10:779-783) and site-directed or random mutagenesis, may be employed to generate high affinity human antibodies.

In some embodiments, human antibodies can be made in transgenic mice that contain human immunoglobulin loci. Upon immunization these mice are capable of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments, the DLL4 antagonist is a bispecific antibody. Bispecific antibodies are capable of specifically recognizing and binding to at least two different epitopes. The different epitopes can be within the same molecule or on different molecules. In some embodiments, the antibodies can specifically recognize and bind a first antigen target, (e.g., DLL4) as well as a second antigen target, such as an effector molecule on a leukocyte (e.g., CD2, CD3, CD28, or B7) or a Fc receptor (e.g., CD64, CD32, or CD16) so as to focus cellular defense mechanisms to the cell expressing the first antigen target. In some embodiments, the antibodies can be used to direct cytotoxic agents to cells which express a particular target antigen, such as DLL4. These antibodies possess an antigen-binding arm and an arm which binds a cytotoxic agent or a radionuclide chelator, such as EOTUBE, DPTA, DOTA, or TETA. In certain embodiments, the antibodies can be used to affect angiogenesis. In certain embodiments, the bispecific antibody specifically binds DLL4, as well as VEGF. In certain embodiments, the bispecific antibody specifically binds DLL4, as well as a second Notch ligand (e.g., Jagged1 or Jagged2), or at least one Notch receptor selected from the group consisting of Notch1, Notch2, Notch3, and Notch4.

Techniques for making bispecific antibodies are known by those skilled in the art, see for example, Millstein et al., 1983, *Nature*, 305:537-539; Brennan et al., 1985, *Science*, 229:81; Suresh et al, 1986, *Methods in Enzymol.*, 121:120; Traunecker et al., 1991, *EMBO J.*, 10:3655-3659; Shalaby et al., 1992, *J. Exp. Med.*, 175:217-225; Kostelny et al., 1992, *J. Immunol.*, 148:1547-1553; Gruber et al., 1994, *J. Immunol.*, 152:5368; U.S. Pat. No. 5,731,168; Int'l. Publication No. WO 2009/089004; and U.S. Patent Publication No. 2011/0123532). Bispecific antibodies can be intact antibodies or antibody fragments. Antibodies with more than two valencies are also contemplated. For example, trispecific antibodies can be prepared (Tutt et al., 1991, *J. Immunol.*, 147:60). Thus, in certain embodiments the antibodies to DLL4 are multispecific.

In certain embodiments, the DLL4 antagonists (e.g., antibodies or other polypeptides) described herein may be monospecific. For example, in certain embodiments, each of the one or more antigen-binding sites that an antibody contains is capable of binding (or binds) a homologous epitope on DLL4.

In certain embodiments, the DLL4 antagonist is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in, and secreted from, *E. coli* or other host cells, allowing for the production of large amounts of these fragments. In some embodiments, antibody fragments are isolated from antibody phage libraries as discussed herein. For example, methods can be used for the construction of Fab expression libraries (Huse et al., 1989, Science, 246: 1275-1281) to allow rapid and effective identification of monoclonal Fab fragments with the desired specificity for DLL4, or derivatives, fragments, analogs or homologs thereof. In some embodiments, antibody fragments are linear antibody fragments. In certain embodiments, antibody fragments are monospecific or bispecific. In certain embodiments, the DLL4 antagonist is a scFv. Various techniques can be used for the production of single-chain antibodies specific to DLL4 (see, e.g., U.S. Pat. No. 4,946,778).

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

For the purposes of the present invention, it should be appreciated that modified antibodies, or fragments thereof, can comprise any type of variable region that provides for the association of the antibody with DLL4. In this regard, the variable region may be derived from any type of mammal that can be induced to mount a humoral response and generate immunoglobulins against a desired antigen (e.g., DLL4). As such, the variable region of the modified antibodies can be, for example, of human, murine, non-human primate (e.g., cynomolgus monkeys, macaques, etc.) or lapine origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification. Although the CDRs may be derived from an antibody of the same class or even subclass as the antibody from which the framework regions are derived, it is envisaged that the CDRs will be derived from an antibody of a different class and preferably from an antibody from a different species. It may not be necessary to replace all of the CDRs with all of the CDRs from the donor variable region to transfer the antigen binding capacity of one variable domain to another. Rather, it may only be necessary to transfer those residues that are necessary to maintain the activity of the antigen binding site.

Alterations to the variable region notwithstanding, those skilled in the art will appreciate that the modified antibodies of this invention will comprise antibodies (e.g., full-length antibodies or antigen-binding fragments thereof) in which at least a fraction of one or more of the constant region domains has been deleted or otherwise altered so as to provide desired biochemical characteristics, such as increased tumor localization, increased tumor penetration, reduced serum half-life or increased serum half-life when compared with an antibody of approximately the same immunogenicity comprising a native or unaltered constant region. In some embodiments, the constant region of the modified antibodies comprises a human constant region. Modifications to the constant region include additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the entire CH2 domain has been removed ($\Delta$CH2 constructs). In some embodiments, the omitted constant region domain is replaced by a short amino acid spacer (e.g., 10 aa residues) that provides some of the molecular flexibility typically imparted by the absent constant region.

In certain embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase tumor localization and/or tumor penetration. Similarly, it may be desirable to simply delete the part of one or more constant region domains that control a specific effector function (e.g., complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind to a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (ADCC), release of inflammatory mediators, placental transfer, and control of immunoglobulin production.

In certain embodiments, the DLL4 antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody (e.g., DLL4 antibody) thereby increasing tumor localization and/or penetration. In other embodiments, the constant region modifications increase or reduce the serum half-life of the antibody. In some embodiments, the constant region is modified to eliminate disulfide linkages or oligosaccharide moieties allowing for enhanced tumor localization and/or penetration.

In certain embodiments, a DLL4 antibody does not have one or more effector functions. In some embodiments, the antibody has no antibody-dependent cellular cytoxicity (ADCC) activity and/or no complement-dependent cytoxicity (CDC) activity. In certain embodiments, the antibody does not bind to an Fc receptor and/or complement factors. In certain embodiments, the antibody has no effector function.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids.

Thus, the present invention provides methods for generating an antibody that binds the extracellular domain of human DLL4. In some embodiments, the method for generating an antibody that binds DLL4 comprises using hybridoma techniques. In some embodiments, the method comprises using an extracellular domain of mouse DLL4 or human DLL4 as an immunizing antigen. In some embodiments, the method of generating an antibody that binds DLL4 comprises screening a human phage library. The present invention further provides methods of identifying an antibody that binds to DLL4. In some embodiments, the antibody is identified by screening for binding to DLL4 with flow cytometry (FACS). In some embodiments, the antibody is screened for binding to human DLL4. In some embodiments, the antibody is screened for binding to mouse DLL4. In some embodiments, the antibody is identified by screening for inhibition or blocking of DLL4-induced Notch activation. In some embodiments, the DLL4 is human DLL4. In some embodiments, the Notch is human Notch1, Notch2, Notch3, or Notch4.

In certain embodiments, the antibodies as described herein are isolated. In certain embodiments, the antibodies as described herein are substantially pure.

Certain anti-DLL4 antibodies have been described, for example, in U.S. Pat. No. 7,750,124, which is incorporated by reference herein in its entirety. Certain additional anti-DLL4 antibodies are described in, e.g., International Patent Publication Nos. WO 2008/091222 and WO 2008/0793326, and U.S. Patent Application Publication Nos. 2008/ 0014196; 2008/0175847; 2008/0181899; and 2008/ 0107648, each of which is incorporated by reference herein in its entirety.

In some embodiments of the present invention, the DLL4 antagonists are polypeptides. The polypeptides can be recombinant polypeptides, natural polypeptides, or synthetic polypeptides that bind an epitope comprising amino acids within the extracellular domain of human DLL4. In some embodiments, the polypeptides comprise an antibody or fragment thereof that binds an epitope within the extracellular domain of human DLL4. It will be recognized by those of skill in the art that some amino acid sequences of a polypeptide can be varied without significant effect on the structure or function of the protein. Thus, the polypeptides further include variations of the polypeptides which show substantial binding activity to an epitope of the human DLL4 protein. In some embodiments, amino acid sequence variations of polypeptides include deletions, insertions, inversions, repeats, and/or type substitutions.

The polypeptides and variants thereof, can be further modified to contain additional chemical moieties not normally part of the polypeptide. The derivatized moieties can improve the solubility, the biological half-life or absorption of the polypeptide. The moieties can also reduce or eliminate any undesirable side effects of the polypeptides and variants. An overview for such chemical moieties can be found in *Remington: The Science and Practice of Pharmacy*, 21st Edition, 2005, University of the Sciences, Philadelphia, Pa.

The isolated polypeptides described herein can be produced by any suitable method known in the art. Such methods range from direct protein synthesis methods to constructing a DNA sequence encoding isolated polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and by selecting those codons that are favored in the host cell in which the recombinant polypeptide of interest will be produced. Standard methods can be applied to synthesize a polynucleotide sequence encoding a polypeptide of interest. For example, a complete amino acid sequence can be used to construct a back-translated gene. Further, a DNA oligomer containing a nucleotide sequence coding for the particular polypeptide can be synthesized. For example, several small oligonucleotides coding for portions of the desired polypeptide can be synthesized and then ligated. The individual oligonucleotides typically contain 5' and/or 3' overhangs for complementary assembly.

Once assembled (by synthesis, site-directed mutagenesis or another method), the polynucleotide sequences encoding a particular polypeptide of interest can be inserted into an expression vector and operatively linked to an expression control sequence appropriate for expression of the polypeptide in a desired host. Proper assembly can be confirmed by nucleotide sequencing, restriction mapping, and/or expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding DLL4 antagonists such as polypeptides or antibodies, or fragments thereof. For example, recombinant expression vectors can be replicable DNA constructs which have synthetic or cDNA-derived DNA fragments encoding a polypeptide chain of an anti-DLL4 antibody, or fragment thereof, operatively linked to suitable transcriptional or translational regulatory elements derived from mammalian, microbial, viral or insect genes. A transcriptional unit generally comprises an assembly of (1) a regulatory element or elements having a role in gene expression, for example, transcriptional promoters and/or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of an expression vector and control elements depends upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR1, pBR322, pMB9 and their derivatives and wider host range plasmids, such as M13 and other filamentous single-stranded DNA phages.

Suitable host cells for expression of a DLL4 antagonist polypeptide or antibody (or a DLL4 protein to use as an antigen) include prokaryotes, yeast, insect, or higher eukaryotic cells under the control of appropriate promoters. Prokaryotes include gram-negative or gram-positive organisms, for example, *E. coli* or Bacilli. Higher eukaryotic cells include established cell lines of mammalian origin as described below. Cell-free translation systems can also be employed.

Various mammalian or insect cell culture systems are used to express recombinant protein. Expression of recombinant proteins in mammalian cells may be preferred because such proteins are generally correctly folded, appropriately modified and completely functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants of these cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, 1988, *Bio/Technology*, 6:47.

The proteins produced by a transformed host can be purified according to any suitable method. Such methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence and glutathione-S-transferase can be attached to the protein to allow easy purification by passage over an appropriate affinity column. Isolated proteins can also be physically characterized using such techniques as proteolysis, high performance liquid chromatography (HPLC), nuclear magnetic resonance and x-ray crystallography.

For example, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose or other types commonly employed in protein purification. In some embodiments, a cation exchange step is employed. Suitable cation exchangers include various insoluble matrices comprising sulfopropyl or carboxymethyl groups. In some embodiments, a hydroxyapatite (CHT) media is employed, including but not limited to, ceramic hydroxyapatite. In some embodiments, one or more reversed-phase HPLC steps employing hydrophobic RP-HPLC media, (e.g., silica gel having pendant methyl or other aliphatic groups), is employed to further purify a protein. Some or all of the foregoing purification steps, in various combinations, can be employed to provide a homogeneous recombinant protein.

In some embodiments, recombinant protein produced in bacterial culture is isolated, for example, by initial extraction from cell pellets, followed by one or more concentration, salting-out, aqueous ion exchange, or size exclusion chromatography steps. In certain embodiments, HPLC is employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Application Pub. Nos. 2008/0312425; 2009/0187005; and U.S. Pat. No. 7,691,980.

In certain embodiments, the DLL4 antagonist is a polypeptide that is not an antibody. A variety of methods for identifying and producing non-antibody polypeptides that bind with high affinity to a protein target are known in the art. See, e.g., Skerra, 2007, *Curr. Opin. Biotechnol.*, 18:295-304; Hosse et al., 2006, *Protein Science*, 15:14-27; Gill et al., 2006, *Curr. Opin. Biotechnol.*, 17:653-658; Nygren, 2008, *FEBS J.*, 275:2668-76; and Skerra, 2008, *FEBS J.*, 275:2677-83. In certain embodiments, phage display technology may be used to produce and/or identify a DLL4 antagonist polypeptide. In certain embodiments, the DLL4 antagonist polypeptide comprises a protein scaffold of a type selected from the group consisting of protein A, protein G, a lipocalin, a fibronectin domain, an ankyrin consensus repeat domain, and thioredoxin.

In certain embodiments, the DLL4 antagonists or antibodies can be used in any one of a number of conjugated (e.g., an immunoconjugate or radioconjugate) or non-conjugated forms. In certain embodiments, the antibodies are used in non-conjugated form to harness the subject's natural defense mechanisms including complement-dependent cytotoxicity (CDC) and/or antibody dependent cellular toxicity (ADCC) to eliminate malignant or cancerous cells.

In certain embodiments, the DLL4 antagonist (e.g., an antibody or polypeptide) is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is a enzymatically active toxin of bacterial, fungal, plant, or animal origin, or fragments thereof, including but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, restrictocin, phenomycin, enomycin, and the tricothecenes. In certain embodiments, the cytotoxic agent is a radioactive isotope to produce a radioconjugate or a radioconjugated antibody. A variety of radionuclides are available for the production of radioconjugated antibodies including, but not limited to, $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re and $^{212}$Bi. Conjugates of an antibody and one or more small molecule toxins, such as a calicheamicin, maytansinoids, a trichothene, and CC1065, and the derivatives of these toxins that have toxin activity, can also be used. Conjugates of an antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents.

III. Polynucleotides

In certain embodiments, the invention encompasses polynucleotides comprising polynucleotides that encode a polypeptide that specifically binds an epitope comprising amino acids within the extracellular domain of human DLL4 or a fragment of such a polypeptide. The term "polynucleotides that encode a polypeptide" encompasses a polynucleotide which includes only coding sequences for the polypeptide as well as a polynucleotide which includes additional coding and/or non-coding sequences. For example, the invention provides a polynucleotide comprising a nucleic acid sequence that encodes an antibody to a human DLL4 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to produce the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, the polynucleotides comprise the coding sequence for the mature polypeptide fused in the same reading frame to a marker sequence that allows for, for example, purification and/or identification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO:20) which can be used in conjunction with other affinity tags.

The present invention further relates to variants of the hereinabove described polynucleotides encoding, for example, fragments, analogs, and/or derivatives.

In certain embodiments, the present invention provides isolated polynucleotides comprising polynucleotides having a nucleotide sequence at least 80% identical, at least 85% identical, at least 90% identical, at least 95% identical, and in some embodiments, at least 96%, 97%, 98% or 99% identical to a polynucleotide encoding a polypeptide comprising an antibody, or fragment thereof, described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, the polynucleotide variants contain alterations which produce silent substitutions, additions, or deletions, but do not alter the properties or activities of the encoded polypeptide. In some embodiments, the polynucleotide variants contain alterations which do not produce any changes in the amino acid sequence. In some embodiments, polynucleotide variants contain "silent" substitutions due to the degeneracy of the genetic code. Polynucleotide variants can be produced for a variety of reasons, for example, to optimize codon expression for a particular host (e.g., change codons in the human mRNA to those preferred by a bacterial host such as E. coli).

In certain embodiments, the polynucleotides as described herein are isolated. In certain embodiments, the polynucleotides as described herein are substantially pure.

Vectors and cells comprising the polynucleotides described herein are also provided.

IV. Methods of Use and Pharmaceutical Compositions

The present invention provides methods for inhibiting growth of a melanoma tumor using the DLL4 antagonists (e.g., antibodies) described herein. The present invention also provides methods for inhibiting melanoma metastases using the DLL4 antagonists (e.g., antibodies) described herein. The present invention provides methods of inhibiting growth of a melanoma tumor or metastases comprising administering a therapeutically effective amount of a DLL4 antagonist to a human subject in need thereof. The present invention provides methods of inhibiting growth of a melanoma tumor or metastases comprising administering a therapeutically effective amount of a DLL4 antagonist to a human subject in need thereof, wherein the DLL4 antagonist is an antibody that specifically binds an epitope within amino acids 27-217 of the extracellular domain of human DLL4 (SEQ ID NO:14). In some embodiments, the DLL4 antagonist is an antibody that binds an epitope comprising amino acids 66-73 (QAVVSPGP, SEQ ID NO:17) of human DLL4. In some embodiments, the DLL4 antagonist is an antibody that binds an epitope comprising amino acids 139-146 (LISKIAIQ, SEQ ID NO:18) of human DLL4. In certain embodiments, the DLL4 antagonist is an antibody that binds an epitope comprising amino acid 66-73 (QAVVSPGP, SEQ ID NO:17) and (LISKIAIQ, SEQ ID NO:18) of human DLL4. In some embodiments, the DLL4 antagonist is an antibody that binds an epitope formed by a combination of the N-terminal region of human DLL4 (SEQ ID NO:15) and the DSL region of human DLL4 DSL region (SEQ ID NO:16).

The present invention provides methods of inhibiting growth of a melanoma tumor comprising administering a therapeutically effective amount of a DLL4 antagonist to a human subject in need thereof, wherein the DLL4 antagonist is an antibody comprising: (a) a heavy chain CDR1 comprising TAYYIH (SEQ ID NO:1), a heavy chain CDR2 comprising YISCYNGATNYNQKFKG (SEQ ID NO:2), YISSYNGATNYNQKFKG (SEQ ID NO:3), or YISVYNGATNYNQKFKG (SEQ ID NO:4), and a heavy chain CDR3 comprising RDYDYDVGMDY (SEQ ID NO:5); and/or (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11).

The present invention also provides methods of inhibiting growth of a melanoma tumor comprising administering a therapeutically effective amount of a DLL4 antagonist to a human subject in need thereof, wherein the DLL4 antagonist is an antibody comprising: (a) a heavy chain variable region having at least about 90% sequence identity to SEQ ID NO:6, SEQ ID NO:7 or SEQ ID NO:8; and/or (b) a light chain variable region having at least about 90% sequence identity to SEQ ID NO:12. In some embodiments, the DLL4 antagonist is an antibody comprising: (a) a heavy chain variable region having at least about 90% sequence identity to SEQ ID NO:6, and (b) a light chain variable region having at least about 90% sequence identity to SEQ ID NO:12. In some embodiments, the DLL4 antagonist is an antibody comprising: (a) a heavy chain variable region having at least about 90% sequence identity to SEQ ID NO:7, and (b) a light chain variable region having at least about 90% sequence identity to SEQ ID NO:12. In some embodiments, the DLL4 antagonist is an antibody comprising: (a) a heavy chain variable region having at least about 90% sequence identity to SEQ ID NO:8, and (b) a light chain variable region having at least about 90% sequence identity to SEQ ID NO:12. In some embodiments, the DLL4 antagonist is an antibody comprising: (a) a heavy chain variable region consisting essentially of SEQ ID NO:6, and (b) a light chain variable region consisting essentially of SEQ ID NO:12. In some embodiments, the DLL4 antagonist is an antibody comprising: (a) a heavy chain variable region consisting essentially of SEQ ID NO:7, and (b) a light chain variable region consisting essentially of SEQ ID NO:12. In some embodiments, the DLL4 antagonist is an antibody comprising: (a) a heavy chain variable region consisting essentially of SEQ ID NO:8, and (b) a light chain variable region consisting essentially of SEQ ID NO:12.

In some embodiments of the methods described herein, the DLL4 antagonist is an antibody that comprises the same heavy and light chain variable regions as an antibody encoded by the plasmids deposited with ATCC having deposit no. PTA-8425 or PTA-8427. In some embodiments of the methods described herein, the DLL4 antagonist is an antibody that comprises the same heavy and light chain CDRs as antibody 21M18 produced by the hybridoma deposited with ATCC having deposit no. PTA-8670.

In certain embodiments of the methods described herein, the DLL4 antagonist is an antibody that competes for specific binding to the extracellular domain of human DLL4 with an antibody encoded by the plasmid deposited with ATCC having deposit no. PTA-8425. In some embodiments, the DLL4 antagonist is an antibody that competes for specific binding to human DLL4 with an antibody encoded by the plasmid deposited with ATCC having deposit no. PTA-8427. In some embodiments, the DLL4 antagonist is an antibody that competes for specific binding to human DLL4 with an antibody produced by the hybridoma deposited with ATCC having deposit no. PTA-8670. In some embodiments, the DLL4 antagonist is an antibody that competes for specific binding to the extracellular domain of human DLL4 with antibody 21M18, 21M18 H7L2 or 21M18 H9L2.

In certain embodiments of the methods described herein, the melanoma tumor comprises a mutation in the MAPK pathway. The MAPK pathway comprises a cascade of interacting proteins. For example, tyrosine kinase receptors at the cell surface are activated by extracellular ligands. The receptors become phosphorylated on tyrosine residues. Docking proteins bind to the phosphotyrosine residues of the activated receptors. The docking proteins form complexes with other proteins that promote the activation of members of the Ras subfamily (e.g., N-ras, K-ras or H-ras). In a series of steps, activated Ras activates the protein kinase activity of Raf kinase, Raf kinase phosphorylates and activates MEK, and MEK phosphorylates and activates a mitogen-activated protein kinase (MAPK also known as ERK). MAPK regulates the activities of several transcription factors which affect a wide variety of cellular functions. Mutations in proteins of the MAPK pathway have been shown to dysregulate the pathway and may lead to oncogenesis.

In certain embodiments of the methods described herein, the melanoma tumor comprises wild-type Raf, mutant Raf, wild-type Ras, mutant Ras, wild-type c-Kit and/or mutant c-Kit. In some embodiments, the melanoma comprises a wild-type B-raf. In some embodiments, the melanoma comprises a B-raf mutation. In some embodiments, the B-raf mutation is an activating mutation. In certain embodiments, the B-raf mutation is in amino acid position 600. In some embodiments, the B-raf mutation is a valine to glutamate mutation at amino acid 600 (B-raf$^{V600E}$). In certain embodiments, the B-raf mutation is a valine to lysine mutation at amino acid 600 (B-raf$^{V600K}$).

In some embodiments of the methods described herein, a melanoma tumor is substantially non-responsive to at least one B-raf inhibitor. In some embodiments, a melanoma tumor comprising a wild-type B-raf is substantially non-responsive to at least one B-raf inhibitor. In some embodiments, the B-raf inhibitor is a small molecule compound inhibitor. In some embodiments, the B-raf inhibitor is PLX4032 or PLX4720. In some embodiments, the B-raf inhibitor is sorafenib. In some embodiments, the B-raf inhibitor is GDC-0879.

In certain embodiments, the method of inhibiting growth of a melanoma tumor comprises contacting melanoma cells with a DLL4 antagonist (e.g., an antibody) in vitro. For example, an immortalized melanoma cell line or a cancer cell line that expresses DLL4 on the cell surface is cultured in medium to which is added the DLL4 antagonist (e.g., antibody or other agent) to inhibit melanoma cell growth. In some embodiments, melanoma cells are isolated from a patient sample (e.g., a tissue biopsy, pleural effusion, or blood sample), and cultured in medium to which is added a DLL4 antagonist to inhibit melanoma cell growth.

In some embodiments, the method of inhibiting growth of a melanoma tumor comprises contacting the melanoma or melanoma cells with a DLL4 antagonist (e.g., an antibody) in vivo. In certain embodiments, contacting a melanoma or melanoma cells with a DLL4 antagonist is undertaken in an animal model. For example, DLL4 antagonists are administered to immunocompromised mice (e.g., NOD/SCID mice) that have xenograft melanoma tumors expressing DLL4. After administration of DLL4 antagonists, the mice are observed for inhibition of melanoma growth. In some embodiments, melanoma cells are isolated from a patient sample such as, for example, a tissue biopsy, pleural effusion, or blood sample and injected into immunocompromised mice that are then administered a DLL4 antagonist to inhibit tumor growth. In some embodiments, cancer stem cells or tumor initiating cells are isolated from a patient melanoma sample such as, for example, a tissue biopsy, pleural effusion, or blood sample and injected into immunocompromised mice that are then administered a DLL4 antagonist to inhibit tumor growth. In some embodiments, the DLL4 antagonist is administered at the same time or shortly after introduction of cells into the animal to prevent tumor growth. In some embodiments, the DLL4 antagonist is administered as a therapeutic after the cells have grown to a tumor of specified size. In certain embodiments, the cells are injected subcutaneously into the mice. In certain embodiments, the cells are injected intradermally or orthotopically into the mice. In some embodiments, the cells are injected into human skin engrafted into the back of a mouse.

The present invention further provides methods of inhibiting growth of a melanoma tumor comprising administering a therapeutically effective amount of a DLL4 antagonist as described herein to a human subject in need thereof, wherein the melanoma is substantially non-responsive to at least one B-raf inhibitor. In some embodiments, the tumor that is substantially non-responsive to at least one B-raf inhibitor comprises a wild-type B-raf.

In certain embodiments, the method of inhibiting growth of a melanoma tumor comprises administering to a subject a therapeutically effective amount of a DLL4 antagonist. In certain embodiments, the subject is a human. In some embodiments, the melanoma is cutaneous. In some embodiments, the melanoma is extracutaneous. In certain embodiments, the melanoma has metastasized. In certain embodiments, the subject has had at least one primary tumor removed. In some embodiments, the DLL4 antagonist is an antibody. In some embodiments, the DLL4 antagonist is a humanized form of antibody 21M18. In some embodiments, the DLL4 antagonist is antibody 21M18 H7L2. In some embodiments, the DLL4 antagonist is antibody 21M18 H9L2.

In certain embodiments, the melanoma tumor expresses DLL4 to which the DLL4 antagonist or antibody binds. In certain embodiments, the melanoma tumor over-expresses DLL4. In certain embodiments, the melanoma tumor expresses a Notch receptor (e.g., Notch1, Notch2, Notch3, and/or Notch4) with which DLL4 interacts.

In certain embodiments of the methods described herein, the melanoma is cutaneous melanoma, extracutaneous melanoma, superficial spreading melanoma, malignant melanoma, nodular malignant melanoma, nodular melanoma, polypoid melanoma, acral lentiginous melanoma, lentiginous malignant melanoma, lentigo maligna melanoma, mucosal lentignous melanoma, mucosal melanoma, soft-tissue melanoma, ocular melanoma, desmoplastic melanoma, or metastatic malignant melanoma. In some embodiments, the melanoma is a primary melanoma tumor. In some embodiments, the primary melanoma tumor has metastasized. In some embodiments, the melanoma is metastatic melanoma.

The present invention further provides methods for treating melanoma using the DLL4 antagonists described herein. In certain embodiments, the melanoma is characterized by cells expressing DLL4 to which the DLL4 antagonist (e.g., antibody) binds. In certain embodiments, the melanoma is characterized by cells expressing Notch receptors, wherein the DLL4 antagonist (e.g., an antibody) interferes with DLL4-induced Notch activation and/or signaling. In some embodiments, the DLL4 antagonist binds to DLL4 and inhibits or reduces growth of the melanoma. In some embodiments, the DLL4 antagonist binds to DLL4 and inhibits or reduces recurrence of growth of the melanoma. In some embodiments, the DLL4 antagonist binds to DLL4, interferes with DLL4/Notch interactions and inhibits or reduces growth of the melanoma. In some embodiments, the DLL4 antagonist binds to DLL4, inhibits Notch signaling and inhibits or reduces growth of the melanoma. In certain embodiments, the DLL4 antagonist binds to DLL4 and inhibits or reduces angiogenesis. In certain embodiments, the inhibition and/or reduction of angiogenesis inhibits or reduces growth of the melanoma. In some embodiments, the DLL4 antagonist binds to DLL4 and promotes aberrant angiogenesis. In some embodiments, the DLL4 antagonist binds to DLL4 and promotes unproductive angiogenesis. In certain embodiments, the aberrant angiogenesis or the unproductive angiogenesis inhibits or reduces growth of the melanoma.

The present invention provides methods of treating melanoma in a human subject, comprising: (a) determining if the subject has a melanoma comprising a mutation in the MAPK pathway, and (b) administering to the subject (e.g., a subject in need of treatment) a therapeutically effective amount of a DLL4 antagonist described herein. In some embodiments, the MAPK pathway comprises a mutation in B-raf. In some embodiments, the MAPK pathway comprises a wild-type B-raf. In certain embodiments, the subject has a primary melanoma. In certain embodiments, the subject has had at least one melanoma tumor removed. In some embodiments, the melanoma has metastasized. In some embodiments, the DLL4 antagonist is an antibody that specifically binds the extracellular domain of human DLL4. In some embodiments, the DLL4 antagonist is an antibody that specifically binds an epitope within amino acids 27-217 of the extracellular domain of human DLL4. In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12. In some embodiments, the DLL4 antagonist is antibody 21M18. In certain embodiments, the DLL4 antagonist is a humanized version of antibody 21M18. In some embodiments, the DLL4 antagonist is antibody 21M18 H7L2. In some embodiments, the DLL4 antagonist is antibody 21M18 H9L2.

The present invention further provides methods of treating melanoma in a human subject, comprising: (a) selecting a subject for treatment based, at least in part, on the subject having a melanoma that comprises a wild-type B-raf or a B-raf mutation, and (b) administering to the subject a therapeutically effective amount of a DLL4 antagonist described herein. In certain embodiments, the subject has a primary tumor. In certain embodiments, the subject has had at least one melanoma tumor removed. In some embodiments, the melanoma has metastasized. In some embodiments, the DLL4 antagonist is an antibody that specifically binds the extracellular domain of human DLL4. In some embodiments, the DLL4 antagonist is an antibody that specifically binds an epitope within amino acids 27-217 of the extracellular domain of human DLL4. In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12. In some embodiments, the DLL4 antagonist is antibody 21M18. In certain embodiments, the DLL4 antagonist is a humanized version of antibody 21M18. In some embodiments, the DLL4 antagonist is antibody 21M18 H7L2. In some embodiments, the DLL4 antagonist is antibody 21M18 H9L2.

The present invention further provides methods of treating melanoma in a human subject, comprising: (a) identifying a subject that has a melanoma comprising a wild-type B-raf, and (b) administering to the subject a therapeutically effective amount of a DLL4 antagonist described herein. In some embodiments, the melanoma comprises a wild-type B-raf that is substantially non-responsive to at least one B-raf inhibitor. In some embodiments, the B-raf inhibitor is a small molecule compound inhibitor. In some embodiments, the B-raf inhibitor is PLX4032 or PLX4720. In certain embodiments, the subject has a primary tumor. In certain embodiments, the subject has had at least one primary tumor removed. In certain embodiments, the melanoma has metastasized. In certain embodiments, the DLL4 antagonist is an antibody that specifically binds the extracellular domain of human DLL4. In some embodiments, the DLL4 antagonist is an antibody that specifically binds an epitope within amino acids 27-217 of the extracellular domain of human DLL4. In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12. In some embodiments, the DLL4 antagonist is antibody 21M18. In some embodiments, the DLL4 antagonist is a humanized version of antibody 21M18. In some embodiments, the DLL4 antagonist is antibody 21M18 H7L2. In some embodiments, the DLL4 antagonist is antibody 21M18 H9L2.

The present invention further provides methods of treating melanoma in a human subject, comprising: (a) determining that the subject's melanoma is substantially non-responsive to at least one B-raf inhibitor, and (b) administering to the subject a therapeutically effective amount of a DLL4 antagonist described herein. In some embodiments, the B-raf inhibitor is a small molecule compound inhibitor. In some embodiments, the B-raf inhibitor is PLX4032 or PLX4720. In certain embodiments, the subject has had at least one primary tumor removed. In certain embodiments, the melanoma has metastasized. In some embodiments, the DLL4 antagonist is an antibody that specifically binds the extracellular domain of human DLL4. In some embodiments, the DLL4 antagonist is an antibody that specifically binds an epitope within amino acids 27-217 of the extracellular domain of human DLL4. In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12. In some embodiments, the DLL4 antagonist is antibody 21M18. In some embodiments, the DLL4 antagonist is a humanized version of antibody 21M18. In some embodiments, the DLL4 antagonist is antibody 21M18 H7L2. In some embodiments, the DLL4 antagonist is antibody 21M18 H9L2.

The present invention further provides methods of treating melanoma in a human subject, comprising: (a) selecting a subject for treatment based, at least in part, on the subject having a melanoma that is substantially non-responsive to at least one B-raf inhibitor, and (b) administering to the subject a therapeutically effective amount of a DLL4 antagonist described herein. In some embodiments, the B-raf inhibitor is a small molecule compound inhibitor. In some embodiments, the B-raf inhibitor is PLX4032 or PLX4720. In certain embodiments, the subject has had at least one primary tumor removed. In certain embodiments, the melanoma has metastasized. In some embodiments, the DLL4 antagonist is an antibody that specifically binds the extracellular domain of human DLL4. In some embodiments, the DLL4 antagonist is an antibody that specifically binds an epitope within amino acids 27-217 of the extracellular domain of human DLL4. In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12. In some embodiments, the DLL4 antagonist is antibody 21M18. In some embodiments, the DLL4 antagonist is a humanized version of antibody 21M18. In some embodiments, the DLL4 antagonist is antibody 21M18 H7L2. In some embodiments, the DLL4 antagonist is antibody 21M18 H9L2.

The present invention further provides methods of treating melanoma in a human subject, comprising: (a) identifying a subject that has a melanoma that is substantially non-responsive to at least one B-raf inhibitor, and (b) administering to the subject a therapeutically effective amount of a DLL4 antagonist described herein. In some embodiments, the melanoma comprises a wild-type B-raf. In some embodiments, the B-raf inhibitor is a small molecule compound inhibitor. In some embodiments, the B-raf inhibitor is PLX4032 or PLX4720. In certain embodiments, the subject has had at least one primary tumor removed. In certain embodiments, the melanoma has metastasized. In some embodiments, the DLL4 antagonist is an antibody that specifically binds the extracellular domain of human DLL4. In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12. In some embodiments, the DLL4 antagonist is antibody 21M18. In some embodiments, the DLL4 antagonist is antibody 21M18 H7L2. In some embodiments, the DLL4 antagonist is antibody 21M18 H9L2.

The present invention further provides methods of selecting a human subject for treatment with a DLL4 antagonist. In some embodiments, the methods comprise determining if the subject has (a) a melanoma comprising a wild-type B-raf or (b) a melanoma that is substantially non-responsive to at least one B-raf inhibitor, wherein if the subject has (a) and/or (b), the subject is selected for treatment with a DLL4 antagonist described herein. In some embodiments, the B-raf inhibitor is a small molecule compound inhibitor. In some embodiments, the B-raf inhibitor is PLX4032 or PLX4720. In certain embodiments, the subject has had at least one primary tumor removed. In certain embodiments, the melanoma has metastasized. In some embodiments, the DLL4 antagonist is an antibody that specifically binds the extracellular domain of human DLL4. In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12. In some embodiments, the DLL4 antagonist is antibody 21M18. In some embodiments, the DLL4 antagonist is antibody 21M18 H7L2. In some embodiments, the DLL4 antagonist is antibody 21M18 H9L2.

The present invention also provides methods of treating a human subject who has a melanoma comprising a wild-type B-raf, comprising administering to the subject a therapeutically effective amount of a DLL4 antagonist described herein. In some embodiments, the methods comprise treating a human subject who has a melanoma which is substantially non-responsive to at least one B-raf inhibitor, comprising administering to the subject a therapeutically effective amount of a DLL4 antagonist described herein. In some embodiments, the DLL4 antagonist is an antibody comprising: (a) a heavy chain CDR1 comprising TAYYIH (SEQ ID NO:1), a heavy chain CDR2 comprising YISSYN- GATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12.

The sequence of wild-type human B-raf is known in the art, (e.g., Accession No. NP_004324.2 and SEQ ID NO:19). Methods for determining whether a melanoma comprises a wild-type B-raf or a B-raf mutation can be undertaken by analyzing the nucleotide sequence encoding the B-raf protein, by analyzing the amino acid sequence of the B-raf protein, or by analyzing the characteristics of a putative B-raf mutant protein.

Methods for detecting a wild-type B-raf or a B-raf mutation are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, digital PCR, PCR sequencing, mutant allele-specific PCR amplification (MASA) assays, direct sequencing, "Nex-Gen" sequencing, 454 sequencing, primer extension reactions, electrophoresis, oligonucleotide ligation assays, hybridization assays, TaqMan assays, SNP genotyping assays, high resolution melting assays and microarray analyses. In some embodiments, samples may be evaluated for B-raf mutations by real-time PCR. In real-time PCR, fluorescent probes specific for the most common mutations (e.g., mutation in codon encoding amino acid 600) are used. When a mutation is present, the probe binds and fluorescence is detected. In some embodiments, B-raf mutations may be identified using a direct sequencing method of specific regions in the B-raf gene. This technique will identify all possible mutations in the region sequenced.

Methods for detecting a mutation in a B-raf protein are known by those of skill in the art. These methods include, but are not limited to, detection of a B-raf mutant using a binding agent (e.g., an antibody) specific for the mutant protein, protein electrophoresis and Western blotting, and direct peptide sequencing.

Methods for determining whether a melanoma comprises a wild-type B-raf or a B-raf mutation can use a variety of samples. In some embodiments, the sample is taken from a subject having a melanoma tumor. In some embodiments, the sample is taken from a subject having a melanoma that is substantially non-responsive to at least one B-raf inhibitor. In some embodiments, the sample is a fresh sample. In some embodiments, the sample is a frozen sample. In some embodiments, the sample is a formalin-fixed paraffin-embedded sample. In some embodiments, the sample is processed to a cell lysate. In some embodiments, the sample is processed to DNA or RNA.

The invention also provides a method of inhibiting Notch signaling in a cell comprising contacting the cell with an effective amount of a DLL4 antagonist described herein. In certain embodiments, the cell is a melanoma tumor cell. In some embodiments, the melanoma tumor cell is substantially non-responsive to at least one B-raf inhibitor. In certain embodiments, the method is an in vivo method wherein the step of contacting the cell with the DLL4 antagonist comprises administering a therapeutically effective amount of the DLL4 antagonist to the subject. In some embodiments, the method is an in vitro or ex vivo method. In certain embodiments, the DLL4 antagonist interferes with Notch signaling. In certain embodiments, the DLL4 antagonist interferes with a DLL4/Notch interaction. In certain embodiments, the Notch signaling is signaling by Notch1, Notch2, Notch3, and/or Notch4. In some embodiments, the DLL4 antagonist is an antibody. In some embodiments, the DLL4 antagonist is an antibody comprising: (a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and (b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11). In some embodiments, the DLL4 antagonist is an antibody comprising a heavy chain variable region having at least 90% sequence identity to SEQ ID NO:7 and a light chain variable region having at least 90% sequence identity to SEQ ID NO:12. In some embodiments, the DLL4 antagonist is antibody 21M18, 21M18 H7L2 or 21M18 H9L2.

In addition, the invention provides a method of reducing the tumorigenicity of a melanoma in a subject, comprising administering a therapeutically effective amount of a DLL4 antagonist described herein to the subject. In some embodiments, the melanoma comprises a wild-type B-raf. In some embodiments, the melanoma comprises at least one mutation in the MAPK pathway. In some embodiments, the melanoma comprises at least one B-raf mutation. In certain embodiments, the melanoma comprises cancer stem cells or tumor initiating cells. In some embodiments, the cancer stem cells or tumor initiating cells are substantially non-responsive to at least one B-raf inhibitor. In certain embodiments, the frequency of cancer stem cells or tumor initiating cells in the melanoma is reduced by administration of the DLL4 antagonist. Thus, the invention also provides a method of reducing the frequency of cancer stem cells or tumor initiating cells in a melanoma, comprising contacting the melanoma with an effective amount of a DLL4 antagonist (e.g., an anti-DLL4 antibody).

In addition, the invention provides methods of inhibiting metastasis of a melanoma tumor in a subject, comprising administering a therapeutically effective amount of a DLL4 antagonist described herein to the subject. The invention provides methods of inhibiting metastasis of a melanoma tumor, comprising contacting the melanoma tumor with an effective amount of a DLL4 antagonist (e.g., an anti-DLL4 antibody).

The invention also provides a method of treating a disease or disorder in a subject, wherein the disease or disorder is characterized by an increased level of stem cells and/or tumor initiating cells. In some embodiments, the stem cells and/or tumor initiating cells comprise a wild-type B-raf. In some embodiments, the stem cells and/or tumor initiating cells comprise at least one mutation in the MAPK pathway. In some embodiments, the stem cells and/or tumor initiating cells comprise at least one B-raf mutation. In some embodiments, the treatment methods comprise administering a therapeutically effective amount of the DLL4 antagonist, polypeptide, or antibody to the subject.

The present invention further provides pharmaceutical compositions comprising one or more of the DLL4 antagonists described herein. In certain embodiments, the pharmaceutical composition further comprises a pharmaceutically acceptable vehicle. These pharmaceutical compositions find use in inhibiting growth of a melanoma tumor and treating melanoma in a subject (e.g., a human patient). In some embodiments, the pharmaceutical compositions find use in inhibiting metastatic melanoma. In some embodiments, the methods described herein comprise administering a pharmaceutical composition comprising any of the DLL4 antagonists described herein.

In certain embodiments, formulations are prepared for storage and use by combining a purified antibody or agent of the present invention with a pharmaceutically acceptable vehicle (e.g., a carrier or excipient). Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 21st Edition, University of the Sciences in Philadelphia, 2005).

In certain embodiments, the anti-DLL4 antagonist or antibody can be prepared for use at a concentration of 10 mg/mL in a solution of histidine, sodium chloride, sucrose, and polysorbate 20. In certain embodiments, the anti-DLL4 antagonist or antibody can be prepared for use at a concentration of 10 mg/mL in a solution of 50 mM histidine, 100 mM sodium chloride, 45 mM sucrose, and 0.01% (w/v) polysorbate 20, and the pH adjusted to 6.0.

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The antibodies or agents described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 21st Edition, University of the Sciences in Philadelphia, 2005.

In certain embodiments, pharmaceutical formulations include DLL4 antagonists (e.g., an antibody) of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations can be produced. Suitable examples of sustained-release preparations include semi-permeable matrices of solid hydrophobic polymers containing the DLL4 antagonist (e.g., an antibody), where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In certain embodiments, in addition to administering a DLL4 antagonist (e.g., an antibody), the method or treatment further comprises administering at least one additional therapeutic agent. An additional therapeutic agent can be administered prior to, concurrently with, and/or subsequently to, administration of the DLL4 antagonist. Pharmaceutical compositions comprising the DLL4 antagonist and the additional therapeutic agent(s) are also provided. In some embodiments, the at least one additional therapeutic agent comprises 1, 2, 3, or more additional therapeutic agents.

Combination therapy with at least two therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects. Combination therapy may decrease the likelihood that resistant cancer cells will develop. Combination therapy may allow for one therapeutic agent to target tumorigenic cancer stem cells and a second therapeutic agent to target nontumorigenic cells.

It will be appreciated that the combination of a DLL4 antagonist and an additional therapeutic agent may be administered in any order or concurrently. In some embodiments, the DLL4 antagonist will be administered to patients that have previously undergone treatment with a second therapeutic agent. In certain other embodiments, the DLL4 antagonist and a second therapeutic agent will be administered substantially simultaneously or concurrently. For example, a subject may be given the DLL4 antagonist (e.g., an antibody) while undergoing a course of treatment with a second therapeutic agent (e.g., chemotherapy). In certain embodiments, the DLL4 antagonist will be administered within 1 year of the treatment with a second therapeutic agent. In certain alternative embodiments, the DLL4 antagonist will be administered within 10, 8, 6, 4, or 2 months of any treatment with a second therapeutic agent. In certain other embodiments, the DLL4 antagonist will be administered within 4, 3, 2, or 1 weeks of any treatment with a second therapeutic agent. In some embodiments, the DLL4 antagonist will be administered within 5, 4, 3, 2, or 1 days of any treatment with a second therapeutic agent. It will further be appreciated that the two (or more) agents or treatment may be administered to the subject within a matter of hours or minutes (i.e., substantially simultaneously).

Useful classes of therapeutic agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, antimitotic agents, taxanes, topoisomerase inhibitors, vinca alkaloids, angiogenesis inhibitors, protein kinase inhibitors, or the like. In certain embodiments, the second therapeutic agent is a protein kinase inhibitor, a taxane, a topoisomerase inhibitor, or an angiogenesis inhibitor.

Therapeutic agents that may be administered in combination with the DLL4 antagonists include chemotherapeutic agents. Thus, in some embodiments, the method or treatment involves the combined administration of a DLL4 antagonist or antibody of the present invention and a chemotherapeutic agent or cocktail of multiple different chemotherapeutic agents. Treatment with an antibody can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

Chemotherapeutic agents useful in the instant invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; erlotinib (TARCEVA); gallium nitrate; hydroxyurea; imatanib mesylate (GLEEVEC); lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; sorafenib (NEXAVAR); spirogermanium; sunitinib (SUTENT); tenuazonic acid; thalidomide; triaziquone; 2,2', 2"-trichlorotriethylamine; urethan; vindesine; dacarbazine (DITC); temozolomide; mannomustine; mitobronitol; mitolactol; pipobroman; gacytosine; arabinoside ("Ara-C"); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. In some embodiments, the additional therapeutic agent is dacarbazine (DITC). In some embodiments, the additional therapeutic agent is temozolomide. In some embodiments, the additional therapeutic agent is carboplatin. In some embodiments, the additional therapeutic agents are carboplatin and paclitaxel.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCL, daunorubicin citrate, mitoxantrone HCl, actinomycin D, etoposide, topotecan HCl, teniposide (VM-26), and irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, the additional therapeutic agent is paclitaxel.

In certain embodiments, the chemotherapeutic agent is a protein kinase inhibitor. Protein kinases are involved in a significant number of important signaling pathways, and over-expressed or mutant protein kinases may be involved in oncogenic processes. Protein kinase inhibitors include, but are not limited to, imatanib mesylate (GLEEVEC), sorafenib (NEXAVAR), sunitinib (SUTENT), erlotinib (TARCEVA), nilotinib, dasatinib, lapatinib, gefitinbib, pazopanib, mubritinib, vandetanib, PLX4032 and PLX4720. In some embodiments, the additional therapeutic agent is PLX4032. In some embodiments, the additional therapeutic agent is PLX4720. In some embodiments, the additional therapeutic agent is sorafenib.

In certain embodiments, the treatment involves the combined administration of a DLL4 antagonist (e.g. an antibody) of the present invention and radiation therapy. Treatment with the DLL4 antagonist can occur prior to, concurrently with, or subsequent to administration of radiation therapy. Radiation therapy can occur prior to, and/or subsequent to, surgical removal or excision of the melanoma tumor. Dosing schedules for such radiation therapy can be determined by the skilled medical practitioner.

In some embodiments, a second therapeutic agent comprises an antibody. Thus, treatment can involve the combined administration of a DLL4 antagonist (e.g. an antibody) of the present invention with other antibodies against additional tumor-associated antigens including, but not limited to, antibodies that bind to ErbB2, HER2, EGFR, Jagged, Notch and/or VEGF. In certain embodiments, the additional therapeutic is an anti-Notch antibody. Exemplary anti-Notch antibodies, are described, for example, in U.S. Patent Application Publication No. 2008/0131434. In certain embodiments, the additional therapeutic agent is an antibody that is an angiogenesis inhibitor (e.g., an anti-VEGF antibody). In certain embodiments, the additional therapeutic agent is bevacizumab (AVASTIN) or ranibizumab.

In some embodiments, the treatment can involve the combined administration of a DLL4 antagonist (e.g. an antibody) of the present invention with a second antibody that can activate the immune system. In some embodiments, the second antibody binds cytotoxic T lymphocyte-associated antigen 4 (CTLA-4). In certain embodiments, the second antibody is ipilimumab. In certain embodiments, the second antibody is tremlimumab.

Furthermore, treatment with the DLL4 antagonists described herein can include combination treatment with one or more cytokines (e.g., lymphokines, interleukins, tumor necrosis factors, and/or growth factors). In some embodiments, the additional therapeutic agent is interferon alpha, interferon-alpha, pegylated interferon-alpha or interleukin-2. In certain embodiments, the additional therapeutic agent is interferon-alpha. In certain embodiments, the additional therapeutic agent is interleukin-2.

Combined administration can include co-administration, either in a single pharmaceutical formulation or using separate formulations, or consecutive administration in either order but generally within a time period such that all active agents can exert their biological activities simultaneously.

In some embodiments, any of the combination treatments described herein can be accompanied by surgical removal of tumors, cancer cells or any other therapy deemed necessary by a treating physician.

For the treatment of melanoma, the appropriate dosage of an DLL4 antagonist (e.g., an antibody) of the present invention depends on the type or stage of melanoma to be treated, the severity and course of the melanoma, whether the melanoma has metastasized, the responsiveness of the melanoma, whether the DLL4 antagonist or antibody is administered for therapeutic or preventative purposes, previous therapy, the patient's clinical history, and so on, all at the discretion of the treating physician. The DLL4 antagonist or antibody can be administered one time or over a series of treatments lasting from several days to several months, or until a cure is effected or a diminution of the disease state is achieved (e.g., reduction in melanoma tumor size or reduction in metastases). Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 µg to 100 mg per kg of body weight, and can be given once or more daily, weekly, monthly or yearly. In certain embodiments, the DLL4 antagonist or antibody is given once every two weeks or once every three weeks. In certain embodiments, the dosage of the DLL4 antagonist or antibody is from about 0.1 mg to about 20 mg per kg of body weight. The treating physician can estimate repetition rates for dosing based on measured residence times and concentrations of the drug in bodily fluids or tissues.

The present invention provides methods of inhibiting growth of a melanoma tumor in a subject and methods of treating a human subject who has a melanoma tumor using the DLL4 antagonists (e.g., antibodies) described herein. In some embodiments, the methods described herein comprise: (a) administering to the subject an initial dose of a DLL4 antagonist; and (b) administering to the subject at least one subsequent dose of the DLL4 antagonist. In some embodiments, the methods comprise: (a) administering to the subject an initial dose of a DLL4 antagonist; (b) administering to the subject at least two subsequent doses of the DLL4 antagonist at a first frequency; and (c) administering to the subject at least one additional subsequent dose of the DLL4 antagonist at a second frequency. Achieving higher blood levels of a DLL4 antagonist at earlier timepoints may lead to more subjects with stabilized disease, partial responses or complete responses. Regimens that allow for this include higher initial doses, followed by subsequent doses at reduced levels, higher initial doses and increased frequency of dosing at early timepoints, and/or initial doses at increased frequency of dosing at early timepoints. In some embodiments, a regimen may include a higher initial dose and then lower doses at least 2 weeks later. In some embodiments, a regimen may include a higher initial dose and then lower doses at least 3 weeks later.

In some embodiments, the methods comprise administration of an initial dose of a DLL4 antagonist of about 10 mg/kg. In some embodiments, the DLL4 antagonist is delivered as an intravenous infusion.

According to the invention, the initial dose or doses is/are followed by subsequent doses of equal or smaller amounts of DLL4 antagonist at intervals sufficiently close to maintain the antagonist at or above an efficacious target level. In some embodiments, the initial dose may be referred to as a "loading dose". In some embodiments, the subsequent doses may be referred to as "maintenance doses". The intervals between doses may be, but are not limited to, 1 week or less, every 2 weeks, every 3 weeks, or every 4 weeks. In some embodiment, the higher initial dose or an increased frequency of administration in the early weeks of treatment has the advantage of increased efficacy by reaching a target serum drug concentration earlier in treatment.

In some embodiments, the initial dose of the DLL4 antagonist is about 5 mg/kg, about 10 mg/kg, about 12.5 mg/kg, about 15 mg/ml or about 20 mg/kg. In some embodiments, the subsequent doses are 5 mg/kg delivered once per week, once every other week or once every three weeks. In some embodiments, the subsequent doses are about 10 mg/kg delivered once per week, once every other week, or once every three weeks. In some embodiments, the first two subsequent doses are about 10 mg/kg delivered once per week and subsequent doses are about 10 mg/kg delivered once every other week. In some embodiments, the first two subsequent doses are about 10 mg/kg delivered once per week and subsequent doses are about 10 mg/kg delivered once every three weeks. In some embodiments, the first two subsequent doses are about 5 mg/kg delivered once per week and subsequent doses are about 5 mg/kg delivered once every other week. In some embodiments, the first two subsequent doses are about 5 mg/kg delivered once per week and subsequent doses are about 5 mg/kg delivered once every three weeks. The choice of delivery method for the initial and subsequent doses is made according to the ability of the animal or human subject to tolerate introduction of the DLL4 antagonist into the body.

EXAMPLES

Example 1

Evaluation of Melanomas for B-Raf Mutations

A collection of xenografts have been established which are derived from patient melanoma tumors. The tumors were expanded by in vivo passage in NOD-SCID mice without any intervening in vitro cell culture. Genomic DNA samples were isolated from primary and passaged tumors using a Genomic DNA Extraction Kit (Bioneer Inc., Alameda, Calif.) following the manufacturers' instructions. The quality of the isolated DNA was checked by visualizing the DNA samples on a 1% agarose gel or a 0.8% E-Gel (Invitrogen Corporation, Carlsbad, Calif.). The DNA was confirmed to be intact by the presence of an approximately 20 kb size band with little or no visible degradation. The purified genomic DNA samples were sent to SeqWright Technologies, (Houston, Tex.) for nucleotide sequence analysis. The B-raf gene was obtained by amplifying genomic DNA samples with the Repli-G Mini Kit (Qiagen, Valencia, Calif.) followed by PCR amplification and purification. The nucleotide sequence of the B-raf gene for each tumor was obtained using an ABI 3730xL DNA Sequencer (Applied Biosystems, Foster City, Calif.).

Of the six melanoma tumors evaluated, 3 had a wild type B-raf gene (M3, M4 and M6) and 3 had a mutant B-raf gene (M2, M5 and M8) as compared to the human B-raf sequence (see e.g., Accession No. NP_004324.2). Three melanoma tumors had a mutation in codon 600, a valine to glutamate mutation (V600E). The B-raf valine to glutamate mutation is a known activating mutation.

TABLE 1

| | Tumor | | | | | | |
|---|---|---|---|---|---|---|---|
| | M2 | M3 | M4 | M5 | M6 | M7 | M8 |
| B-raf | Mut | WT | WT | Mut | WT | ND | Mut |

WT = wild-type B-raf gene
ND = Not Determined

Example 2

Inhibition of Melanoma Tumor Growth In Vivo by Anti-DLL4 Antibodies

NOD/SCID mice were purchased from Harlan Laboratories (Indianapolis, Ind.) and maintained under specific pathogen-free conditions and provided with sterile food and water ad libitum. The animals were housed in a U.S. Department of Agriculture-registered facility in accordance with NIH guidelines for the care and use of laboratory animals. The mice were allowed to acclimate for several days prior to the start of each study.

In general, tumor cells from a patient sample that have been passed as a xenograft in mice were prepared for injection into experimental animals. Tumor tissue was removed under sterile conditions, cut up into small pieces, minced completely using sterile blades, and single cell suspensions obtained by enzymatic digestion and mechanical disruption. Specifically, tumor pieces were mixed with ultra-pure collagenase III in culture medium and incubated at 37° C. for 1-4 hours. Digested cells were filtered through nylon mesh and washed in Hank's buffered saline solution (HBSS) containing 2% heat-inactivated calf serum and 25 mM HEPES (pH 7.4). Tumor cells were used immediately or frozen in aliquots to be used upon thawing in future experiments.

Dissociated M2, M3, M4 and M5 melanoma tumor cells (50,000 cells) were injected subcutaneously into the flanks of 6-8 week old NOD/SCID mice. Tumors were allowed to grow until the average tumor size was approximately 150 mm$^3$. The animals were randomized (n=10 per group) and treated with a control antibody (anti-lysozyme antibody LZ-1; -■-) or an anti-DLL4 antibody (-▼-). The "anti-DLL4 antibody" was a 1:1 mixture of (i) anti-human DLL4 antibody 21M18 H7L2 and (ii) anti-mouse DLL4 antibody 21R30. Antibodies were administered intraperitoneally at 15 mg/kg once a week. The 15 mg/kg dose of the anti-DLL4 antibody refers to the antibody mixture. Tumor growth was measured on the indicated days after treatment with electronic calipers.

Figure 1D:
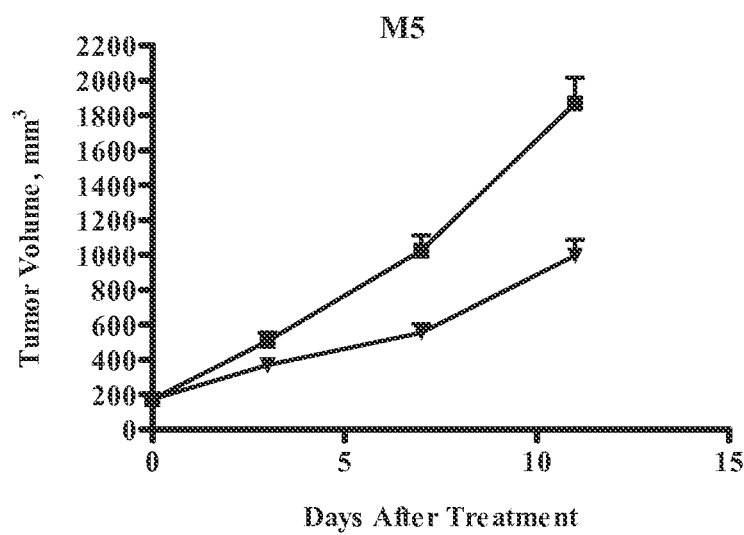

Anti-DLL4 antibody inhibited melanoma tumor growth in two wild-type B-raf tumors, M3 (FIG. 1B) and M4 (FIG. 1C) as well as in two B-raf mutant tumors, M2 (FIG. 1A) and M5 (FIG. 1D).

Example 3

Inhibition of Melanoma Tumor Growth In Vivo by Anti-DLL4 Antibodies in Combination with a Chemotherapeutic Agent Luciferase-labeled M2 melanoma tumor cells (40,000 cells) were injected intradermally (orthotopic model) into 6-8 week old NOD/SCID mice. Tumor volumes were measured by determining the bioluminescent signal using an IVIS Imaging System (Caliper LifeSciences, Mountain View, Calif.). Tumors were allowed to grow until the average bioluminescent signal was approximately $2 \times 10^8$ photons/sec. The animals were randomized into four groups (n=10 per group) and treated with a control antibody (anti-lysozyme antibody LZ-1, -■-), an anti-DLL4 antibody (-▲-), taxol (-○-), or a combination of taxol and anti-DLL4 antibody (-▼-). The anti-DLL4 antibody was a 1:1 mixture of anti-human DLL4 antibody and anti-mouse DLL4 antibody as described above. Antibodies were administered at 15 mg/kg once a week and taxol was administered at 10 mg/kg once a week. Both agents were administered intraperitoneally. Tumor growth was measured by imaging the mice on the indicated days.

Figure 2A:
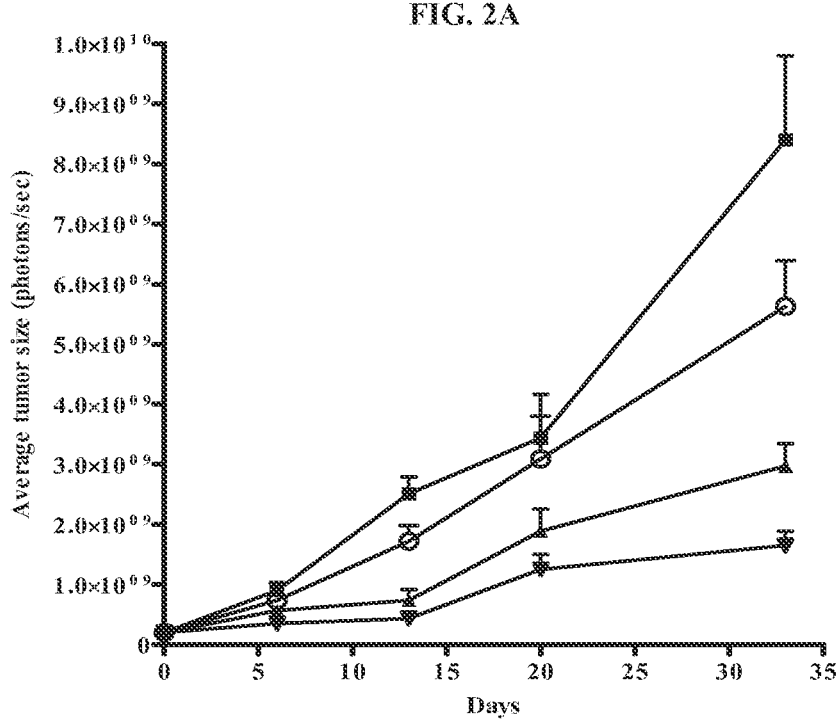
FIG. 2. Inhibition of melanoma tumor growth in vivo by anti-DLL4 antibodies in combination with taxol. Luciferase-labeled M2 melanoma cells were injected intradermally into NOD/SCID mice. Mice were treated with control antibody (■), anti-DLL4 antibody (▲), taxol (○), or a combination of anti-DLL4 antibody and taxol (▼) (A). Data is shown as tumor volume (photons/sec) over days post-treatment. Antibodies were administered at 15 mg/kg once a week, and taxol was administered at 10 mg/kg once a week. Tumors were surgically removed from the mice after treatment and analyzed for apoptosis using a TUNEL assay (B).

As shown in FIG. 2A, anti-DLL4 antibody as a single agent reduced M2 melanoma tumor growth (p<0.001, T-test) and this reduction was greater than taxol alone (p=0.002, T-test). In addition, the combination of anti-DLL4 antibody and taxol demonstrated a greater reduction in tumor growth than either agent alone (p=0.04 vs anti-DLL4 antibody; p<0.0001 vs taxol, T-test).

The M2 melanoma tumors were surgically removed from the mice 33 days after treatment, were depleted of stromal cells and were analyzed for apoptosis. Apoptosis was assessed by detection of DNA strand breaks using a TUNEL assay which uses a fluorescently-labeled antibody which binds to DNA fragments. The percentage of apoptotic cells was determined after measuring the number of FITC/PI fluorescent cells using a flow cytometer.

Figure 2B:
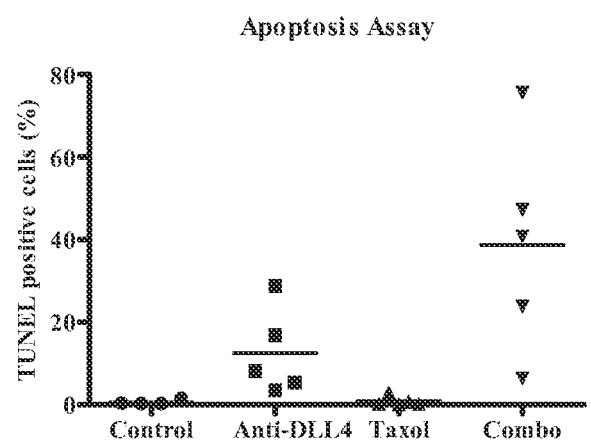

As shown in FIG. 2B, anti-DLL4 antibody treatment increased the percentage of apoptotic cells when administered alone, while taxol did not induce apoptosis in the melanoma tumor cells. Surprisingly, the combination of anti-DLL4 antibody and taxol increased the percentage of apoptotic cells to a greater extent (more than double) than anti-DLL4 antibody alone, even though taxol had no effect by itself.

The M2 melanoma tumors described above were processed to yield single cell suspensions, depleted of mouse cells and were serially transplanted into a new cohort of mice. 5, 10 or 25 tumor cells from each treatment group were injected into mice (n=10 mice per group). Tumors were allowed to grow untreated for 71 days. The "tumor take" rate was used to calculate the tumor initiating cell frequency (CSC frequency) using L-Calc™ software (StemCell Technologies Inc., Vancouver, BC). Briefly, based on Poisson statistics, exactly one tumor initiating cell exists among the known number of injected cells if 37% of the animals fail to develop tumors.

Figure 3:
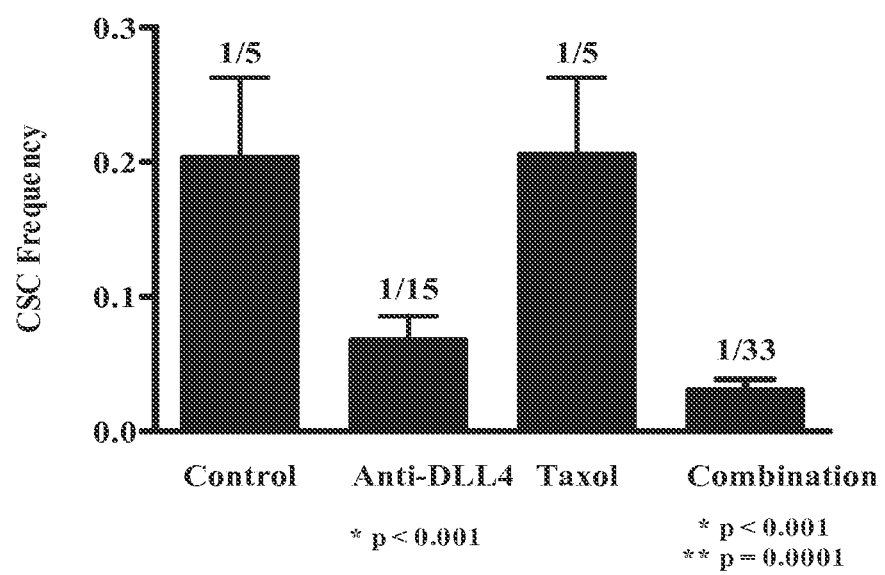
FIG. 3. Limiting dilution assay (LDA). Tumor initiating cell frequency in M2 melanoma tumors was determined following treatment with control antibody, anti-DLL4 antibody, taxol, or the combination of anti-DLL4 antibody and taxol using a limiting dilution analysis.

As shown in FIG. 3, the tumor initiating cell frequency in the group treated with the control antibody was 1:5. Treatment with anti-DLL4 antibody reduced tumor initiating cell frequency to 1:15, approximately a three-fold reduction compared to the control antibody. Treatment with taxol alone had no effect on tumor initiating frequency (1:5). Surprisingly, treatment with the combination of anti-DLL4 antibody and taxol demonstrated a greater reduction in tumor initiating cell frequency than with anti-DLL4 antibody alone and despite the fact that taxol alone had no effect. The combination of anti-DLL4 antibody and taxol reduced CSC frequency to 1:33, approximately a six-fold reduction compared to the control antibody, and almost a two-fold further reduction as compared to anti-DLL4 antibody alone.

Example 4

Inhibition of Melanoma Tumor Growth In Vivo by Anti-DLL4 Antibodies in Combination with a Chemotherapeutic Agent M8 melanoma tumor cells (50,000 cells) were injected subcutaneously into 6-8 week old NOD/SCID mice. Tumors were allowed to grow until the average tumor size was approximately 150 mm³. The animals were randomized into four groups (n=10 per group) and treated with a control antibody (anti-lysozyme antibody LZ-1, -■-), anti-DLL4 antibody (-♦-), taxol (-▲-), or a combination of taxol and anti-DLL4 antibody (-▼-). The anti-DLL4 antibody was a 1:1 mixture of anti-human DLL4 antibody and anti-mouse DLL4 antibody as described above. Antibodies were administered at 15 mg/kg once a week and taxol was administered at 10 mg/kg once a week. Both agents were administered intraperitoneally. Tumor growth was measured on the indicated days after treatment with electronic calipers.

Figure 4A:
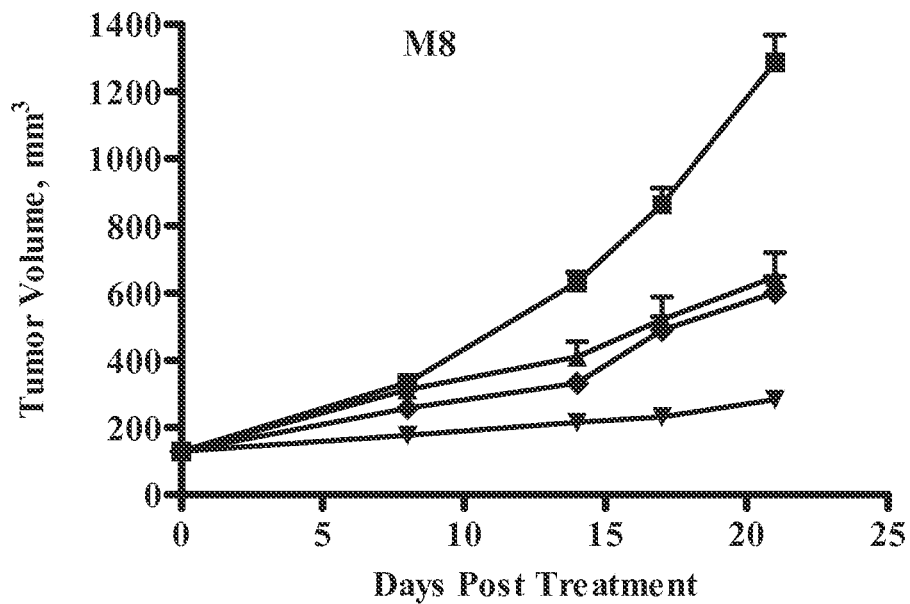
FIG. 4. Inhibition of melanoma tumor growth in vivo by anti-DLL4 antibody in combination with taxol. M8 (A) or M7 (B) melanoma tumor cells were injected subcutaneously into NOD/SCID mice. Mice were treated with control antibody (■), anti-DLL4 antibody (♦), taxol (▲), or a combination of anti-DLL4 antibody and taxol (▼). Data is shown as tumor volume (mm$^3$) over days post-treatment. Antibodies were administered at 15 mg/kg once a week, and taxol was administered at 10 mg/kg once a week.

As shown in FIG. 4A, treatment with the anti-DLL4 antibody resulted in reducing the growth of the M8 melanoma tumor. Furthermore, the combination of anti-DLL4 antibody and taxol demonstrated a greater reduction in tumor growth than either agent alone.

This experiment was repeated with a different melanoma tumor. M7 melanoma tumor cells (50,000 cells) were injected subcutaneously into 6-8 week old NOD/SCID mice. Tumors were allowed to grow until the average tumor size was approximately 150 mm³. The animals were randomized into four groups (n=10 per group) and treated with a control antibody (anti-lysozyme antibody LZ-1, -■-), anti-DLL4 antibody (-♦-), taxol (-▲-), or a combination of taxol and anti-DLL4 antibody (-▼-). The anti-DLL4 antibody was a 1:1 mixture of anti-human DLL4 antibody and anti-mouse DLL4 antibody as described above. Antibodies were administered at 15 mg/kg once a week and taxol was administered at 10 mg/kg once a week. Both agents were administered intraperitoneally. Tumor growth was measured on the indicated days after treatment with electronic calipers.

Figure 4B:
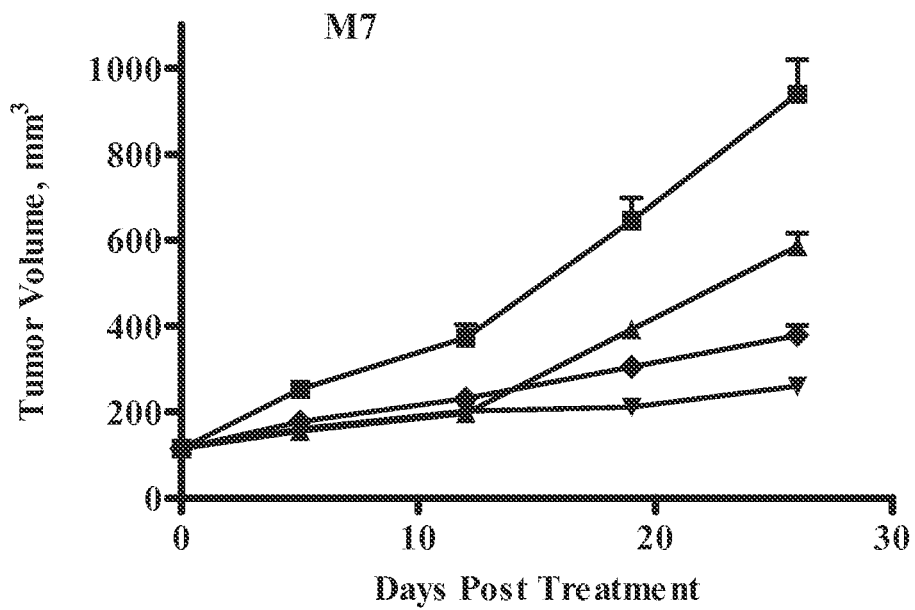

As shown in FIG. 4B, treatment with the anti-DLL4 antibody resulted in reducing growth of the M7 melanoma tumor to a greater extent than taxol. Furthermore, the combination of anti-DLL4 antibody and taxol demonstrated a greater reduction in tumor growth than either agent alone.

Example 5

Inhibition of Melanoma Tumor Growth In Vivo by Anti-DLL4 Antibodies in Combination with a B-Raf Inhibitor As described above in Example 1, DNA sequence analysis indicated that the M2 melanoma tumor contained a mutation (V600E) in the B-raf gene. Dissociated M2 melanoma tumor cells (50,000 cells) were injected intradermally into the flanks of 6-8 week old NOD/SCID mice. Tumors were allowed to grow until the average tumor size was approximately 150 mm$^3$. The animals were randomized (n=10 per group) and treated with a control antibody (anti-lysozyme antibody LZ-1, -■-), anti-DLL4 antibody (-▲-), B-raf inhibitor PLX4720 (-▼-), or a combination of anti-DLL4 antibody and PLX4720 (-●-). The anti-DLL4 antibody was a 1:1 mixture of anti-human DLL4 antibody and anti-mouse DLL4 antibody as described above. Antibodies were administered intraperitoneally at 15 mg/kg once a week. PLX4720 was administered at 20 mg/kg once a day orally. Tumor growth was measured on the indicated days after treatment with electronic calipers.

Figure 5:
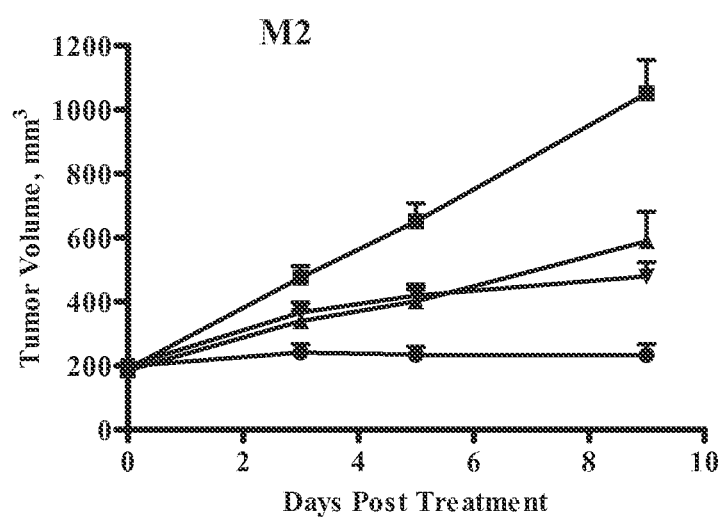
FIG. 5. Inhibition of melanoma tumor growth in vivo by anti-DLL4 antibody in combination with a B-raf inhibitor. M2 melanoma tumor cells were injected intradermally into NOD/SCID mice. Mice were treated with control antibody (■), anti-DLL4 antibody (▲), B-raf inhibitor PLX4720 (▼), or a combination of anti-DLL4 antibody and PLX4720 (●). Data is shown as tumor volume (mm$^3$) over days post-injection. Antibodies were administered at 15 mg/kg once a week, and PLX4720 was administered orally at 20 mg/kg once a day.

As shown in FIG. 5, PLX4720 reduced growth of the M2 melanoma tumor in this xenograft model. Treatment with anti-DLL4 antibody resulted in inhibiting growth of the melanoma tumor at a similar level as PLX4720. Importantly, the combination of anti-DLL4 antibody and PLX4720 demonstrated a greater reduction in melanoma tumor growth than either agent alone.

Example 6

Inhibition of Melanoma Tumor Growth In Vivo by Anti-DLL4 Antibodies in Combination with Dacarbazine (DTIC)

M2 and M3 melanoma tumor cells (50,000 cells) were injected intradermally (M2) or subcutaneously (M3) into 6-8 week old NOD/SCID mice. Tumors were allowed to grow until the average tumor size was approximately 150 mm$^3$. The animals were randomized into four groups (n=10 per group) and treated with a control antibody (anti-lysozyme antibody LZ-1, -■-), anti-DLL4 antibody (-▲-), dacarbazine (DTIC, -▼-), or a combination of dacarbazine and anti-DLL4 antibody (-●-). The anti-DLL4 antibody was a 1:1 mixture of anti-human DLL4 antibody and anti-mouse DLL4 antibody as described above. Antibodies were administered at 10 mg/kg twice a week and dacarbazine was administered at 80 mg/kg three times a week. Both agents were administered intraperitoneally. Tumor growth was measured on the indicated days after treatment with electronic calipers.

Figure 6A:
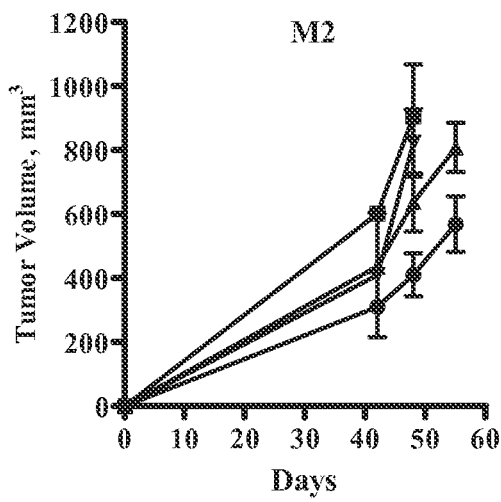
FIG. 6. Inhibition of melanoma tumor growth in vivo by anti-DLL4 antibody in combination with dacarbazine (DTIC). M2 (A) and M3 (B) melanoma tumor cells were injected intradermally (M2) or subcutaneously (M3) into NOD/SCID mice. Mice were treated with control antibody (■), anti-DLL4 antibody (▲), DTIC (▼) or a combination of anti-DLL4 antibody and DTIC (●). Data is shown as tumor volume (mm$^3$) over days post-injection. Antibodies were administered at 10 mg/kg twice a week, and DTIC was administered at 80 mg/kg three times a week.
Figure 6B:
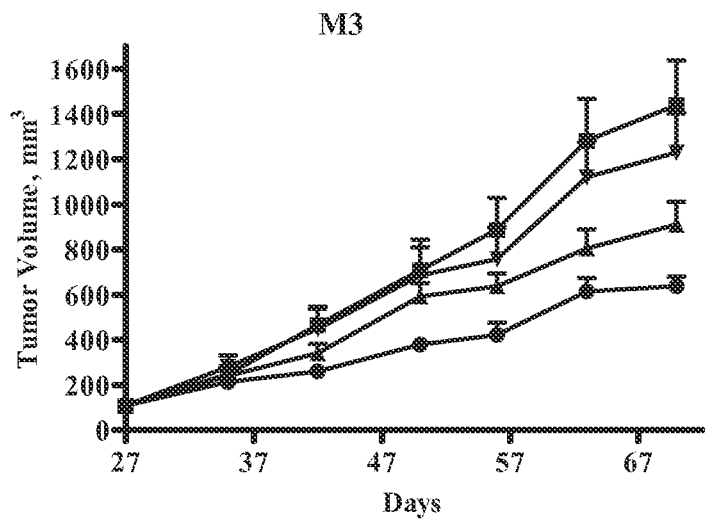

As shown in FIG. 6, treatment with anti-DLL4 antibody as a single agent resulted in reducing growth of the M2 (FIG. 6A) and M3 (FIG. 6B) melanoma tumor to a greater amount than dacarbazine (DTIC). Importantly, the combination of anti-DLL4 antibody and dacarbazine demonstrated a greater reduction in melanoma tumor growth than either agent alone (p=0.05 vs DTIC, Tukey's Test, one way-Anova).

Example 7

Inhibition of Melanoma and Metastatic Tumor Growth In Vivo by Anti-DLL4 Antibodies Luciferase-labeled M2 melanoma tumor cells (40,000 cells) were injected intradermally (orthotopic model) into 6-8 week old NOD/SCID mice. Tumor volumes were measured by determining the bioluminescent signal using an IVIS Imaging System (Caliper LifeSciences, Mountain View, Calif.). Tumors were allowed to grow until the average bioluminescent signal was approximately 2×10$^8$ photons/sec. The animals were randomized into two groups (n=10 per group) and treated with a control antibody (anti-lysozyme antibody LZ-1, -●-) or anti-DLL4 antibody (-■-). The anti-DLL4 antibody was a 1:1 mixture of anti-human DLL4 antibody and anti-mouse DLL4 antibody as described above. Antibodies were administered at 15 mg/kg once a week and were administered intraperitoneally. Tumor growth was measured by imaging the mice on the indicated days.

The tumor-bearing mice from this experiment were also analyzed for the presence of metastases. The growth of M2 melanoma tumors at metastatic sites was monitored by bioluminescence imaging. The lungs, brains and intestines from tumor-bearing mice were imaged ex vivo and the presence and/or growth of metastatic M2 cells was determined by analyzing the bioluminescent signal. In addition, RNA was prepared from liver tissue and analyzed by RT-PCR for expression of mouse and human GAPDH. The expression of human GAPDH in the mouse liver was used as evidence of metastatic M2 cells in the liver.

Figure 7A:
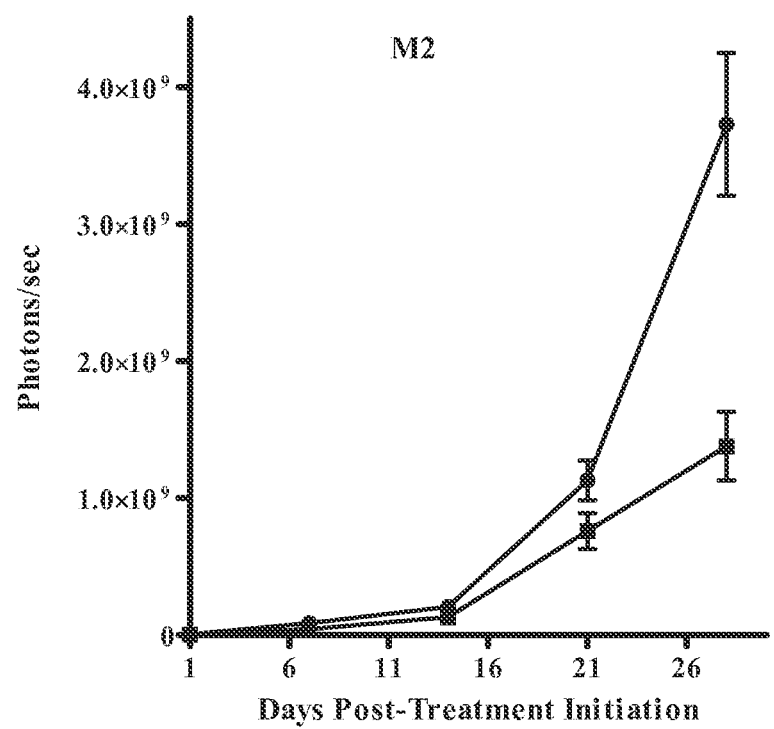
FIG. 7. Inhibition of melanoma primary tumor growth and metastatic tumor growth in vivo by anti-DLL4 antibodies. Luciferase-labeled M2 melanoma cells were injected intradermally into NOD/SCID mice. Mice were treated with control antibody (●) or anti-DLL4 antibody (■). Data is shown as tumor volume (photons/sec) over days post-treatment (A). Antibodies were administered at 15 mg/kg once a week. After treatment, mice were evaluated for metastases in brain (B), lung (C), and intestine (D) by measurement of bioluminescent signals and in liver (E) by RT-PCR.
Figure 7B:
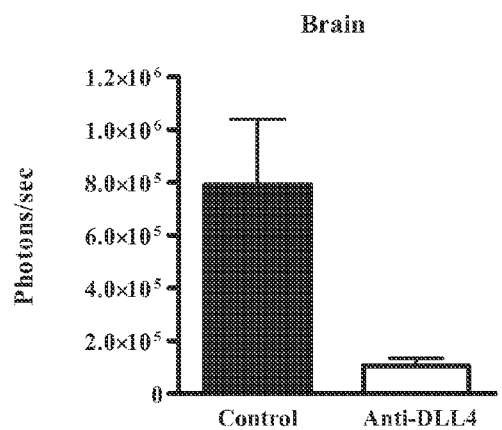
Figure 7C:
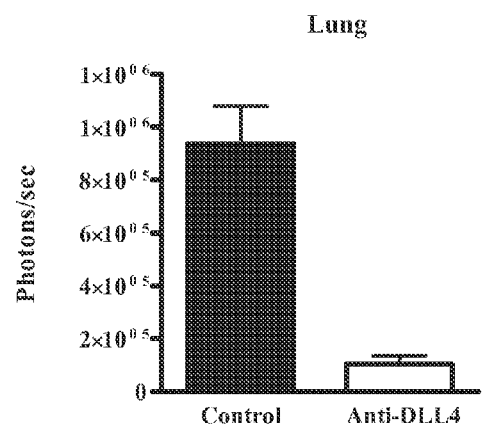
Figure 7D:
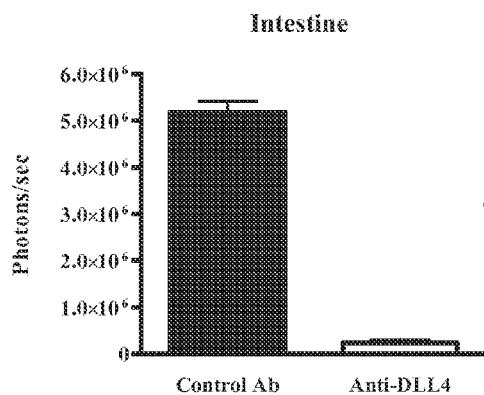
Figure 7E:
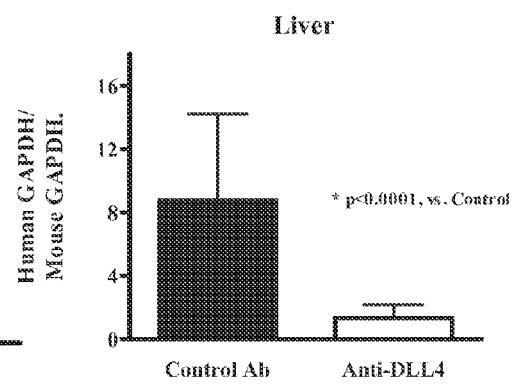

As shown in FIG. 7A, treatment with anti-DLL4 antibodies inhibited primary M2 melanoma tumor growth as compared to control antibody (p<0.0001, T-test). Furthermore, anti-DLL4 antibodies were shown to substantially reduce growth of metastatic M2 cells in the brain, lung, intestine and liver of tumor-bearing mice (p<0.001-0.0001, unpaired T-test) (FIG. 7B-7E).

Example 8

Inhibition of Melanoma Tumor Recurrence and Metastases In Vivo by Anti-DLL4 Antibodies Luciferase-labeled M2 melanoma tumor cells (40,000 cells) were injected intradermally (orthotopic model) into 6-8 week old NOD/SCID mice. Tumor volumes were measured by determining the bioluminescent signal using an IVIS Imaging System (Caliper LifeSciences, Mountain View, Calif.). Tumors were allowed to grow until the average bioluminescent signal was approximately 2×10$^8$ photons/sec. The animals were randomized into four groups (n=10 per group) and treated with a control antibody (anti-lysozyme antibody LZ-1), anti-DLL4 antibody, taxol, or a combination of taxol and anti-DLL4 antibody. The anti-DLL4 antibody was a 1:1 mixture of anti-human DLL4 antibody and anti-mouse DLL4 antibody as described above. Antibodies were administered at 15 mg/kg once a week and taxol was administered at 10 mg/kg once a week. Both agents were administered intraperitoneally. Tumor growth was measured by imaging the mice, and/or by measuring tumor volume with electronic calipers. The primary tumors were excised 30 days after treatment had been initiated. Treatment was continued after tumor excision and tumor recurrence and metastases were evaluated for up to 14 weeks.

Figure 8A:
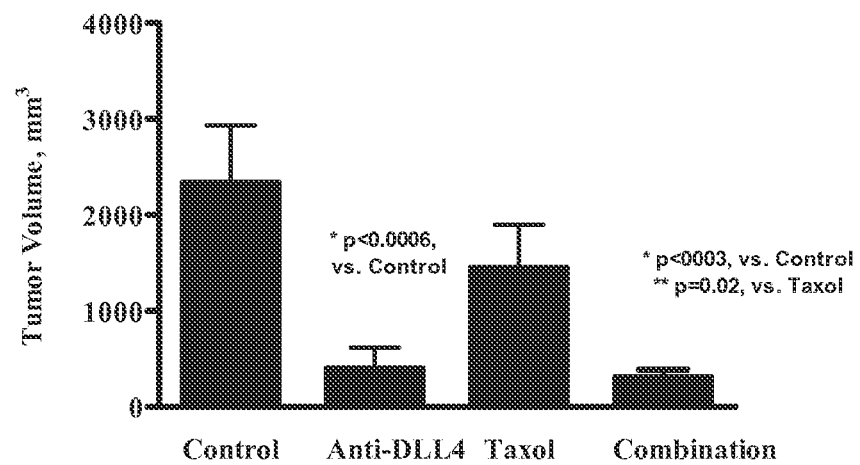
FIG. 8. Inhibition of M2 melanoma tumor recurrence and metastases in vivo by anti-DLL4 antibody in combination with taxol. Luciferase-labeled M2 melanoma cells were injected intradermally into NOD/SCID mice. Mice were treated with control antibody, anti-DLL4 antibody, taxol, or a combination of anti-DLL4 antibody and taxol. Antibodies were administered at 15 mg/kg once a week and taxol was administered at 10 mg/kg once a week. After 30 days of treatment, primary tumors were surgically removed, treatment was continued and mice were evaluated for tumor recurrence for up to 14 weeks. Data is shown as average tumor volume of recurrent tumors. (A) is average tumor volume by caliper measurement and (B) is average tumor volume by measurement of bioluminescent signal. Mice were also evaluated for metastases in lung (C), liver (D), intestine (E), brain (F) and lymph node (G) by measurement of bioluminescent signals in the tissue.
Figure 8B:
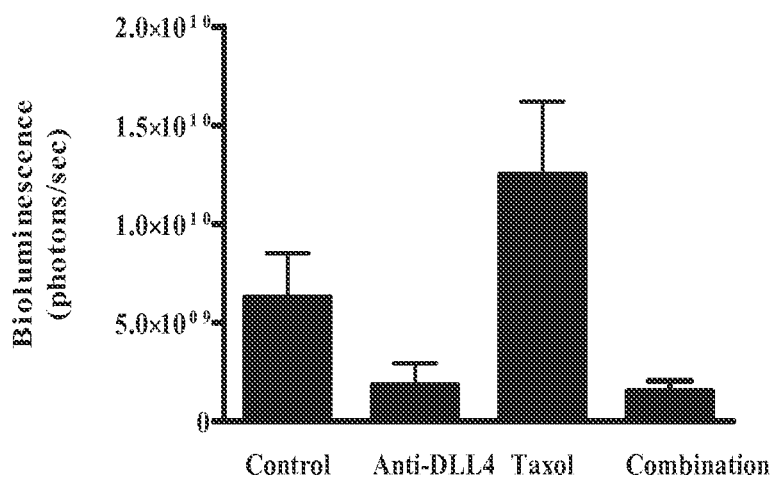
Figure 8C:
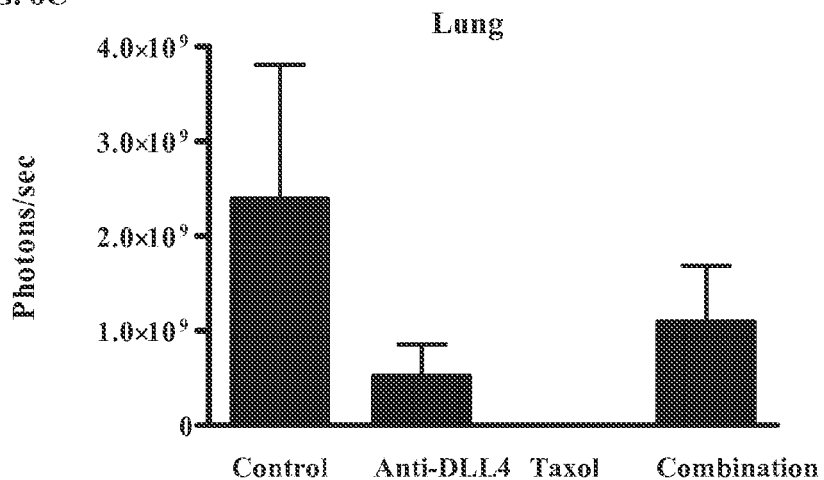
Figure 8D:
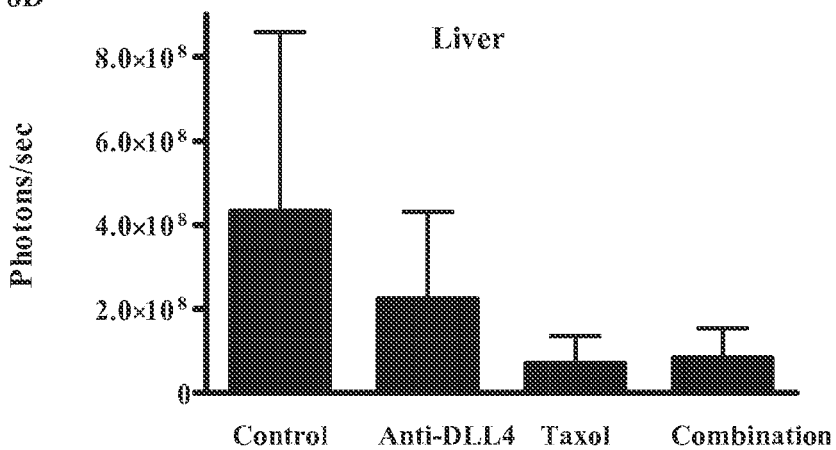
Figure 8E:
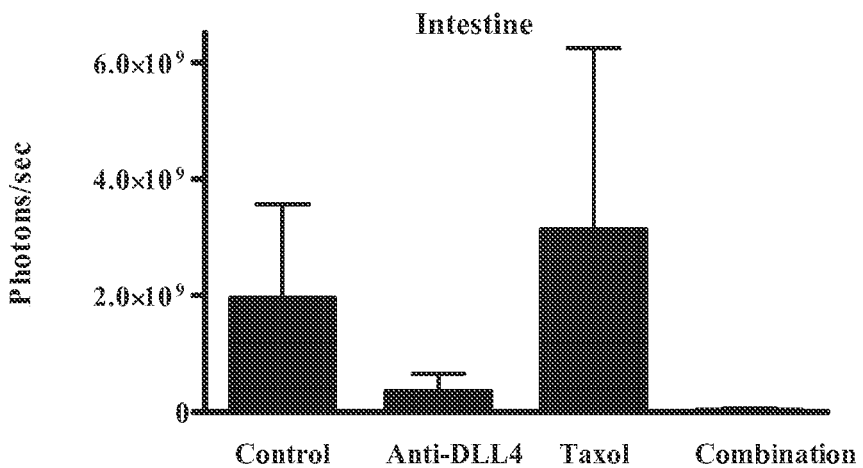
Figure 8F:
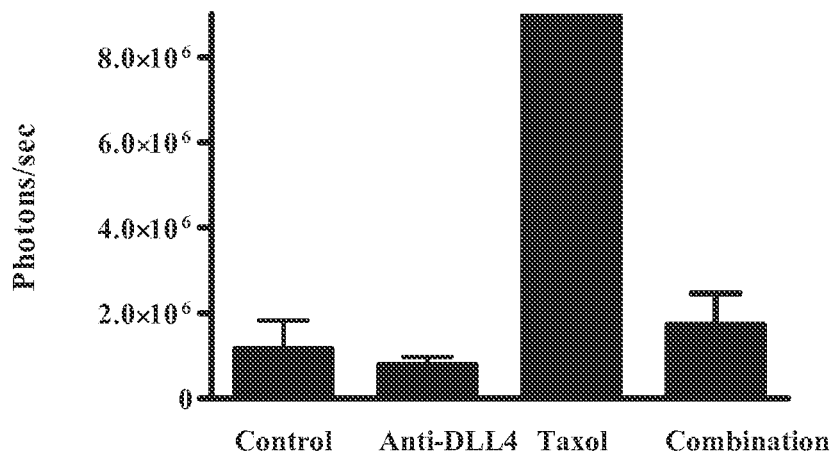

Nine of ten mice treated with control antibodies had recurrent melanoma tumors and five of the mice were euthanized 30 days after primary tumor excision due to tumor size. All nine mice treated with taxol had recurrent tumors and four of the mice were euthanized 30 days after primary tumor excision due to tumor size. In contrast, four mice treated with anti-DLL4 antibody had recurrent tumors, but the tumor size was much smaller and none were euthanized. Two of ten mice treated with the combination of anti-DLL4 antibody and taxol had no recurrent tumors and the rest had small tumors and none were euthanized. The average size of recurrent tumors for each treatment group is shown in FIG. 8A (tumor volume) and FIG. 8B (bioluminescent signal). Treatment with anti-DLL4 antibody reduced the average size of recurrent M2 melanoma tumors by approximately 6-fold (p=0.003 vs. control). The combination of anti-DLL4 antibody and taxol also significantly reduced the average size of recurrent M2 melanoma tumors (p=0.003 vs. control). The combination of anti-DLL4 antibody and taxol reduced the size of recurrent tumors to a significantly greater extent than taxol alone (p=0.02).

The mice from this experiment were also analyzed for the presence of metastases after the excision of the primary tumor. The growth of M2 melanoma tumors at metastatic sites was monitored by bioluminescence imaging. The lungs, liver, intestines, brain and lymph nodes from tumor-bearing mice were imaged ex vivo and the presence and/or growth of metastatic M2 cells was determined by analyzing the bioluminescent signal.

Figure 8G:
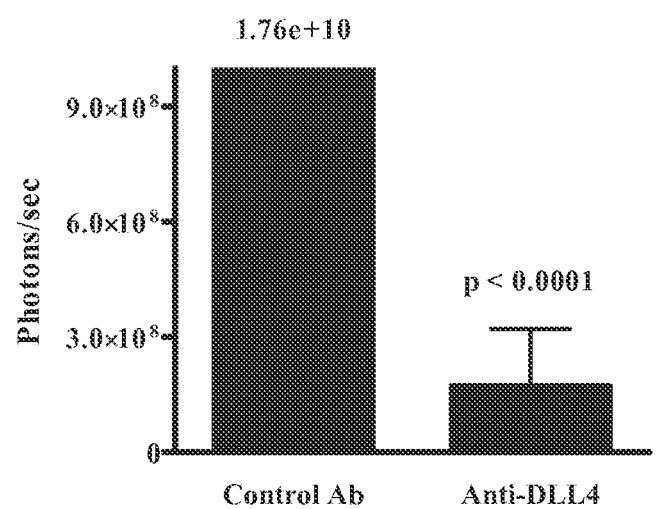

Treatment with anti-DLL4 antibody was shown to substantially reduce growth of metastatic M2 cells in the lungs (FIG. 8C, p=0.014), intestines (FIG. 8E, p<0.021), brain (FIG. 8F, p<0.020) and lymph nodes of mice (FIG. 8G, p<0.0001). Treatment reduced the growth of metastatic M2 cells in the liver (FIG. 8D) but to a lesser extent. Reduction in growth of metastatic M2 cells by treatment with taxol varied depending on the tissue being evaluated (FIG. 8C-8F). For example, in the intestines and brain, taxol appeared to significantly increase metastases, yet decreased metastases in the lungs and liver. Similarly, reduction in growth of metastatic M2 cells by treatment with the combination of anti-DLL4 antibody and taxol varied depending on the tissue being evaluated. For example, in the intestines, the combination reduced metastases to a greater extent than anti-DLL4 antibody alone and despite the fact that taxol had increased metastases to a level greater than even control. In the brain, the addition of anti-DLL4 antibody to taxol treatment appeared to almost totally negate the significant increase seen with taxol alone. The results seen in this experiment may reflect the different microenvironments found in these tissues.

It is understood that the examples and embodiments described herein are for illustrative purposes only and that various modifications or changes in light thereof will be suggested to persons skilled in the art and are to be included within the spirit and purview of this application.

All publications, patents, and patent applications cited herein are hereby incorporated by reference in their entirety for all purposes to the same extent as if each individual publication, patent or patent application were specifically and individually indicated to be so incorporated by reference.

```
SEQUENCES
SEQ ID NO: 1 Heavy chain CDR1
TAYYIH

SEQ ID NO: 2 Heavy chain CDR2, H2
YISCYNGATNYNQKFKG

SEQ ID NO: 3 Heavy chain CDR2, H7
YISSYNGATNYNQKFKG

SEQ ID NO: 4 Heavy chain CDR2, H9
YISVYNGATNYNQKFKG

SEQ ID NO: 5 Heavy chain CDR3
RDYDYDVGMDY

SEQ ID NO: 6 Heavy chain variable region without signal sequence, H7
QVQLVQSGAEVKKPGASVKISCKASGYSFTAYYIHWVKQAPGQGLEWIGYISSYNGATNY

NQKFKGRVTFTTDTSTSTAYMELRSLRSDDTAVYYCARDYDYDVGMDYWGQGTLVTVSS

SEQ ID NO: 7 Heavy chain variable region without signal sequence, H2
QVQLVQSGAEVKKPGASVKISCKASGYSFTAYYIHWVKQAPGQGLEWIGYISCYNGATNY

NQKFKGRVTFTTDTSTSTAYMELRSLRSDDTAVYYCARDYDYDVGMDYWGQGTLVTVSS

SEQ ID NO: 8 Heavy chain variable region without signal sequence, H9
QVQLVQSGAEVKKPGASVKISCKASGYSFTAYYIHWVKQAPGQGLEWIGYISVYNGATNY

NQKFKGRVTFTTDTSTSTAYMELRSLRSDDTAVYYCARDYDYDVGMDYWGQGTLVTVSS

SEQ ID NO: 9 Light chain CDR1
RASESVDNYGISFMK

SEQ ID NO: 10 Light chain CDR2
AASNQGS

SEQ ID NO: 11 Light chain CDR3
QQSKEVPWTFGG

SEQ ID NO: 12 Light chain variable region without signal sequence
DIVMTQSPDSLAVSLGERATISCRASESVDNYGISFMKWFQQKPGQPPKLLIYAASNQGS
```

GVPDRFSGSGSGTDFTLTISSLQAEDVAVYYCQQSKEVPWTFGGGTKVEIK

SEQ ID NO: 13 Human DLL4 Extracellular Domain
(with putative signal sequence underlined)
<u>MAAASRSASGWALLLLVALWQQRAAG</u>SGVFQLQLQEFINERGVLASGRPCEPGCRTFFRV

CLKHFQAVVSPGPCTFGTVSTPVLGTNSFAVRDDSSGGGRNPLQLPFNFTWPGTFSLIIE

AWHAPGDDLRPEALPPDALISKIAIQGSLAVGQNWLLDEQTSTLTRLRYSYRVICSDNYY

GDNCSRLCKKRNDHFGHYVCQPDGNLSCLPGWTGEYCQQPICLSGCHEQNGYCSKPAECL

CRPGWQGRLCNECIPHNGCRHGTCSTPWQCTCDEGWGGLFCDQDLNYCTHHSPCKNGATC

SNSGQRSYTCTCRPGYTGVDCELELSECDSNPCRNGGSCKDQEDGYHCLCPPGYYGLHCE

HSTLSCADSPCFNGGSCRERNQGANYACECPPNFTGSNCEKKVDRCTSNPCANGGQCLNR

GPSRMCRCRPGFTGTYCELHVSDCARNPCAHGGTCHDLENGLMCTCPAGFSGRRCEVRTS

IDACASSPCFNRATCYTDLSTDTFVCNCPYGFVGSRCEFPVG

SEQ ID NO: 14 Amino acids 27-217 of Human DLL4 Extracellular Domain
(without putative signal sequence)
SGVFQLQLQEFINERGVLASGRPCEPGCRTFFRVCLKHFQAVVSPGPCTFGTVSTPVLGT

NSFAVRDDSSGGGRNPLQLPFNFTWPGTFSLIIEAWHAPGDDLRPEALPPDALISKIAIQ

GSLAVGQNWLLDEQTSTLTRLRYSYRVICSDNYYGDNCSRLCKKRNDHFGHYVCQPDGNL

SCLPGWTGEYC

SEQ ID NO: 15 Human DLL4 N-Terminal Region
(with putative signal sequence underlined)
<u>MAAASRSASGWALLLLVALWQQRAAG</u>SGVFQLQLQEFINERGVLASGRPCEPGCRTFFRV

CLKHFQAVVSPGPCTFGTVSTPVLGTNSFAVRDDSSGGGRNPLQLPFNFTWPGTFSLIIE

AWHAPGDDLRPEALPPDALISKIAIQGSLAVGQN

SEQ ID NO: 16 Human DLL4 DSL Region
WLLDEQTSTLTRLRYSYRVICSDNYYGDNCSRLCKKRNDHFGHYVCQPDGNLSCLPGWTG

EYC

SEQ ID NO: 17 Amino acids 66-73 of Human DLL4
QAVVSPGP

SEQ ID NO: 18 Amino acids 139-146 of Human DLL4
LISKIAIQ

SEQ ID NO: 19 Human B-raf Kinase
MAALSGGGGGAEPGQALFNGDMEPEAGAGAGAAASSAADPAIPEEVWNIKQMIKLTQEH

IEALLDKFGGEHNPPSIYLEAYEEYTSKLDALQQREQQLLESLGNGTDFSVSSSASMDTV

TSSSSSSLSVLPSSLSVFQNPTDVARSNPKSPQKPIVRVFLPNKQRTVVPARCGVTVRDS

LKKALMMRGLIPECCAVYRIQDGEKKPIGWDTDISWLTGEELHVEVLENVPLTTHNFVRK

TFFTLAFCDFCRKLLFQGFRCQTCGYKFHQRCSTEVPLMCVNYDQLDLLFVSKFFEHHPI

PQEEASLAETALTSGSSPSAPASDSIGPQILTSPSPSKSIPIPQPFRPADEDHRNQFGQR

DRSSSAPNVHINTIEPVNIDDLIRDQGFRGDGGSTTGLSATPPASLPGSLTNVKALQKSP

GPQRERKSSSSSEDRNRMKTLGRRDSSDDWEIPDGQITVGQRIGSGSFGTVYKGKWHGDV

AVKMLNVTAPTPQQLQAFKNEVGVLRKTRHVNILLFMGYSTKPQLAIVTQWCEGSSLYHH

LHIIETKFEMIKLIDIARQTAQGMDYLHAKSIIHRDLKSNNIFLHEDLTVKIGDFGLATV

KSRWSGSHQFEQLSGSILWMAPEVIRMQDKNPYSFQSDVYAFGIVLYELMTGQLPYSNIN

NRDQIIFMVGRGYLSPDLSKVRSNCPKAMKRLMAECLKKKRDERPLFPQILASIELLARS

LPKIHRSASEPSLNRAGFQTEDFSLYACASPKTPIQAGGYGAFPVH

SEQ ID NO: 20 FLAG tag
DYKDDDDK

What is claimed:

1. A method of treating melanoma in a human subject, comprising:
administering a therapeutically effective amount of a delta like ligand-4 (DLL4) antagonist to the subject, wherein the subject's melanoma has been determined to comprise a wild-type B-raf or is substantially non-responsive to at least one B-raf inhibitor.

2. The method of claim 1, wherein the DLL4 antagonist is an antibody that specifically binds human DLL4.

3. The method of claim 2, wherein the antibody specifically binds an epitope within amino acids 27-217 of the extracellular domain of human DLL4 (SEQ ID NO:14).

4. The method of claim 2, wherein the antibody binds an epitope comprising amino acids 66-73 (QAVVSPGP, SEQ ID NO:17) of human DLL4.

5. The method of claim 2, wherein the antibody binds an epitope comprising amino acids 139-146 (LISKIAIQ, SEQ ID NO:18) of human DLL4.

6. The method of claim 2, wherein the antibody binds an epitope comprising amino acids 66-73 (QAVVSPGP, SEQ ID NO:17) and 139-146 (LISKIAIQ, SEQ ID NO:18) of human DLL4.

7. The method of claim 2, wherein the antibody comprises:
(a) a heavy chain CDR1 comprising TAYYIH (SEQ ID NO:1), a heavy chain CDR2 comprising YISCYNGATNYNQKFKG (SEQ ID NO:2), YISSYNGATNYNQKFKG (SEQ ID NO:3), or YISVYNGATNYNQKFKG (SEQ ID NO:4), and a heavy chain CDR3 comprising RDYDYDVGMDY (SEQ ID NO:5); and
(b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11).

8. The method of claim 7, wherein the antibody comprises:
(a) a heavy chain variable region having at least about 90% sequence identity to SEQ ID NO:6, SEQ ID NO:7 or SEQ ID NO:8; and
(b) a light chain variable region having at least about 90% sequence identity to SEQ ID NO:12.

9. The method of claim 8, wherein the antibody comprises:
(a) a heavy chain variable region having at least about 90% sequence identity to SEQ ID NO:7; and
(b) a light chain variable region having at least about 90% sequence identity to SEQ ID NO:12.

10. The method of claim 9, wherein the antibody comprises a heavy chain variable region of SEQ ID NO:7 and a light chain variable region of SEQ ID NO:12.

11. The method of claim 7, wherein the antibody comprises:
(a) a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and
(b) a light chain CDR1 comprising RASESVDNYGISFMK (SEQ ID NO:9), a light chain CDR2 comprising AASNQGS (SEQ ID NO:10), and a light chain CDR3 comprising QQSKEVPWTFGG (SEQ ID NO:11).

12. The method of claim 2, wherein the antibody is a recombinant antibody, a monoclonal antibody, a chimeric antibody, a humanized antibody, a human antibody, a bispecific antibody, an IgG1 antibody, an IgG2 antibody, or an antibody fragment.

13. The method of claim 2, wherein the antibody comprises the same heavy and light chain amino acid sequences as an antibody encoded by a plasmid deposited with ATCC having deposit no. PTA-8425 or PTA-8427.

14. The method of claim 2, wherein the antibody comprises the heavy chain CDR amino acid sequences and the light chain CDR amino acid sequences that are contained in the 21M18 antibody produced by the hybridoma deposited with ATCC having deposit no. PTA-8670.

15. The method of claim 2, wherein the antibody is encoded by the plasmid having ATCC deposit no. PTA-8425 or PTA-8427.

16. The method of claim 2, wherein the antibody is administered as part of a pharmaceutical composition.

17. The method of claim 1, wherein the melanoma tumor has metastasized.

18. The method of claim 1, further comprising administering to the subject a therapeutically effective amount of at least one additional therapeutic agent.

19. The method of claim 18, wherein the at least one additional therapeutic agent is a chemotherapeutic agent.

20. The method of claim 18, wherein the at least one additional therapeutic agent is an albumin-bound paclitaxel (ABRAXANE).

* * * * *

SEQUENCE LISTING

<160> NUMBER OF SEQ ID NOS: 20

<210> SEQ ID NO 1
<211> LENGTH: 6
<212> TYPE: PRT
<213> ORGANISM: Artificial
<220> FEATURE:
<223> OTHER INFORMATION: Heavy chain CDR1

<400> SEQUENCE: 1

Thr Ala Tyr Tyr Ile His
1               5

<210> SEQ ID NO 2
<211> LENGTH: 17
<212> TYPE: PRT
<213> ORGANISM: Artificial
<220> FEATURE:
<223> OTHER INFORMATION: Heavy chain CDR2, H2

<400> SEQUENCE: 2

Tyr Ile Ser Cys Tyr Asn Gly Ala Thr Asn Tyr Asn Gln Lys Phe Lys
1               5                   10                  15

Gly

<210> SEQ ID NO 3
<211> LENGTH: 17
<212> TYPE: PRT
<213> ORGANISM: Artificial
<220> FEATURE:
<223> OTHER INFORMATION: Heavy chain CDR2, H7

<400> SEQUENCE: 3

Tyr Ile Ser Ser Tyr Asn Gly Ala Thr Asn Tyr Asn Gln Lys Phe Lys
1               5                   10                  15

Gly

<210> SEQ ID NO 4
<211> LENGTH: 17
<212> TYPE: PRT
<213> ORGANISM: Artificial
<220> FEATURE:
<223> OTHER INFORMATION: Heavy chain CDR2, H9

<400> SEQUENCE: 4

Tyr Ile Ser Val Tyr Asn Gly Ala Thr Asn Tyr Asn Gln Lys Phe Lys
1               5                   10                  15

Gly

<210> SEQ ID NO 5
<211> LENGTH: 11
<212> TYPE: PRT
<213> ORGANISM: Artificial
<220> FEATURE:
<223> OTHER INFORMATION: Heavy chain CDR3

<400> SEQUENCE: 5

Arg Asp Tyr Asp Tyr Asp Val Gly Met Asp Tyr
1               5                   10

<210> SEQ ID NO 6
<211> LENGTH: 119
<212> TYPE: PRT
<213> ORGANISM: Artificial
<220> FEATURE:

```
<223> OTHER INFORMATION: Heavy chain variable region without signal
      sequence, H7

<400> SEQUENCE: 6

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Gly Ala Thr Asn Tyr Asn Gln Lys Phe
    50                  55                  60

Lys Gly Arg Val Thr Phe Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
                100                 105                 110

Thr Leu Val Thr Val Ser Ser
            115

<210> SEQ ID NO 7
<211> LENGTH: 119
<212> TYPE: PRT
<213> ORGANISM: Artificial
<220> FEATURE:
<223> OTHER INFORMATION: Heavy chain variable region without signal
      sequence, H2

<400> SEQUENCE: 7

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Cys Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
                100                 105                 110

Thr Leu Val Thr Val Ser Ser
            115

<210> SEQ ID NO 8
<211> LENGTH: 119
<212> TYPE: PRT
<213> ORGANISM: Artificial
<220> FEATURE:
<223> OTHER INFORMATION: Heavy chain variable region without signal
      sequence, H9

<400> SEQUENCE: 8

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
```

```
                20                  25                  30
Tyr Ile His Trp Val Lys Gln Ala Pro Gly Gln Gly Leu Glu Trp Ile
            35                  40                  45

Gly Tyr Ile Ser Val Tyr Asn Gly Ala Thr Asn Tyr Asn Gln Lys Phe
        50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
                100                 105                 110

Thr Leu Val Thr Val Ser Ser
            115

<210> SEQ ID NO 9
<211> LENGTH: 15
<212> TYPE: PRT
<213> ORGANISM: Artificial
<220> FEATURE:
<223> OTHER INFORMATION: Light chain CDR1

<400> SEQUENCE: 9

Arg Ala Ser Glu Ser Val Asp Asn Tyr Gly Ile Ser Phe Met Lys
1               5                   10                  15

<210> SEQ ID NO 10
<211> LENGTH: 7
<212> TYPE: PRT
<213> ORGANISM: Artificial
<220> FEATURE:
<223> OTHER INFORMATION: Light chain CDR2

<400> SEQUENCE: 10

Ala Ala Ser Asn Gln Gly Ser
1               5

<210> SEQ ID NO 11
<211> LENGTH: 12
<212> TYPE: PRT
<213> ORGANISM: Artificial
<220> FEATURE:
<223> OTHER INFORMATION: Light chain CDR3

<400> SEQUENCE: 11

Gln Gln Ser Lys Glu Val Pro Trp Thr Phe Gly Gly
1               5                   10

<210> SEQ ID NO 12
<211> LENGTH: 111
<212> TYPE: PRT
<213> ORGANISM: Artificial
<220> FEATURE:
<223> OTHER INFORMATION: Light chain variable region without signal
      sequence

<400> SEQUENCE: 12

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Asp Asn Tyr
            20                  25                  30

Gly Ile Ser Phe Met Lys Trp Phe Gln Gln Lys Pro Gly Gln Pro Pro
        35                  40                  45
```

```
Lys Leu Leu Ile Tyr Ala Ala Ser Asn Gln Gly Ser Gly Val Pro Asp
             50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Val Pro Trp Thr Phe Gly Gly Gly Thr Lys Val Glu Ile Lys
            100                 105                 110

<210> SEQ ID NO 13
<211> LENGTH: 522
<212> TYPE: PRT
<213> ORGANISM: Homo sapiens
<220> FEATURE:
<223> OTHER INFORMATION: DLL4 Extracellular Domain
<220> FEATURE:
<221> NAME/KEY: MISC FEATURE
<222> LOCATION: (1)..(26)
<223> OTHER INFORMATION: putative signal sequence

<400> SEQUENCE: 13

Met Ala Ala Ala Ser Arg Ser Ala Ser Gly Trp Ala Leu Leu Leu Leu
 1               5                  10                  15

Val Ala Leu Trp Gln Gln Arg Ala Ala Gly Ser Gly Val Phe Gln Leu
             20                  25                  30

Gln Leu Gln Glu Phe Ile Asn Glu Arg Gly Val Leu Ala Ser Gly Arg
         35                  40                  45

Pro Cys Glu Pro Gly Cys Arg Thr Phe Phe Arg Val Cys Leu Lys His
 50                  55                  60

Phe Gln Ala Val Val Ser Pro Gly Pro Cys Thr Phe Gly Thr Val Ser
 65                  70                  75                  80

Thr Pro Val Leu Gly Thr Asn Ser Phe Ala Val Arg Asp Asp Ser Ser
                 85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
            115                 120                 125

Leu Arg Pro Glu Ala Leu Pro Pro Asp Ala Leu Ile Ser Lys Ile Ala
        130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285
```

```
Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
                340                 345                 350

Gly Tyr Tyr Gly Leu His Cys Glu His Ser Thr Leu Ser Cys Ala Asp
            355                 360                 365

Ser Pro Cys Phe Asn Gly Gly Ser Cys Arg Glu Arg Asn Gln Gly Ala
        370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
                420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
        450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly
            515                 520

<210> SEQ ID NO 14
<211> LENGTH: 191
<212> TYPE: PRT
<213> ORGANISM: Artificial
<220> FEATURE:
<223> OTHER INFORMATION: Amino acids 27-217 of Human DLL4 Extracellular
      Domain

<400> SEQUENCE: 14

Ser Gly Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Thr Asn Ser Phe Ala
    50                  55                  60

Val Arg Asp Asp Ser Ser Gly Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
```

```
                 115                 120                 125

Trp Leu Leu Asp Glu Gln Thr Ser Thr Leu Thr Arg Leu Arg Tyr Ser
    130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys
            180                 185                 190

<210> SEQ ID NO 15
<211> LENGTH: 154
<212> TYPE: PRT
<213> ORGANISM: Homo sapiens
<220> FEATURE:
<223> OTHER INFORMATION: DLL4 N-Terminal Region
<220> FEATURE:
<221> NAME/KEY: MISC FEATURE
<222> LOCATION: (1)..(26)
<223> OTHER INFORMATION: putative signal sequence

<400> SEQUENCE: 15

Met Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn
145                 150

<210> SEQ ID NO 16
<211> LENGTH: 63
<212> TYPE: PRT
<213> ORGANISM: Homo sapiens
<220> FEATURE:
<223> OTHER INFORMATION: DLL4 DSL Region

<400> SEQUENCE: 16

Trp Leu Leu Asp Glu Gln Thr Ser Thr Leu Thr Arg Leu Arg Tyr Ser
1               5                   10                  15

Tyr Arg Val Ile Cys Ser Asp Asn Tyr Tyr Gly Asp Asn Cys Ser Arg
            20                  25                  30

Leu Cys Lys Lys Arg Asn Asp His Phe Gly His Tyr Val Cys Gln Pro
        35                  40                  45

Asp Gly Asn Leu Ser Cys Leu Pro Gly Trp Thr Gly Glu Tyr Cys
    50                  55                  60
```

<210> SEQ ID NO 17
<211> LENGTH: 8
<212> TYPE: PRT
<213> ORGANISM: Artificial
<220> FEATURE:
<223> OTHER INFORMATION: Amino acids 66-73 of Human DLL4

<400> SEQUENCE: 17

Gln Ala Val Val Ser Pro Gly Pro
1               5

<210> SEQ ID NO 18
<211> LENGTH: 8
<212> TYPE: PRT
<213> ORGANISM: Artificial
<220> FEATURE:
<223> OTHER INFORMATION: Amino acids 139-146 of Human DLL4

<400> SEQUENCE: 18

Leu Ile Ser Lys Ile Ala Ile Gln
1               5

<210> SEQ ID NO 19
<211> LENGTH: 766
<212> TYPE: PRT
<213> ORGANISM: Homo sapiens
<220> FEATURE:
<223> OTHER INFORMATION: B-raf Kinase

<400> SEQUENCE: 19

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

-continued

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
            245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
        290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ala Pro Asn
                355                 360                 365

Val His Ile Asn Thr Ile Glu Pro Val Asn Ile Asp Asp Leu Ile Arg
370                 375                 380

Asp Gln Gly Phe Arg Gly Asp Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
        450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
        530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
                595                 600                 605

Gln Phe Glu Gln Leu Ser Gly Ser Ile Leu Trp Met Ala Pro Glu Val
            610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr

```
                           645                  650                   655
Ser Asn Ile Asn Asn Arg Asp Gln Ile Ile Phe Met Val Gly Arg Gly
                660                  665                  670

Tyr Leu Ser Pro Asp Leu Ser Lys Val Arg Ser Asn Cys Pro Lys Ala
            675                  680                  685

Met Lys Arg Leu Met Ala Glu Cys Leu Lys Lys Lys Arg Asp Glu Arg
        690                  695                  700

Pro Leu Phe Pro Gln Ile Leu Ala Ser Ile Glu Leu Leu Ala Arg Ser
705                  710                  715                  720

Leu Pro Lys Ile His Arg Ser Ala Ser Glu Pro Ser Leu Asn Arg Ala
                725                  730                  735

Gly Phe Gln Thr Glu Asp Phe Ser Leu Tyr Ala Cys Ala Ser Pro Lys
            740                  745                  750

Thr Pro Ile Gln Ala Gly Gly Tyr Gly Ala Phe Pro Val His
        755                  760                  765

<210> SEQ ID NO 20
<211> LENGTH: 8
<212> TYPE: PRT
<213> ORGANISM: Artificial
<220> FEATURE:
<223> OTHER INFORMATION: FLAG tag

<400> SEQUENCE: 20

Asp Tyr Lys Asp Asp Asp Asp Lys
1               5
```